United States Patent [19]
Oka et al.

[11] Patent Number: 5,743,856
[45] Date of Patent: Apr. 28, 1998

[54] APPARATUS FOR MEASURING PULSE-WAVE PROPAGATION VELOCITY

[75] Inventors: Tohru Oka, Ichinomiya; Hiroshi Sakai, Komaki; Hidekatsu Inukai, Nagoya; Toshihiko Ogura, Inuyama; Tomoko Ikawa, Mino; Takashi Nomura, Komaki, all of Japan

[73] Assignee: Colin Corporation, Komaki, Japan

[21] Appl. No.: 718,715

[22] Filed: Sep. 24, 1996

[30] Foreign Application Priority Data

Nov. 6, 1995 [JP] Japan .................. 7-287339
Nov. 27, 1995 [JP] Japan .................. 7-307353
Nov. 27, 1995 [JP] Japan .................. 7-307354
Jan. 25, 1996 [JP] Japan .................. 8-010619

[51] Int. Cl.⁶ .......................................... A61B 5/02
[52] U.S. Cl. .............................. 600/493; 600/485
[58] Field of Search .................... 128/672, 679, 128/680, 681; 600/485, 492, 493, 494

[56] References Cited

FOREIGN PATENT DOCUMENTS

A-60-220037  11/1985  Japan .

Primary Examiner—William E. Kamm
Assistant Examiner—George R. Evanisko
Attorney, Agent, or Firm—Oliff & Berridge, PLC

[57] ABSTRACT

An apparatus for measuring a propagation velocity of a pulse wave which is propagated through an artery of a living subject, includes an electrocardiographic-waveform detecting device which detects an electrocardiographic waveform from the subject, a pulse-wave sensor which is adapted to be worn on the subject and which detects the pulse wave from the subject, a time-difference determining device for determining a time difference between a first periodic point relating to the detected electrocardiographic waveform and a second periodic point relating to the detected pulse wave, and a propagation-velocity determining device for determining the propagation velocity of the pulse wave based on the determined time difference.

14 Claims, 30 Drawing Sheets

APPARATUS FOR MEASURING PULSE-WAVE PROPAGATION VELOCITY

BACKGROUND OF THE INVENTION

1. Field of the Invention

The present invention relates to an apparatus for measuring the velocity of propagation of a pulse wave which is propagated through an artery of a living subject.

2. Related Art Statement

The blood pressure, degree of arterial sclerosis, peripheral resistance, etc. of a living subject can be estimated based on the velocity of propagation of a pulse wave which is propagated through an artery of the subject. There is known a pulse-wave propagation velocity measuring apparatus including a pair of pulse-wave sensors which are put on different locations on the skin of a living subject to press different portions of an artery of the subject via the skin and detect respective pulse waves from the artery. The measuring apparatus determines a pulse-wave propagation velocity based on the phase difference of the two pulse waves detected through the two sensors. The measuring apparatus is disclosed in, e.g., Unexamined Japanese Patent Application laid open for inspection purposes under Publication No. 60(1985)-220037.

The prior measuring apparatus measures the pulse-wave propagation velocity through the pulse-wave sensors being pressed against two portions of a superficial artery, such as carotid artery, radial artery, or dorsal pedal artery, that is adjacent to the skin of the subject. In this case, however, the time difference between the time of occurrence or detection of a heartbeat-synchronous pulse of one of the two pulses waves and the time of occurrence or detection of a corresponding heartbeat-synchronous pulse of the other pulse wave is small, because the length or distance between the two portions of the superficial artery is short. Thus, the time difference may not be relied upon for providing a very accurate pulse-wave propagation velocity.

SUMMARY OF THE INVENTION

It is therefore an object of the present invention to provide an apparatus for measuring a very accurate pulse-wave propagation velocity.

The above object has been achieved by the present invention. According to a first aspect of the present invention, there is provided an apparatus for measuring a propagation velocity of a pulse wave which is propagated through an artery of a living subject, the apparatus comprising an electrocardiographic-waveform detecting device which detects an electrocardiographic waveform from the subject, a pulse-wave sensor which is adapted to be worn on the subject and which detects the pulse wave from the subject, time-difference determining means for determining a time difference between a first periodic point relating to the detected electrocardiographic waveform and a second periodic point relating to the detected pulse wave, and propagation-velocity determining means for determining the propagation velocity of the pulse wave based on the determined time difference.

In the pulse-wave measuring apparatus in accordance with the first aspect of the invention, the time difference determined by the time-difference determining means contains a time duration when the pulse wave is propagated through the aorta directly connected to the heart of the subject. Therefore, the length of the artery through which the pulse wave is propagated is increased and accordingly the time difference is increased. In addition, since the diameter of the aorta is large and accordingly the velocity of the pulse wave being propagated through the aorta is decreased, the time difference is increased. Thus, the present apparatus provides a very accurate pulse-wave propagation velocity. Therefore, the degree of arterial sclerosis, or the blood pressure, of the subject can be estimated with high accuracy based on the thus determined pulse-wave propagation velocity.

According to a preferred feature of the first aspect of the invention, the pulse-wave sensor comprises a pressure sensor which is adapted to be pressed against a portion of the artery of the subject via a skin of the subject and which detects, as the pulse wave, a heartbeat-synchronous pressure oscillation which is transmitted thereto from the portion of the artery via the skin. In the case where the present invention is applied to a BP monitor apparatus including an identical pressure sensor for monitoring BP values of a subject, the pressure sensor is used for the two purposes, one for detecting a pulse wave and thereby measuring a pulse-wave propagation velocity and the other for monitoring BP values. The BP monitor apparatus having the pulse-wave propagation velocity measuring function enjoys a reduced production cost.

According to another feature of the first aspect of the invention, the pulse-wave sensor comprises an inflatable cuff which is adapted to be wound around a body portion of the subject, and a pressure sensor which detects, as the pulse wave, a heartbeat-synchronous pressure oscillation which is produced in the cuff. In the case where the present invention is applied to a BP measuring apparatus including identical cuff and pressure sensor for measuring a BP value of a subject, the cuff and pressure sensor are used for the two purposes, one for detecting a pulse wave and thereby measuring a pulse-wave propagation velocity and the other for measuring a BP value. The BP measuring apparatus having the pulse-wave propagation velocity measuring function enjoys a reduced production cost.

According to another feature of the first aspect of the invention, the pulse-wave sensor comprises a photoelectric sensor including a light source which emits a light toward a body portion of the subject, and a light detecting element which detects the light transmitted through, or reflected from, the body portion. In the case where the present invention is applied to a blood-oxygen-saturation measuring apparatus (e.g., so-called pulse oximeter) having an identical photoelectric sensor for measuring a blood oxygen saturation of a subject, the photoelectric sensor is used for the two purposes, one for detecting a pulse wave and thereby measuring a pulse-wave propagation velocity and the other for measuring a blood oxygen saturation. The oxygen-saturation measuring apparatus having the pulse-wave propagation velocity measuring function enjoys a reduced production cost.

According to a second aspect of the present invention, there is provided an apparatus for measuring a propagation velocity of a pulse wave which is propagated through an artery of a living subject, the apparatus comprising a blood-pressure measuring device which measures a blood pressure value of the subject, an electrocardiographic-waveform detecting device which includes a plurality of electrodes adapted to contact a body surface of the subject and which detects an electrocardiographic waveform from the subject through the electrodes, a pulse-wave sensor which is adapted to be worn on the subject and which detects the pulse wave from the subject, time-difference determining means for determining a time difference between a first periodic point relating to the detected electrocardiographic waveform and a second periodic point relating to the detected pulse wave, propagation-velocity determining means for determining the propagation velocity of the pulse wave based on the determined time difference, and propagation-velocity modifying means for modifying the determined propagation-velocity value to a modified propagation-velocity value corresponding to a predetermined blood pressure value, based on the measured blood pressure value, according to a predetermined relationship between modified propagation velocity, and determined propagation velocity and measured blood pressure.

While the pulse-wave propagation velocity is influenced by the degree of arterial sclerosis, it is also influenced by the blood pressure and/or the pulse rate of the subject. However, the blood pressure (BP) values of the subject will change more or less in different measurements. Therefore, the propagation velocity measured by the prior apparatus may not directly be used as an index indicative of a degree of arterial sclerosis. In the pulse-wave propagation velocity measuring apparatus in accordance with the second aspect of the invention, however, the modified pulse-wave propagation velocity provided by the propagation-velocity modifying means can directly be used as an index indicative of a degree of arterial sclerosis. Thus, even if the BP or pulse-rate values obtained from the subject in different measurements may differ from each other, the present apparatus modifies each measured propagation velocity value to a modified propagation velocity corresponding to the predetermined BP value. Accordingly, a series of modified propagation-velocity values can directly be used as an index indicative of a time-wise change of the degree of arterial sclerosis of the subject.

According to a preferred feature of the second aspect of the invention, the propagation velocity measuring apparatus further comprises a pulse-rate measuring device which measures a pulse rate value of the subject, and the propagation-velocity modifying means comprises means for modifying the determined propagation-velocity value to the modified propagation-velocity value corresponding to the predetermined blood pressure value and a predetermined pulse rate value, based on the measured blood pressure value and the measured pulse rate value, according to the predetermined relationship between modified propagation velocity, and determined propagation velocity, measured blood pressure value, and measured pulse rate. Since the thus modified propagation-velocity value corresponds to both the predetermined BP and pulse-rate values, it is more accurate than a modified value corresponding to only the predetermined BP value, because the former value is free from influences from the fluctuation of the pulse rate whereas the latter value is subject to them.

According to another feature of the second aspect of the invention, the propagation velocity measuring apparatus further comprises coefficient determining means for determining a coefficient which is variable with the propagation velocity determined by the propagation-velocity determining means and with the blood pressure measured by the blood-pressure measuring device, and the propagation-velocity modifying means comprises means for modifying the determined propagation-velocity value to the modified propagation-velocity value corresponding to the predetermined blood pressure value, such that the modified propagation-velocity value is equal to a product of the determined coefficient and a difference between the predetermined blood pressure value and the measured blood pressure value. Thus, the modified propagation velocity is determined using the coefficient which is determined based on the propagation velocity and the diastolic BP value each obtained from the subject. Owing to the coefficient, the modified value is free from influences or fluctuations due to the differences of individual persons regarding the degree of arterial sclerosis. Therefore, the modified propagation-velocity values obtained from different subjects can be compared with each other for comparing the respective degrees of arterial sclerosis of those subjects.

According to another feature of the second aspect of the invention, the propagation velocity measuring apparatus further comprises means for determining a degree of arterial sclerosis based on the modified propagation-velocity value according to a predetermined relationship between degree of arterial sclerosis and modified propagation velocity.

According to a third aspect of the present invention, there is provided an apparatus for measuring a propagation velocity of a pulse wave which is propagated through an artery of a living subject, the apparatus comprising a blood-pressure measuring device which includes an inflatable cuff adapted to be wound around a body portion of the subject, a pulse-wave sensor which detects the pulse wave transmitted from the artery of the subject to the cuff when a pressure in the cuff is changed, and means for determining a blood pressure value of the subject based on the detected pulse wave, an electrocardiographic-waveform detecting device which includes a plurality of electrodes adapted to contact a body surface of the subject and which detects an electrocardiographic waveform from the subject through the electrodes, time-difference determining means for successively determining a time difference between a first periodic point relating to the detected electrocardiographic waveform and a second periodic point relating to the detected pulse wave, temporary-propagation-velocity determining means for successively determining a temporary propagation velocity of the pulse wave based on each of the successively determined time-difference values, judging means for judging whether the change of each of the successively determined temporary propagation-velocity values with respect to the change of the cuff pressure is smaller than a reference value, and proper-propagation-velocity determining means for determining a proper propagation velocity from at least one temporary propagation-velocity value for which a positive judgment is made by the judging means.

There is known a BP measuring device which includes an inflatable cuff adapted to be wound around a body portion of the subject, a pulse-wave sensor which detects the pulse wave transmitted from the artery of the subject to the cuff when a pressure in the cuff is changed, and means for determining a blood pressure value of the subject based on the detected pulse wave. The BP measuring device is disclosed in, e.g., U.S. patent application Ser. No. 08/273,929. In the case where the present invention is embodied with the BP measuring device, however, the (temporary) propagation-velocity values determined by the (temporary) propagation-velocity determining means gradually increase as the pressure of the cuff gradually decreases, when the cuff pressure is changed in a range above a mean BP value of the subject. In the pulse-wave propagation velocity measuring apparatus in accordance with the third aspect of the invention, the judging means judges whether the change of each of the determined temporary propagation-velocity values with respect to the change of the cuff pressure is smaller than a reference value, and the proper-propagation-velocity determining means determines a proper propagation velocity from at least one temporary propagation-velocity value for which a positive judgment is made by the judging means.

Since the proper propagation-velocity value is determined from the temporary propagation value or values that is or are stable independent of the change of cuff pressure, the accuracy of measurement of pulse-wave propagation velocity is improved.

According to a preferred feature of the third aspect of the invention, the proper-propagation-velocity determining means comprises means for determining, as the proper propagation velocity, an average of a plurality of temporary propagation-velocity values for each of which the positive judgment is made by the judging means. The thus determined proper propagation velocity enjoys a higher accuracy than a proper propagation velocity as one of a plurality of temporary propagation-velocity values for each of which the positive judgment is made by the judging means. However, the proper-propagation-velocity determining means may comprise means for determining, as the proper propagation velocity, a temporary propagation-velocity values for which a positive judgment is made by the judging means.

According to another feature of the third aspect of the invention, the propagation velocity measuring apparatus further comprises proper-propagation-velocity modifying means for modifying the determined proper propagation-velocity value to a modified proper propagation-velocity value corresponding to a predetermined blood pressure value, based on the measured blood pressure value, according to a predetermined relationship between modified proper propagation velocity, and determined proper propagation velocity and measured blood pressure.

According to another feature of the third aspect of the invention, the propagation velocity measuring apparatus further comprises means for determining a degree of arterial sclerosis of the subject based on the modified proper propagation-velocity value according to a predetermined relationship between degree of arterial sclerosis and modified proper propagation velocity.

According to a fourth aspect of the present invention, there is provided an apparatus for measuring a propagation velocity of a pulse wave which is propagated through an artery of a living subject, the apparatus comprising a blood-pressure measuring device which includes an inflatable cuff adapted to be wound around a body portion of the subject, a pulse-wave sensor which detects a plurality of heartbeat-synchronous pulses of the pulse wave transmitted from the artery of the subject to the cuff when a pressure in the cuff is changed, and means for determining a blood pressure value of the subject based on variation of respective amplitudes of the detected heartbeat-synchronous pulses of the pulse wave, an electrocardiographic-waveform detecting device which includes a plurality of electrodes adapted to contact a body surface of the subject and which detects an electrocardiographic waveform from the subject through the electrodes, time-difference determining means for successively determining a time difference between a first periodic point relating to each of heartbeat-synchronous pulses of the detected electrocardiographic waveform and a second periodic point relating to a corresponding one of the detected heartbeat-synchronous pulses of pulse wave, propagation-velocity determining means for successively determining a propagation velocity of the pulse wave based on each of the successively determined time-difference values, judging means for judging whether the change of each of the successively determined propagation-velocity values with respect to the change of the cuff pressure is smaller than a reference value, and correcting means for correcting at least one first pulse of the heartbeat-synchronous pulses of the pulse wave which is deviated from at least one second pulse for which a positive judgment is made by the judging means, based on the deviation of the first pulse from the second pulse, so that the blood-pressure measuring device measures the blood pressure value of the subject based on the variation of the respective amplitudes of the heartbeat-synchronous pulses including the corrected first pulse.

In the case where the present invention is embodied with the BP measuring device which determines a BP value of the subject based on variation of respective amplitudes of heartbeat-synchronous pulses of the pulse wave obtained when the cuff pressure is changed, the relationship of correspondence of pulse amplitude and cuff pressure (or blood pressure) may break for a certain reason during each BP measuring operation of the BP measuring device. Hence, if a first pulse of the heartbeat-synchronous pulses of the pulse wave is deviated from one or more second pulses corresponding to one or more propagation-velocity values for each of which a positive judgment is made by the judging means, the correcting means corrects the first pulse, e.g., amplitude of the first pulse, or value of the cuff pressure at the time of detection of the first pulse, so that the BP measuring device measures a BP value of the subject based on the variation of respective amplitudes of heartbeat-synchronous pulses including the corrected first pulse. Thus, the accuracy of measurement of BP values is improved.

According to a preferred feature of the fourth aspect of the invention, the correcting means comprises estimating means for estimating, based on a plurality of the determined propagation-velocity values for each of which the positive judgment is made by the judging means, a next propagation-velocity value which will be determined by the propagation-velocity determining means, and difference determining means for determining a difference between the estimated next propagation-velocity value and an actual next propagation-velocity actually determined by the propagation-velocity determining means.

According to another feature of the fourth aspect of the invention, the correcting means further comprises means for determining a correction value based on the determined difference according to a predetermined expression, and adding the correction value to an amplitude of the first pulse. Thus, the first pulse is corrected.

According to another feature of the fourth aspect of the invention, the correcting means further comprises means for determining a correction value based on the determined difference according to a predetermined expression, and adding the correction value to a value of the cuff pressure at a time of detection of the first pulse. Thus, the first pulse is corrected.

According to a fifth aspect of the present invention, there is provided an apparatus for measuring a propagation velocity of a pulse wave which is propagated through an artery of a living subject, the apparatus comprising, a blood-pressure measuring device which includes an inflatable cuff adapted to be wound around a body portion of the subject, a pulse-wave sensor which detects the pulse wave transmitted from the artery of the subject to the cuff when a pressure in the cuff is changed, and means for determining a blood pressure value of the subject based on the detected pulse wave, an electrocardiographic-waveform detecting device which includes a plurality of electrodes adapted to contact a body surface of the subject and which detects an electrocardiographic waveform from the subject through the electrodes, time-difference determining means for determining a time difference between a first periodic point relating to the detected electrocardiographic waveform and a second periodic point on relating to the detected pulse wave, propagation-velocity determining means for determining a propagation velocity of the pulse wave based on the determined time-difference value, and terminating means for terminating a blood pressure measurement of the blood-pressure measuring device when the determined propagation-velocity value does not fall within a permission range.

In the case where the present invention is embodied with the BP measuring device which determines a BP value of the subject based on the pulse wave obtained when the cuff pressure is changed, the relationship of correspondence of pulse wave and cuff pressure (or blood pressure) may break for a certain reason during each BP measuring operation of the BP measuring device. Hence, if an abnormal event occurs during each BP measurement and the propagation velocity excessively changes, i.e., increases or decreases, the BP measurement is forcedly terminated. Thus, an inaccurate BP measurement or value is effectively avoided.

According to a preferred feature of the fifth aspect of the invention, the propagation velocity measuring apparatus further comprises a memory which stores data indicative of a plurality of the permission ranges corresponding to a plurality of values of the cuff pressure at which a plurality of propagation-velocity values are determined by the propagation-velocity determining means.

According to a sixth aspect of the present invention, there is provided an apparatus for measuring a propagation velocity of a pulse wave which is propagated through an artery of a living subject, the apparatus comprising, a first and a second heartbeat-synchronous-wave sensor which detect, as the pulse wave, a first and a second heartbeat-synchronous wave, respectively, each of which is produced from the artery of the subject in synchronism with a heartbeat of the subject, maximum-slope-line determining means for determining, with respect to at least one of the first and second waves, a maximum-slope line which passes through a maximum-slope point where a heartbeat-synchronous pulse of the one wave takes a maximum slope, such that the maximum-slope line has the maximum slope, base-line determining means for determining, with respect to the one wave, a base line which passes through respective minimum points on both sides of a maximum point of the heartbeat-synchronous pulse of the one wave, reference-point determining means for determining, as a reference point, a point of intersection of the maximum-slope line and the base line, and propagation-velocity determining means for determining the propagation velocity of the pulse wave based on a time difference between the reference point determined with respect to the heartbeat-synchronous pulse of the one wave and a corresponding heartbeat-synchronous pulse of the other of the first and second waves.

The pulse wave propagated through the artery of the subject contains, as a primary component, a travelling wave and additionally contains, as a secondary component, a reflected wave produced when the travelling wave is reflected by the wall of the artery, e.g., bifurcate wall, as illustrated in FIG. 25. Since, generally, the component of the reflected wave is weak relative to the component of the travelling wave, the maximum point of each travelling wave can be estimated as the maximum point of each pulse wave. However, as the arterial sclerosis becomes worse, the component of the reflected wave becomes stronger, and the maximum point of each pulse wave is more influenced by the component of the reflected wave, as shown in FIG. 29. If the maximum point of the pulse wave is used as a reference point for determining a pulse-wave propagation velocity, then the propagation velocity may largely change depending upon the degree of arterial sclerosis of the subject and/or the shape of the artery wall where the pulse wave is detected. In the pulse-wave propagation velocity measuring apparatus in accordance with the sixth aspect of the invention, however, the reference-point determining means determines, as the reference point, a point of intersection of the maximum-slope line and the base line. This reference point ($T_S$) is free from the influences of the reflected wave, as illustrated in FIG. 25. Thus, the reference point does not change or move relative to the pulse wave even if the subject may have a serious arterial sclerosis. Accordingly, the present apparatus measures, with high accuracy, the propagation velocity of the pulse wave.

According to a seventh aspect of the present invention, there is provided an apparatus for measuring a propagation velocity of a pulse wave which is propagated through an artery of a living subject, the apparatus comprising, a first and a second heartbeat-synchronous-wave sensor which detect, as the pulse wave, a first and a second heartbeat-synchronous wave, respectively, each of which is produced from the artery of the subject in synchronism with a heartbeat of the subject, maximum-slope-line determining means for determining, with respect to at least one of the first and second waves, a maximum-slope line which passes through a maximum-slope point where a heartbeat-synchronous pulse of the one wave takes a maximum slope, such that the maximum-slope line has the maximum slope, maximum-point-line determining means for determining, with respect to the one wave, a maximum-point line which passes through a maximum point where the heartbeat-synchronous pulse of the one wave takes a maximum amplitude, such that the maximum-point line is parallel to a base line which passes through respective minimum points on both sides of the maximum point of the heartbeat-synchronous pulse of the one wave, reference-point determining means for determining a reference point from a point of intersection of the one wave and a line which passes through a point of intersection of the maximum-slope line and the maximum-point line and is perpendicular to the maximum-point line, and propagation-velocity determining means for determining the propagation velocity of the pulse wave based on a time difference between the reference point determined with respect to the heartbeat-synchronous pulse of the one wave and a corresponding heartbeat-synchronous pulse of the other of the first and second waves.

In the pulse-wave propagation velocity measuring apparatus in accordance with the seventh aspect of the invention, the reference-point determining means determines the reference point from a point of intersection of the one wave and a line which passes through a point of intersection of the maximum-slope line and the maximum-point line and is perpendicular to the maximum-point line. The reference point may be determined as being equal to the point of intersection of the one wave and the line or otherwise be determined based on the intersection point. This reference point ($T_S$) is free from the influences of the reflected wave, as illustrated in FIG. 29. Thus, the reference point does not change or move relative to the pulse wave even if the subject may have a serious arterial sclerosis. Accordingly, the present apparatus measures, with high accuracy, the propagation velocity of the pulse wave.

According to an eighth aspect of the present invention, there is provided an apparatus for measuring a propagation velocity of a pulse wave which is propagated through an artery of a living subject, the apparatus comprising a first and a second heartbeat-synchronous-wave sensor which detect, as the pulse wave, a first and a second heartbeat-synchronous wave, respectively, each of which is produced from the artery of the subject in synchronism with a heartbeat of the subject, reference-point determining means for determining, with respect to at least one of the first and second waves, a maximum-slope point where a heartbeat-synchronous pulse of the one wave takes a maximum slope, and determining the determined maximum-slope point as a reference point, and propagation-velocity determining means for determining the propagation velocity of the pulse wave based on a time difference between the reference point determined with respect to the heartbeat-synchronous pulse of the one wave and a corresponding heartbeat-synchronous pulse of the other of the first and second waves.

In the pulse-wave propagation velocity measuring apparatus in accordance with the eighth aspect of the invention, the reference-point determining means determines, as the reference point, a maximum-slope point where the pulse wave takes a maximum slope. This reference point ($K_{max}$) is free from the influences of the reflected wave, as illustrated in FIG. 25 or 29. Thus, the reference point does not change or move relative to the pulse wave even if the subject may have a serious arterial sclerosis. Accordingly, the present apparatus measures, with high accuracy, the propagation velocity of the pulse wave.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Referring first to FIGS. 1 through 7, there will be described a first embodiment of the present invention which relates to a blood-pressure (BP) monitor apparatus 8 which monitors the blood pressure of a living subject and which also functions as an apparatus for measuring a propagation velocity of a pulse wave which is propagated through an artery of the subject.

Figure 1:
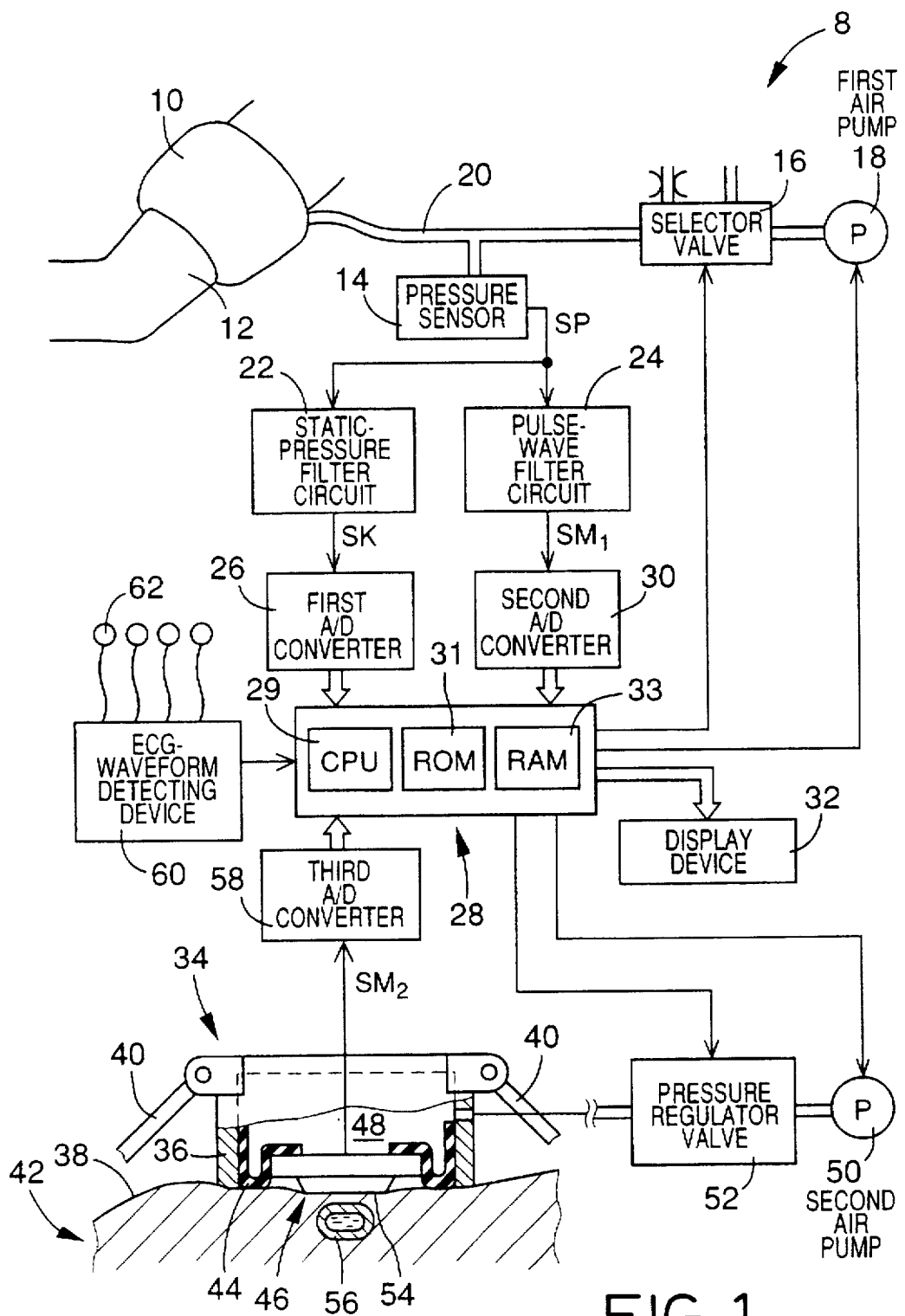
FIG. 1 is a diagrammatic view of a blood pressure (BP) monitor apparatus providing a pulse-wave propagation velocity measuring apparatus as a first embodiment of the present invention.

In FIG. 1, the BP monitor apparatus 8 includes a cuff 10 which has a belt-like cloth bag and a rubber bag accommodated in the cloth bag and which is adapted to be wound around, e.g., an upper arm 12 of a patient, and a pressure sensor 14, a selector valve 16, and a first air pump 18 each of which is connected to the cuff 10 via piping 20. The selector valve 16 is selectively placed in an inflation position in which the selector valve 16 permits a pressurized air to be supplied from the air pump 18 to the cuff 10, a slow-deflation position in which the selector valve 16 permits the pressurized air to be discharged slowly from the cuff 10, and a quick-deflation position in which the selector valve 16 permits the pressurized air to be discharged quickly from the cuff 10.

The pressure sensor 14 detects an air pressure in the cuff 10, and supplies a pressure signal, SP, representing the detected pressure to each of a static-pressure filter circuit 22 and a pulse-wave filter circuit 24. The static-pressure filter circuit 22 includes a low-pass filter and extracts, from the pressure signal SP, a static component contained in the signal SP, i.e., cuff-pressure signal, SK, representing the static cuff pressure. The cuff-pressure signal SK is supplied to an electronic control device 28 via a first A/D converter 26.

The pulse-wave filter circuit 24 includes a band-pass filter and extracts, from the pressure signal SP, an oscillatory component having frequencies in a predetermined range, i.e., cuff-pulse-wave (CPW) signal, $SM_1$. The CPW signal $SM_1$ is supplied to the control device 28 via a second A/D converter 30. The CPW signal $SM_1$ represents a cuff pulse wave, i.e., oscillatory pressure wave which is produced from a brachial artery (not shown) of the patient in synchronism with the heartbeat of the patient and is propagated to the cuff 10.

The electronic control device 28 is provided by a so-called microcomputer including a central processing unit (CPU) 29, a read only memory (ROM) 31, a random access memory (RAM) 33, and an input and output (I/O) port (not shown). The CPU 29 processes input signals according to the control programs pre-stored in the ROM 31 by utilizing the temporary-storage function of the RAM 33, and supplies drive signals via the I/O port to the selector valve 16 and the first air pump 18.

The BP monitor apparatus 8 further includes a pressure-pulse-wave detecting probe 34. The detecting probe 34 has a container-like housing 36 which is detachably worn, with the help of bands 40, on a body surface 38 of a wrist 42 downstream of an upper arm of the patient different from the upper arm 12 around which the cuff 10 is wound, or wrist downstream of the upper arm 12, such that an opening of the housing 36 is opposed to the body surface 38. A pressure-pulse-wave (PPW) sensor 46 is supported by the housing 36 via a diaphragm 44, such that the PPW sensor 46 is movable relative to the housing 36 and is advanceable through the opening of the housing 36. The housing 36, the diaphragm 44, and the PPW sensor 46 cooperate with one another to define a pressure chamber 48, to which a pressurized air is supplied from a second air pump 50 via a pressure regulator valve 52. Thus, the PPW sensor 46 is pressed against a radial artery 56 via the body surface or skin 38 with a pressing force, $P_{HD}$, corresponding to the air pressure in the pressure chamber 48.

The PPW sensor 46 includes a number of semiconductor pressure-sensing elements (not shown) which are arranged in a pressing surface 54 of a semiconductor chip formed of, e.g., monocrystalline silicon. The PPW sensor 46 is pressed against the radial artery 56 via the body surface 38 of the wrist 42 to detect a pressure pulse wave (PPW), i.e., oscillatory pressure wave which is produced from the radial artery 56 and is transmitted thereto via the body surface 38, and generates a pressure-pulse-wave (PPW) signal, $SM_2$, representing the detected PPW. The PPW signal $SM_2$ is supplied to the control device 28 via a third A/D convertor 58. In the present embodiment, the PPW sensor 46 provides a pulse-wave sensor which detects a pulse wave propagated through an artery of a living subject.

The CPU 29 of the control device 28 operates, according to the control programs pre-stored in the ROM 31, for supplying drive signals to the second air pump 50 and the pressure regulator value 52, and thereby regulating the air pressure in the pressure chamber 48, that is, pressing force $P_{HD}$ of the PPW sensor 46 applied to the radial artery 56 via the body surface 38. Based on respective magnitudes of heartbeat-synchronous pulses of the PPW detected through the PPW sensor 46 while the air pressure of the chamber 48 is changed, the CPU 29 determines an optimum pressing force, $P_{HDP}$, of the PPW sensor 46, in a known manner, and controls the pressure regulator valve 52 to maintain the optimum pressing force or pressure $P_{HDP}$, for each continuous BP monitoring operation.

The BP monitor apparatus 8 additionally includes an electrocardiographic-waveform (ECG-waveform) detecting device 60. The ECG-waveform detecting device 60 continuously detects an electrocardiographic (ECG) waveform indicating the time-wise change of electric potential of the cardiac muscle of a living subject, through a plurality of electrodes 62 which are placed at predetermined positions on the subject. The ECG-waveform detecting device 60 may be provided by an electrocardiograph, and the ECG waveform may be an electrocardiogram detected by the electrocardiograph. The ECG-waveform detecting device 60 supplies an electric signal representing the detected ECG waveform, to the electronic control device 28, so that the CPU 29 of the control device 28 processes the electric signal in a manner described later. A display device 32 may, not may not, record the ECG waveform on a recording sheet (not shown).

Figure 5:
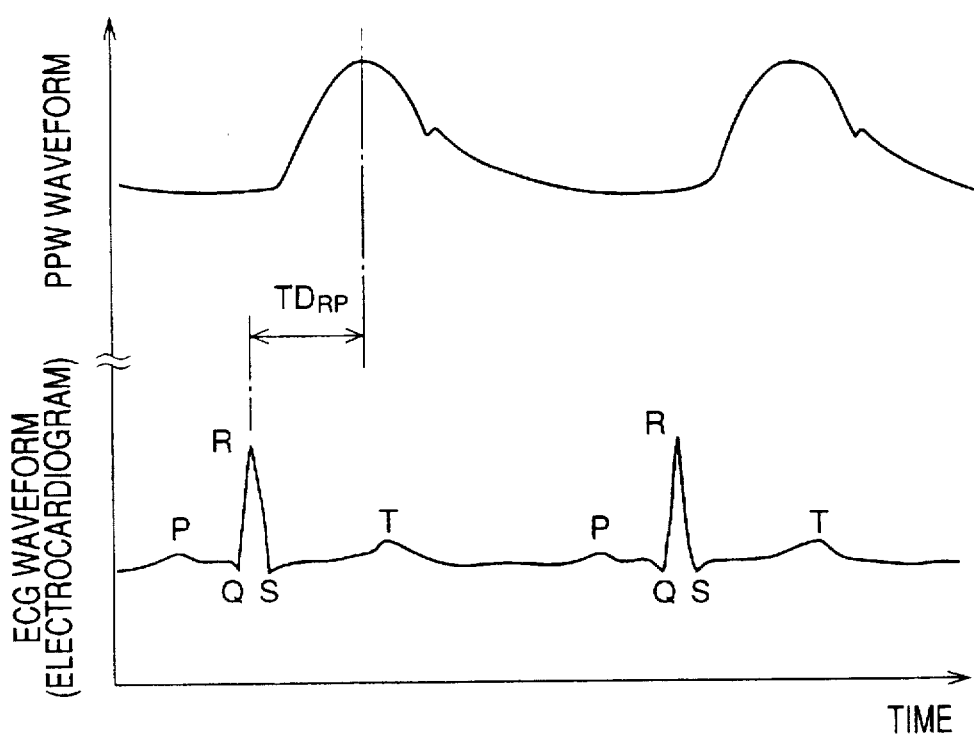
FIG. 5 is a time chart for illustrating a time difference, $TD_{RP}$, which is determined by the control device of the apparatus of FIG. 1.

In an upper and a lower portion of the graph of FIG. 5, a waveform as an example of a pressure pulse wave (PPW) detected by the PPW sensor 46, and an example (electrocardiogram) of an ECG waveform detected by the ECG-waveform detecting device 60 are shown, respectively.

Figure 2:
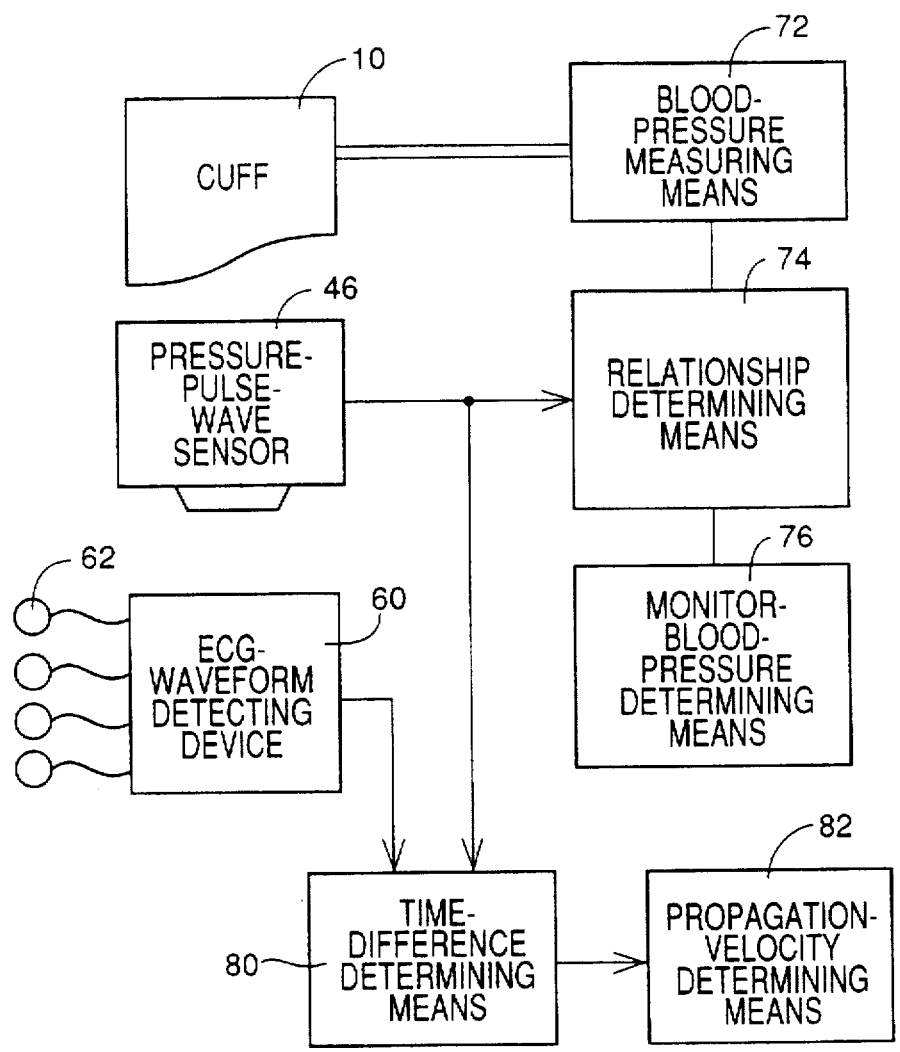
FIG. 2 is a block diagram for illustrating essential functions of an electronic control device of the apparatus of FIG. 1.

FIG. 2 illustrates essential control functions of the electronic control device 28 of the BP monitor apparatus 8. First, the control device 28 cooperates with the pressure sensor 14, the filter circuits 22, 24, and the A/D converters 26, 30 to function as a BP measuring means 72 which measures a systolic BP value, SBP, and a diastolic BP value, DBP, of the patient, according to a well-known oscillometric method (e.g., JIS T 1115; JIS is Japanese Industrial Standard), based on the variation of respective amplitudes of heartbeat-synchronous pulses of the cuff pressure wave (i.e., CPW signal $SM_1$) obtained through the pulse-wave filter circuit 24 while the pressure of the cuff 10 is slowly increased or decreased. The measured BP values are displayed on a screen of a cathode ray tube (CRT) of the display device 32.

The PPW sensor 46 is preferably pressed on the body surface 38 of the wrist 42 downstream of the upper arm different from the upper arm 12 on which the cuff 10 is worn, and detects a pressure pulse wave (PPW) produced from the radial artery 56 of the wrist 42. The control device 28 functions as a relationship determining means 74 which determines, in advance, a relationship between BP value (i.e., monitor BP value, MBP) and magnitude, $P_M$, of pressure pulse wave, based on at least one BP value measured by the BP measuring means 72 and at least one magnitude of the PPW (i.e., PPW signal $SM_2$) detected by the PPW sensor 46, for each patient and each BP monitoring operation. This relationship may be one, shown in FIG. 3, which is defined by the following linear function: MBP= $A \cdot P_M + B$, where A is a constant indicative of the slope of the linear function and B is a constant indicative of an intercept of the linear function. The control device 28 also functions as a monitor BP determining means 76 which successively determines, according to the relationship, a systolic and a diastolic BP value, $MBP_{SYS}$, $MBP_{DIA}$, (monitor BP values MBP), based on magnitudes $P_M$ of each heartbeat-synchronous pulse of the pressure pulse wave (i.e., PPW signal $SM_2$) detected by the PPW sensor 46, that is, maximum (upper-peak) and minimum (lower-peak) magnitudes, $P_{Mmax}$, $P_{Mmin}$, of each heartbeat-synchronous pulse of the pressure pulse wave, and successively outputs the determined monitor BP values MBP to the display device 32 so that the display device 32 successively displays the monitor BP values MBP for each heartbeat-synchronous pulse of the PPW.

The control device 28 also functions as a time-difference determining means 80 which determines a time difference between a predetermined periodic point relating to the ECG waveform of each of heartbeat-synchronous pulses of the electric signal supplied from the ECG-waveform detecting device 60, and a predetermined periodic point relating to the PPW waveform of a corresponding one of heartbeat-synchronous pulses of the PPW signal $SM_2$ supplied from the PPW sensor 46. For example, the determining means 80 determines a time difference, $TD_{RP}$, between the time of occurrence or detection of an R wave of each pulse of the ECG waveform and the time of occurrence or detection of a maximum (upper-peak) point of a corresponding pulse of the PPW waveform, as shown in FIG. 5. The maximum or upper-peak point has a maximum magnitude, i.e., maximum electric voltage.

The control device 28 additionally functions as a propagation-velocity determining means 82 which determines a propagation velocity, $V_M$, (m/sec) of the pressure pulse wave (PPW) which is propagated through the artery of the patient including the radial artery 56, based on the determined time difference $TD_{RP}$, according to the following expression (1) pre-stored in the ROM 31:

$$V_M = L/(TD_{RP} - T_{PEP}) \quad (1)$$

where

L is the length of the artery of the patient from the left ventricle to the position of pressing of the PPW sensor 46 via the aorta, brachial artery, and radial artery 56; and $T_{PEP}$ is the pre-ejection period between a Q wave or point of the ECG waveform and a minimum point (i.e., rising point) of the PPW waveform.

The values L, $T_{PEP}$ occurring in the expression (1) are experimentally determined, in advance.

Next, there will be described the operation of the BP monitor apparatus 8 constructed as described above, by reference to the flow chart of FIG. 4.

First, at Step SA1, the CPU 29 of the control device 28 reads in one heartbeat-synchronous pulse of the ECG waveform detected by the ECG-waveform detecting device 60 and, at Step SA2, the CPU 29 reads in a corresponding heartbeat-synchronous pulse of the PPW waveform detected by the PPW sensor 46.

Subsequently, at Step SA3, the CPU 29 judges whether the CPU 29 has read in an R wave (or R point) of the heartbeat-synchronous pulse of the ECG waveform. If a negative judgment is made at Step SA3, the control of the CPU 29 goes back to Step SA1. Meanwhile, if a positive judgment is made at Step SA3, the control of the CPU 29 goes to Step SA4 to judge whether the CPU 29 has read in a maximum point of the corresponding heartbeat-synchronous pulse of the PPW waveform.

If a negative judgment is made at Step SA4, the control of the CPU 29 goes back to Step SA1. Meanwhile, if a positive judgment is made at Step SA4, the control of the CPU 29 goes to Step SA5 to determine a time difference $TD_{RP}$ from the R wave of one pulse of the ECG waveform to the maximum point of corresponding pulse of the PPW waveform, as shown in FIG. 5. Step SA5 corresponds to the time-difference determining means 80. Step SA5 is followed by Step SA6 to determine a propagation velocity $V_M$ of PPW, based on the time difference $TD_{RP}$ determined at Step SA5, according to the above expression (1). Step SA6 corresponds to the propagation-velocity determining means 82. The PPW propagation velocity $V_M$ determined at Step SA6 may be used to estimate a degree of arterial sclerosis, a peripheral resistance, or a BP value of the patient according to an algorithm (not shown). The thus estimated BP value may be utilized by the relationship determining means 74 when the means 74 operates for updating the $MBP$-$P_M$ relationship shown in FIG. 3.

As is apparent from the foregoing description, in the first embodiment shown in FIGS. 1 to 5, the CPU 29 of the control device 28 determines, at Step SA5, the time difference $TD_{RP}$ between the predetermined periodic point (R wave) of each heartbeat-synchronous pulse of the ECG waveform and the predetermined periodic point (maximum point) of a corresponding heartbeat-synchronous pulse of the PPW waveform and determines, at Step SA6, the velocity $V_M$ of propagation of the PPW through the artery of the patient, based on the time difference $TD_{RP}$ determined at Step SA5, according to the above expression (1). This propagation velocity $V_M$ is calculated based on the greatest length L of patient's artery including the aorta directly connected to patient's heart. In addition, since the aorta has the greatest diameter, the velocity $V_M$ of propagation of the PPW becomes the lowest when the PPW passes through the aorta. That is, it needs a long time for the PPW to pass through the aorta. Thus, the time difference $TD_{RP}$ is maximized. Therefore, the present BP monitor apparatus 8, i.e., pulse-wave propagation velocity measuring apparatus 8 measures the propagation velocity $V_M$ of the PPW with higher accuracy than the prior apparatus which measures a propagation velocity of a pulse wave based on a smaller time difference. In addition, the propagation velocity $V_M$ may be relied upon for estimating, with higher accuracy, a degree of arterial sclerosis and/or a BP value of the patient.

Figure 3:
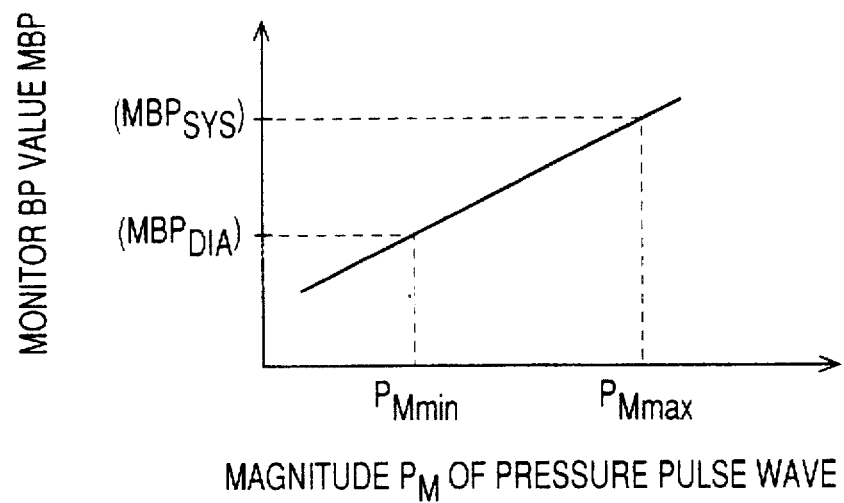
FIG. 3 is a graph showing a relationship which is determined by the control device of the apparatus of FIG. 1.
Figure 4:
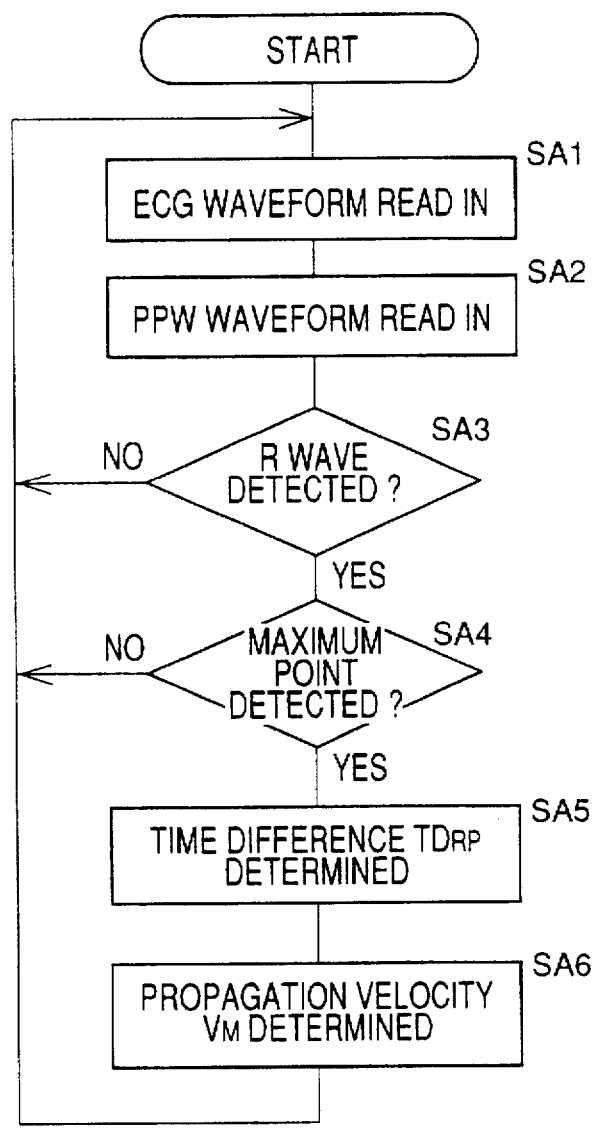
FIG. 4 is a flow chart representing a control program according to which the apparatus of FIG. 1 is controlled.

In addition, in the first embodiment, the PPW sensor 46 is used for the two purposes, i.e., one for detecting, from the radial artery 56, the magnitudes $P_M$ of each pulse of the PPW which are used by the monitor BP determining means 76 for successively determining the monitor BP values MBP according to the relationship shown in FIG. 3 and the other for detecting the time of occurrence of the maximum point of each pulse of the PPW which is used by the time-difference determining means 80 for determining the time difference $TD_{RP}$. Accordingly, the total number of elements or parts of the present apparatus 8 is decreased and the production cost of the same 8 is reduced.

Figure 6:
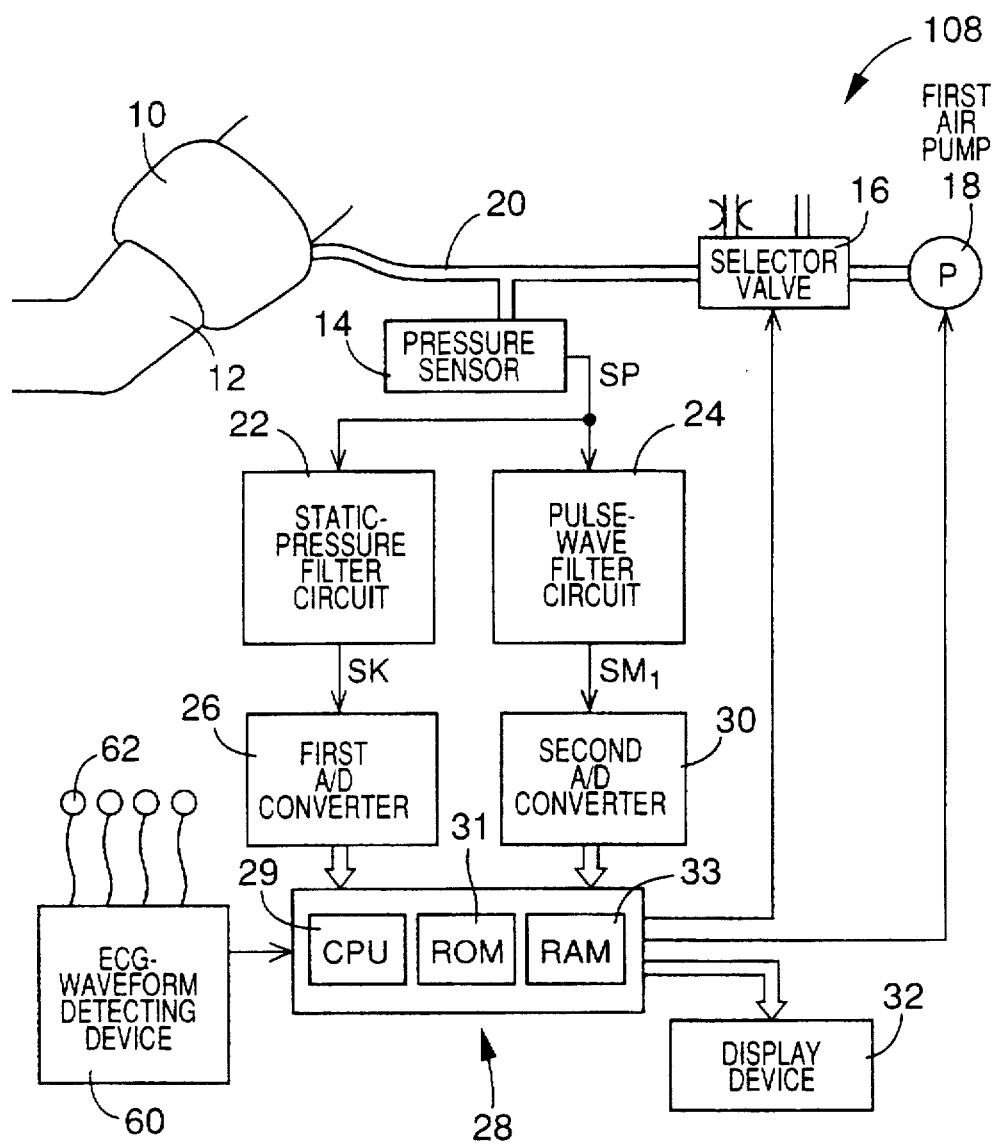
FIG. 6 is a diagrammatic view corresponding to FIG. 1, showing a BP measuring apparatus providing another pulse-wave propagation velocity measuring apparatus as a second embodiment of the present invention.
Figure 7:
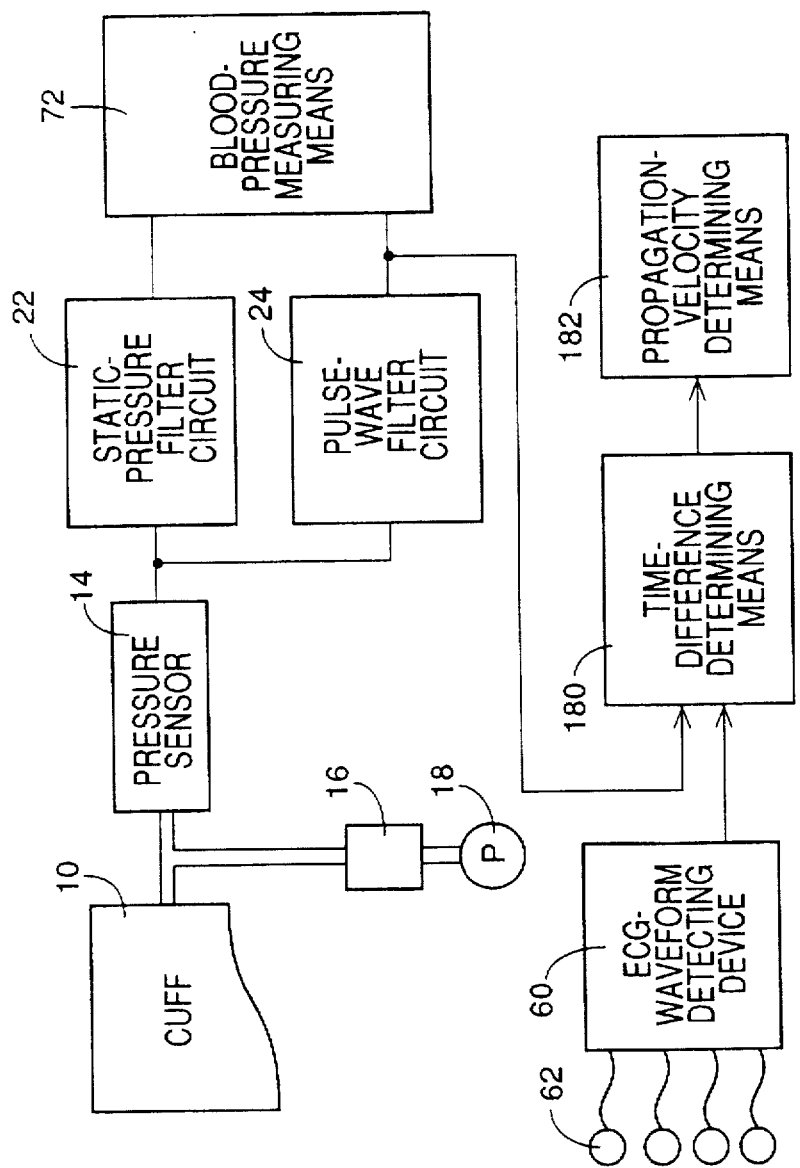
FIG. 7 is a block diagram corresponding to FIG. 2, for illustrating essential functions of an electronic control device of the apparatus of FIG. 6.

Referring next to FIGS. 6 and 7, there will be described a second embodiment of the present invention. The second embodiment relates to a blood pressure (BP) measuring apparatus 108 which has basically the same hardware construction as that of the BP monitor apparatus 108 shown in FIGS. 1 and 2 but does not include the PPW detecting probe 34, the third A/D converter 58, the second air pump 50, or the pressure regulator valve 52. The same reference numerals as used in FIGS. 1 and 2 are used to designate the corresponding elements or parts of the BP measuring apparatus 108 shown in FIGS. 6 and 7, and the description thereof is omitted.

In the second embodiment, a cuff 10, a pressure sensor 14, a pulse-wave filter circuit 24, etc. cooperate with one another to provide a pulse-wave sensor which detects a pulse wave propagated through an artery of a patient. The pulse-wave sensor 10, 14, 24 detects, as the pulse wave, a cuff pulse wave (CPW) which is propagated through a brachial artery of an upper arm 12 of the patient and transmitted to the cuff 10, and supplies a cuff-pulse-wave (CPW) signal, $SM_1$, representing the detected CPW waveform, to an electronic control device 28 via a second A/D converter 30. An example of the CPW waveform is shown in an upper portion of the graph of FIG. 12.

As shown in FIG. 7, the control device 28 functions as a time-difference determining means 180 which determines a time difference, $TD_{RP}$, between an R wave of each heartbeat-synchronous pulse of an ECG waveform detected by an ECG-waveform detecting device 60 and a maximum (upper-peak) point of a corresponding heartbeat-synchronous pulse of the cuff pulse wave (i.e., CPW signal $SM_1$) detected by the pulse-wave sensor 10, 14, 24. The control device 28 also functions as a propagation-velocity determining means 182 which determines a velocity, $V_{MCPW}$, of the CPW propagated through patient's artery including the brachial artery, based on the time difference $TD_{RP}$ determined by the time-difference determining means 180, according to the same expression as the previously-indicated expression (1).

Like the propagation velocity $V_M$ determined by the BP monitor apparatus 8, the propagation velocity $V_{MCPW}$ is determined based on the great length L of patient's artery including the aorta directly connected to patient's heart. In addition, since the aorta has the great diameter, the velocity $V_{MCPW}$ of propagation of the CPW becomes very low when the CPW passes through the aorta. That is, it needs a long time for the CPW to pass through the aorta. Thus, the time difference $TD_{RP}$ is maximized. Therefore, the present BP measuring apparatus 108, i.e., pulse-wave propagation velocity measuring apparatus 108 measures the propagation velocity $V_{MCPW}$ of the CPW with higher accuracy than the prior apparatus which measures a propagation velocity of a pulse wave based on a small time difference. In addition, the propagation velocity $V_{MCPW}$ can be relied upon for estimating, with higher accuracy, a degree of arterial sclerosis and/or a BP value of the patient.

In the second embodiment shown in FIGS. 6 and 7, the pulse-wave sensor, i.e., cuff 10, pressure sensor 14, pulse-wave filter circuit 24, etc. are used for the two purposes, i.e., one for cooperating with a BP measuring means 72 to measure a systolic and a diastolic BP value of the patient and the other for detecting the time of occurrence of the maximum point of each pulse of the CPW which is used by the time-difference determining means 180 for determining the time difference $TD_{RP}$. Accordingly, the total number of elements or parts of the present apparatus 108 is decreased and the production cost of the same 108 is reduced.

In each of the first and second embodiments, the time difference $TD_{RP}$ is calculated as the difference of the time of occurrence of R wave of each pulse of the ECG waveform and the time of occurrence of maximum point of a corresponding pulse of the PPW or CPW. However, it is possible to determine a time difference, TD, between a Q wave or a S wave of each pulse of the ECG waveform and a maximum or a minimum (lower-peak) point of a corresponding pulse of the PPW or CPW, or between the R wave of each pulse of the ECG waveform and the minimum point of a corresponding pulse of the PPW or CPW. The propagation velocity $V_M$, $V_{MCPW}$ may be determined based on the time difference TD according to the expression (1).

Figure 17:
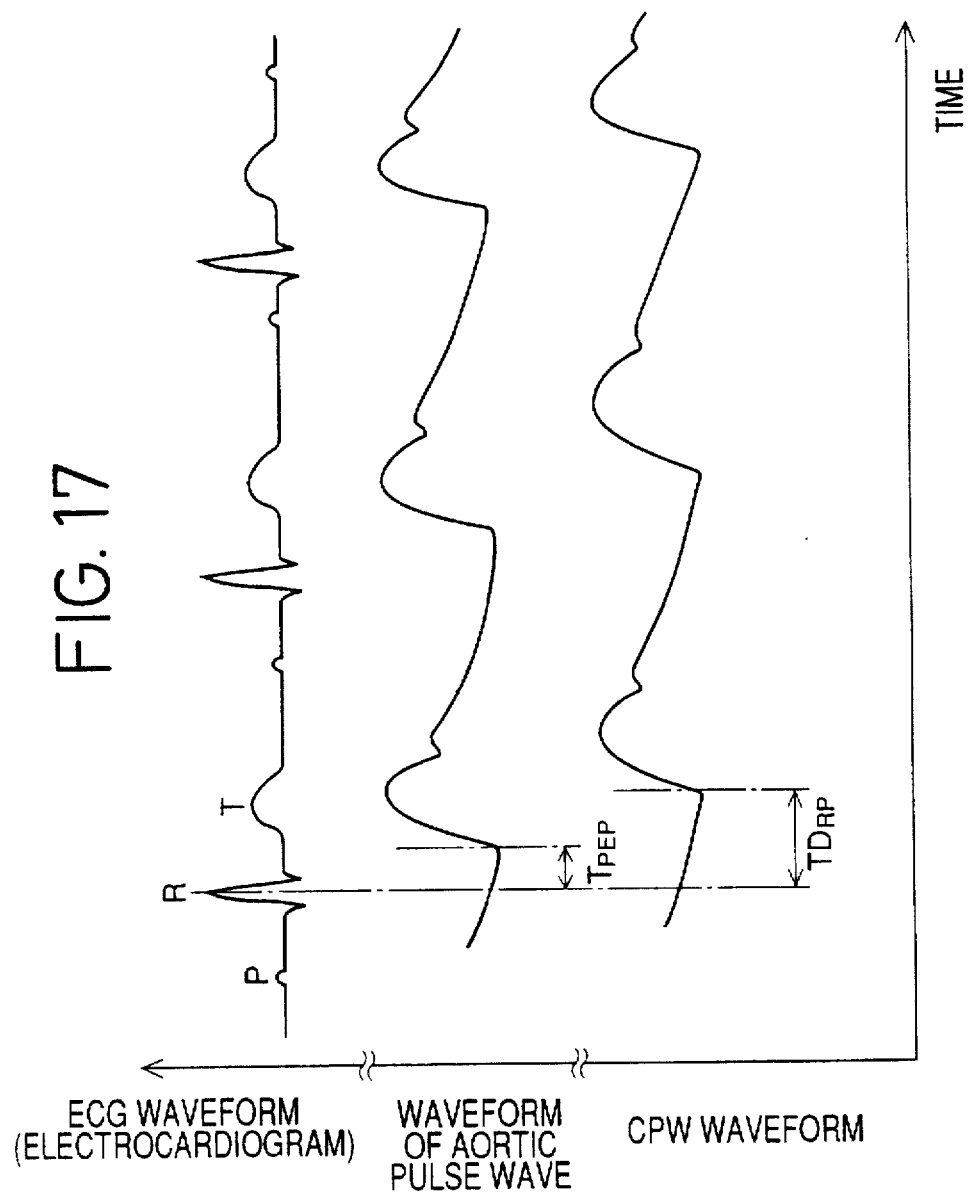
FIG. 17 is a time chart for illustrating a time difference, $TD_{RP}$, which is determined by the control device of the apparatus of FIG. 15.

In the expression (1) employed in each of the first and second embodiments, the pre-ejection period $T_{PEP}$ is defined as the difference of the time of occurrence of Q wave (Q point) of each pulse of the ECG waveform and the time of occurrence of minimum point (rising point) of a corresponding pulse of the PPW or CPW. However, it is possible to define the pre-ejection period $T_{PEP}$ as a time difference between the R wave (R point) or S wave (S point) of each pulse of the ECG waveform and the minimum point of a corresponding pulse of the PPW or CPW, because the Q, R, and S waves of each pulse are very near to one another in time on the ECG waveform. Alternatively, it is possible to define the pre-ejection period $T_{PEP}$ as a time difference between a periodic point relating to each pulse of the ECG waveform and a periodic point relating to a corresponding pulse of an aortic pulse wave, as shown in FIG. 17. In the last case, too, the value $T_{PEP}$ may be experimentally determined and stored in the ROM 31, in advance.

In each of the first and second embodiments, the pressure pulse wave (PPW) or the cuff pulse wave (CPW) is detected as the pulse wave of the patient. However, the pulse-wave sensor may be provided by a known photoelectric sensor including a light source which emits a light toward a body surface or skin tissue of a patient, and a light detecting element which detects the light transmitted through, or reflected from, the skin tissue of the patient and produces an electric signal representing, as a photoelectric pulse wave, the time-wise change of intensity of the detected light. The intensity of the light transmitted through, or reflected from, the skin tissue changes as the volume of blood flowing through the artery running in the skin tissue changes in synchronism with the heartbeat of the patient. For example, a so-called pulse oximeter that measures a blood oxygen saturation of a living subject includes a photoelectric sensor including a light source which emits two lights having different wavelengths, respectively, toward skin tissue of the subject and a light detecting element which detects the two lights each transmitted through, or reflected from, the skin tissue. The pulse oximeter determines a blood oxygen saturation of the subject based on the detected lights. In the latter case, the photoelectric sensor is used for the two purposes, i.e., one for detecting the two lights which are utilized for determining the blood oxygen saturation of the patient and the other for detecting the time of occurrence of a periodic point of each pulse of the photoelectric pulse wave which is utilized for determining a time difference TD based on the time of occurrence of the periodic point. Accordingly, the total number of elements or parts of the pulse oximeter is decreased and the production cost of the same is reduced, like the apparatus 8, 108.

Referring next to FIGS. 8 to 14, there will be described a third embodiment of the present invention which relates to an automatic blood pressure (BP) measuring apparatus 208 which automatically measures a BP value of a living subject and which also functions as an apparatus for measuring a propagation velocity of a pulse wave which is propagated through an artery of the subject.

Figure 8:
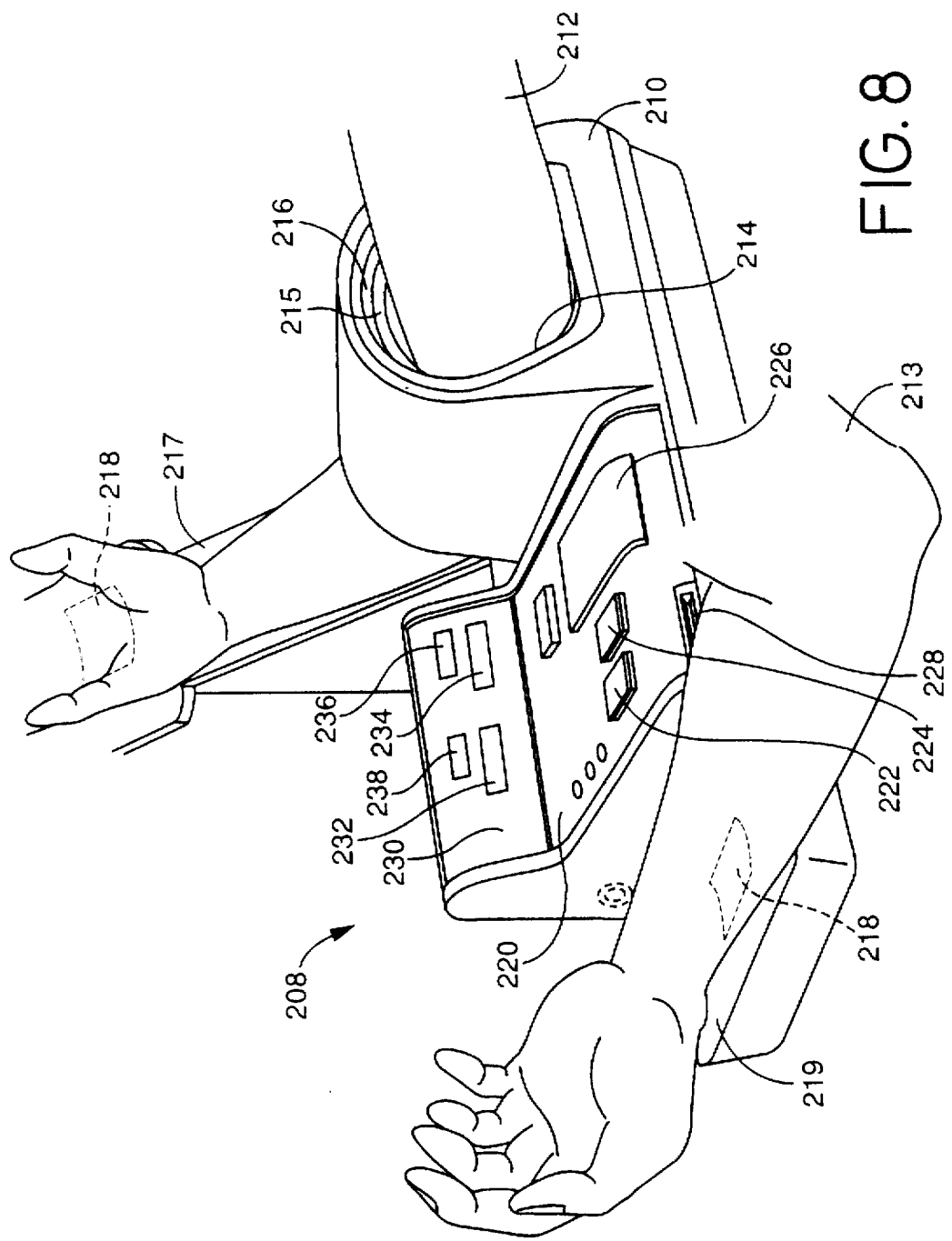
FIG. 8 is a perspective view of a BP measuring apparatus providing another pulse-wave propagation velocity measuring apparatus as a third embodiment of the present invention.

In FIG. 8, reference numeral 210 designates a housing of the BP measuring apparatus 208. The housing 210 includes a tunnel-like, cylindrical hollow portion which provides an arm receiver 214 into which a right arm 212 of the subject is inserted for measurement of his or her BP value or values. Inside the arm receiver 214, an elongate belt 216 is supported such that the belt 216 takes a generally cylindrical shape. An inflatable cuff 215 which is provided by a flexible cloth bag and a rubber bag accommodated in the cloth bag, is secured to the inner surface of the elongate belt 216.

In rear of the arm receiver 214, a first arm rest 217 is provided at a tilt to support the forearm of the right arm 212. A first electrode 218 of an electrocardiographic-waveform detecting device 270 (FIG. 9) is provided on an end portion of the arm rest 217 such that the electrode 218 contacts the back of the hand of the right arm 212. The upper surface of the arm rest 217 has a shape suitable for supporting the entire forearm of the arm 212 such that the muscles between the elbow and the back of the hand are kept relaxed for detecting an accurate electrocardiographic waveform. A second arm rest 219 is provided on the left-hand side of the housing 210, for supporting a left arm 13 of the subject, and a second electrode 218 is provided on a middle portion of the arm rest 219 such that the second electrode 18 contacts the left arm 13. The two electrodes 18 cooperate with each other to detect the electrocardiographic waveform from the subject. Like the first arm rest 217, the upper surface of the second arm rest 219 has a shape suitable for supporting the entire forearm of the left arm 213 such that the muscles between the elbow and the back of the hand are kept relaxed for detecting an accurate electrocardiographic waveform.

The BP measuring apparatus 208 has an operation panel 220 including a START switch 222, a STOP switch 224, a printer 226, and a card insertion slot 228. The BP measuring apparatus 208 further has a display panel 230 including a SBP display 232, a DBP display 234, a HR display 236, and a date and time display 238. The abbreviations "SBP", "DBP", and "HR" represent a systolic BP value, a diastolic BP value, and a heart-rate or pulse-rate value, respectively.

Figure 9:
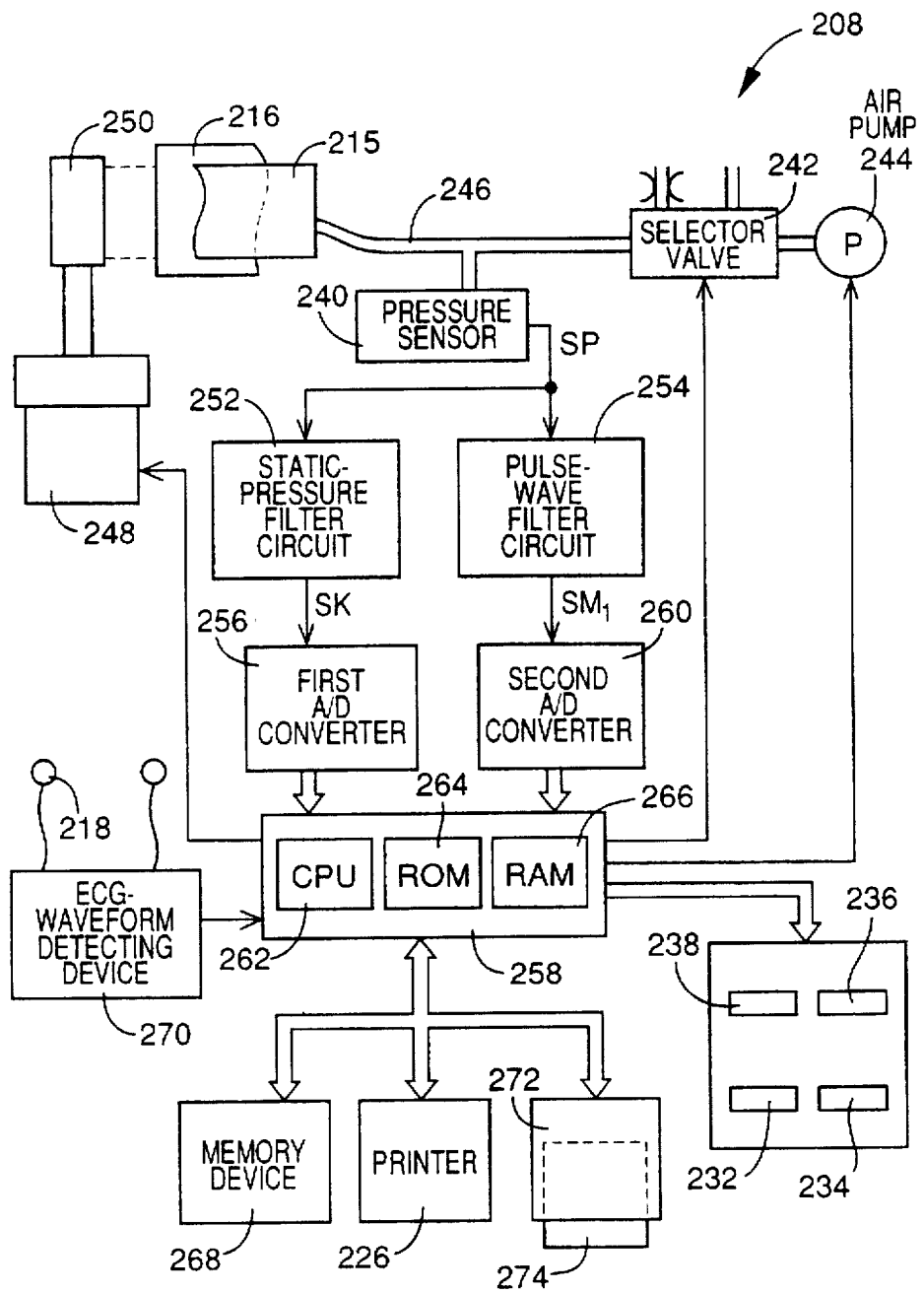
FIG. 9 is a diagrammatic view corresponding to FIG. 1, for showing the construction of of the apparatus of FIG. 8.

FIG. 9 shows the construction of the BP measuring apparatus 208. In the figure, the inflatable cuff 215 is connected via piping 246 to a pressure sensor 240, a selector valve 242, and an air pump 244. The selector valve 242 is selectively placed in an inflation position in which the selector valve 242 permits a pressurized air to be supplied from the air pump 244 to the cuff 215, a slow-deflation position in which the selector valve 242 permits the pressurized air to be discharged slowly from the cuff 215, and a quick-deflation position in which the selector valve 242 permits the pressurized air to be discharged quickly from the cuff 215. The elongate belt 216 which takes a cylindrical shape in the arm receiver 214 and to which the inflatable cuff 215 is secured, is fixed at one of longitudinal ends thereof to the housing 210 and is connected at the other longitudinal end to a rotatable drum 250 which is driven or rotated by a direct-current (DC) motor 248 via reduction gears. The elongate belt 216 or the inflatable cuff 215 is tightened, and loosened, by the DC motor 248.

The pressure sensor 214 detects an air pressure in the cuff 215, and supplies a pressure signal, SP, representing the detected pressure to each of a static-pressure filter circuit 252 and a pulse-wave filter circuit 254. The static-pressure filter circuit 252 includes a low-pass filter and extracts, from the pressure signal SP, a static component contained in the signal SP, i.e., cuff-pressure signal, SK, representing the static cuff pressure. The cuff-pressure signal SK is supplied to an electronic control device 258 via a first A/D converter 256.

The pulse-wave filter circuit 254 includes a band-pass filter and extracts, from the pressure signal SP, an oscillatory component having frequencies in a predetermined range, i.e., cuff-pulse-wave (CPW) signal, $SM_1$. The CPW signal $SM_1$ is supplied to the control device 258 via a second A/D converter 260. The CPW signal $SM_1$ represents a cuff pulse wave, i.e., oscillatory pressure wave which is produced from a brachial artery (not shown) of the subject in synchronism with the heartbeat of the subject and is propagated to the cuff 215. In the present embodiment, the cuff 215, pressure sensor 240, pulse-wave filter circuit 254, etc. cooperate with one another to provide a pulse-wave sensor which detects a pulse wave propagated through an artery of a living subject.

The electronic control device 258 is provided by a so-called microcomputer including a central processing unit (CPU) 262, a read only memory (ROM) 264, a random access memory (RAM) 266, and an input and output (I/O) port (not shown). The CPU 262 processes input signals according to the control programs pre-stored in the ROM 264 by utilizing the temporary-storage function of the RAM 266, outputs a drive signal to the printer 226, and outputs display signals to the displays 232–238. When a BP measurement is carried out, the CPU 262 supplies a drive signal to the DC motor 248 to wind the cuff 215 around the right arm 212 of the subject being inserted in the arm receiver 214, subsequently supplies a drive signal to the air pump 244 to inflate the cuff 215 and thereby press the upper arm 212, and then supplies a drive signal to the selector valve 242 to reduce gradually or slowly the pressure of the cuff 215, so that the CPU 262 obtains the pulse-wave signal $SM_1$ and the cuff-pressure signal SK from the pressure sensor 240 via the respective filters 252, 254 during this cuff-pressure reducing operation, determines a systolic and a diastolic BP value SBP, DBP of the subject according to a known oscillometric BP measuring method based on the obtained signals SM, SK, and supplies display signals to the SBP and DBP displays 232, 234 to display the determined BP values SBP, DBP, respectively.

In addition, the CPU 262 produces a set of BP data which represents the thus determined BP values SBP, DBP and a date and a time when those BP values are obtained, and stores the set of BP data in a BP-data storing area of a memory device 268. The memory device 268 accumulatively stores a plurality of sets of BP data produced in a plurality of BP measuring operations. The memory device 268 may be provided by a well-known data storing device such as a magnetic disk, a magnetic tape, a volatile semiconductor memory, or a non-volatile semiconductor memory.

Figure 13:
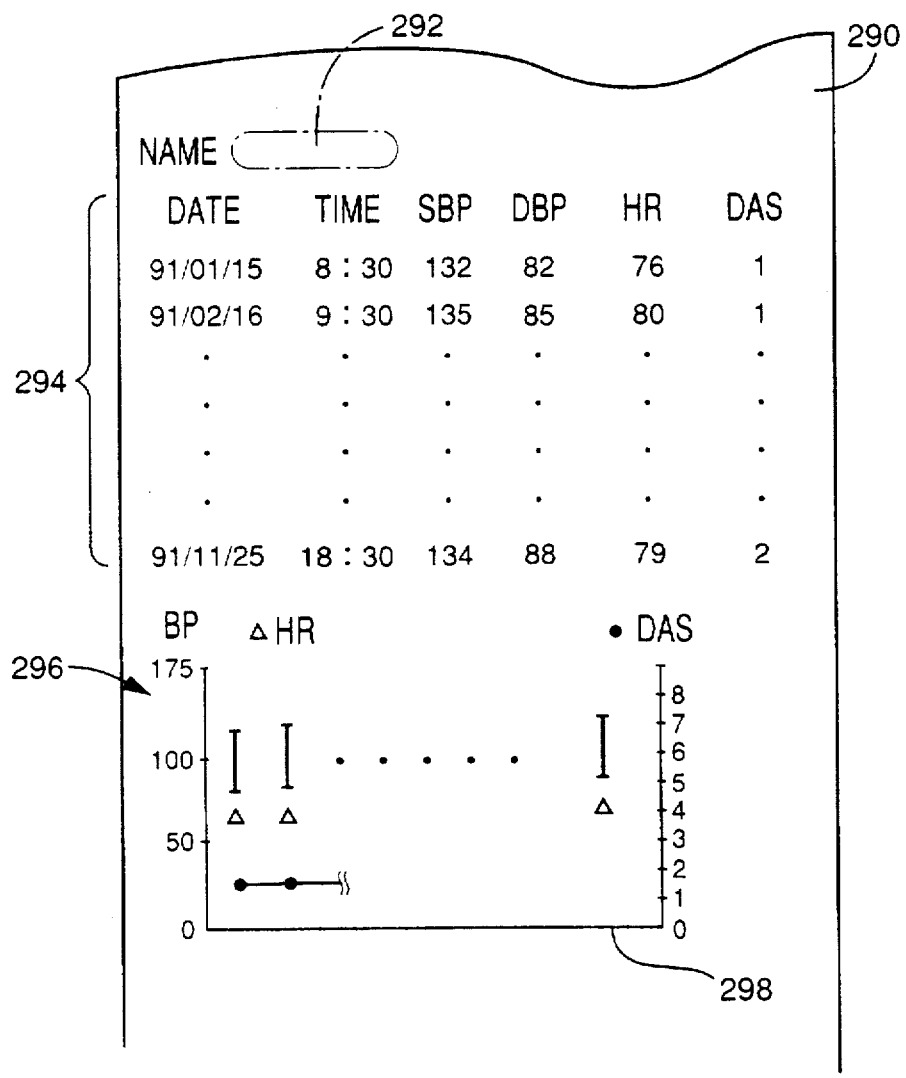
FIG. 13 is a view of a printed sheet output from a printer of the apparatus of FIG. 8.

The BP measuring apparatus 208 includes the electrocardiographic-waveform (ECG-waveform) detecting device 270. The ECG-waveform detecting device 270 continuously detects an electrocardiographic (ECG) waveform indicating the change of electric potential of the cardiac muscle of the subject, through the pair of electrodes 218 one of which contacts the back of the right hand 212 of the subject and the other of which contacts the left arm 213 of the same. The ECG-waveform detecting device 270 may be provided by an electrocardiograph, and the ECG waveform may be an electrocardiogram detected by the electrocardiograph. The detecting device 270 supplies an electric signal representing the detected ECG waveform, to the control device 258, so that the CPU 262 of the control device 258 processes the electric signal. The printer 226 may, not may not, print out the ECG waveform on a recording sheet 290 (FIG. 13).

Figure 12:
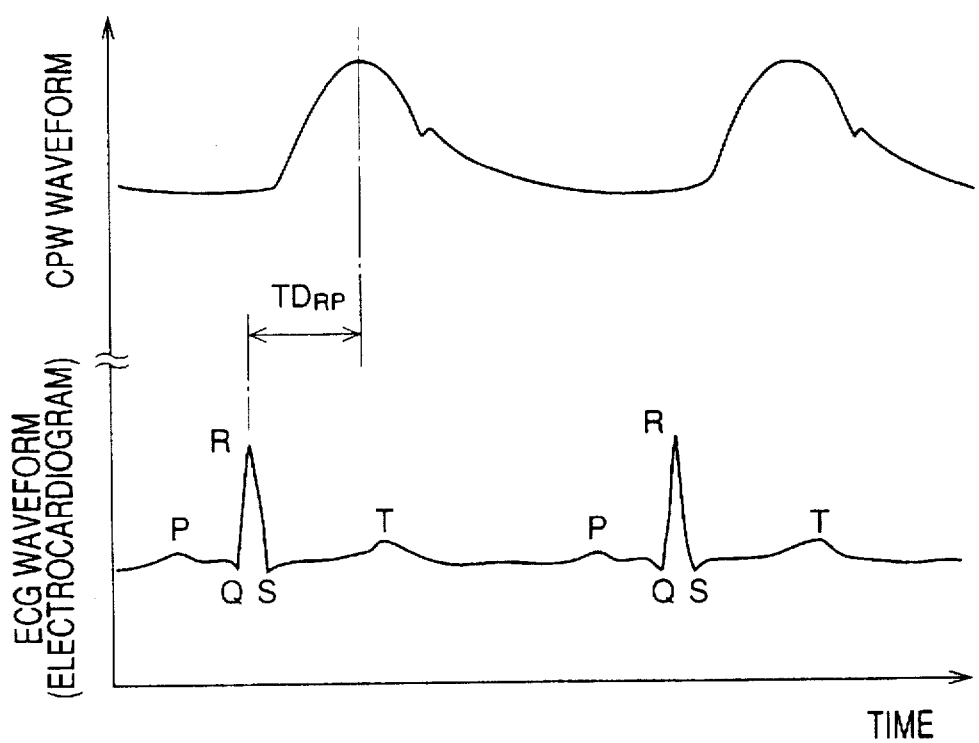
FIG. 12 is a time chart for illustrating a time difference, $TD_{RP}$, which is determined by the control device of the apparatus of FIG. 8.

In an upper and a lower portion of the graph of FIG. 12, a waveform as an example of a cuff pulse wave (CPW) detected by the pulse-wave sensor 215, 240, 254, and an example (electrocardiogram) of an ECG waveform detected by the ECG-waveform detecting device 270 are shown, respectively.

Figure 10:
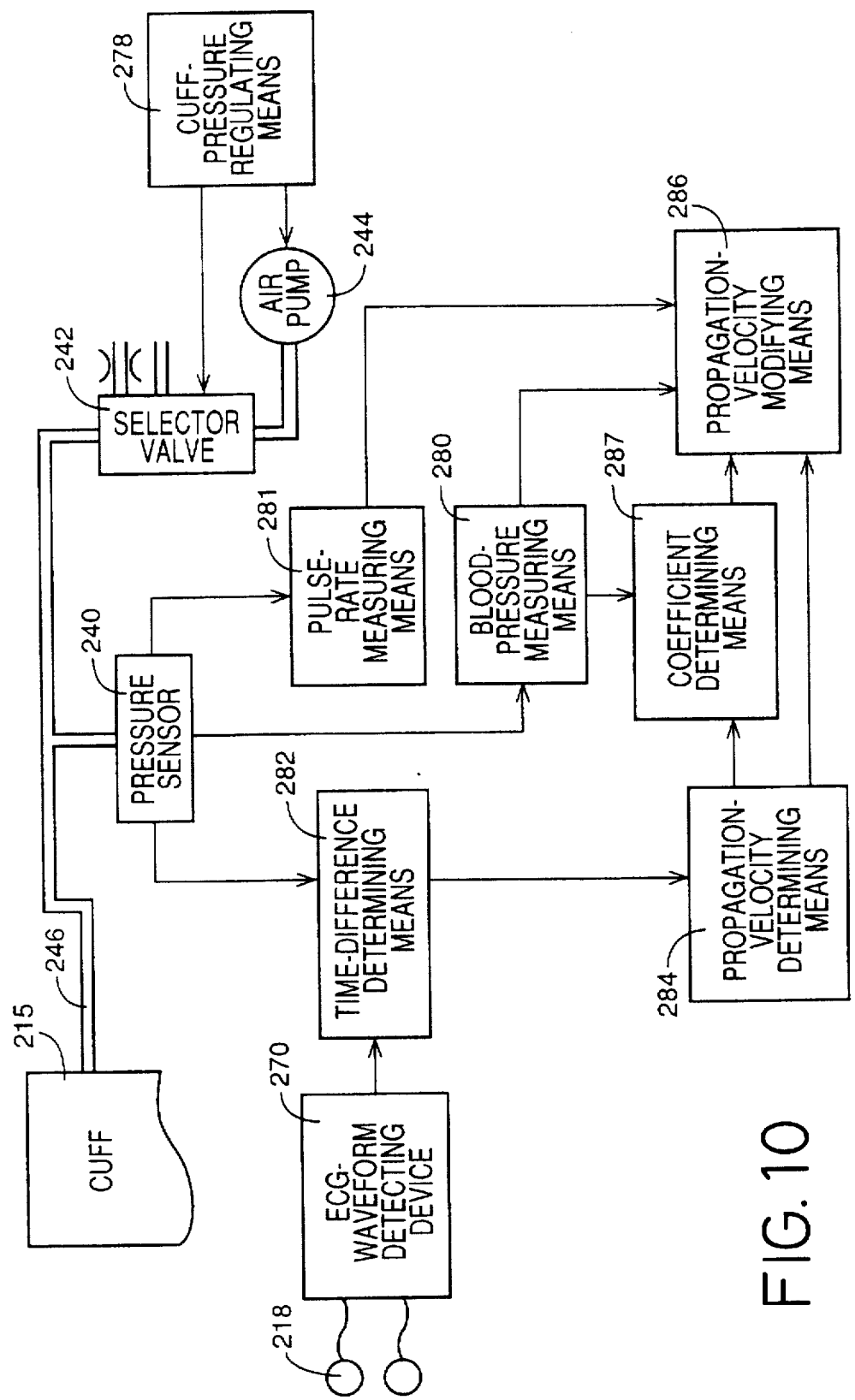
FIG. 10 is a block diagram corresponding to FIG. 2, for illustrating essential functions of an electronic control device of the apparatus of FIG. 8.

FIG. 10 illustrates essential control functions of the electronic control device 258 of the BP measuring apparatus 208. First, the control device 258 functions as a cuff-pressure regulating means 278 which switches the selector valve 242 to the inflation position and drives the air pump 244, so as to increase quickly the pressure of the cuff 215 up to a predetermined target value, $P_1$, (e.g., 180 mmHg), subsequently switches the valve 242 to the slow-deflation position so as to decrease slowly the cuff pressure and, after a BP measurement, switches the valve 242 to the quick-deflation position so as to decrease quickly the cuff pressure. In addition, the control device 258 functions as a BP measuring means 280 which cooperates with the cuff 215, the pressure sensor 240, etc. to measure a systolic BP value SBP and a diastolic BP value DBP of the subject, according to a well-known oscillometric method, based on the variation of respective amplitudes of heartbeat-synchronous pulses of the cuff pressure wave (i.e., CPW signal $SM_1$) obtained through the pulse-wave filter circuit 254 while the pressure of the cuff 215 is slowly decreased. The control device 258 additionally functions as a pulse-rate measuring means 281 which cooperates with the cuff 215, the pressure sensor 240, etc. to measure a pulse-rate value HR of the subject from the interval of successive two heartbeat-synchronous pulses of the CPW.

The control device 258 also functions as a time-difference determining means 282 which determines a time difference between a predetermined periodic point relating to the ECG waveform of each of heartbeat-synchronous pulses of the electric signal supplied from the ECG-waveform detecting device 270, and a predetermined periodic point relating to the waveform of a corresponding one of heartbeat-synchronous pulses of the CPW signal $SM_1$ which is supplied from the pressure sensor 240 when the pressure of the cuff 215 is around the diastolic BP value DBP of the subject. For example, the determining means 282 determines a time difference, $TD_{RP}$, between the time of occurrence or detection of an R wave of each pulse of the ECG waveform and the time of occurrence or detection of a maximum point (upper-peak point) of a corresponding pulse of the CPW waveform, as shown in FIG. 12.

The control device 258 additionally functions as a propagation-velocity determining means 284 which determines a propagation velocity, $V_{M1}$, (m/sec) of the cuff pulse wave (CPW) which is propagated through the artery of the subject including the brachial artery of the right arm 212, based on the determined time difference $TD_{RP}$, according to a predetermined expression (2):

$$V_{M1} = L/(TD_{RP} - T_{PEP}) \qquad (2)$$

where

L is the length (m) of the artery of the subject from the left ventricle to the position of pressing of the cuff 215 via the aorta and the brachial artery; and $T_{PEP}$ is the pre-ejection period between a Q wave or point of the ECG waveform and a minimum point (i.e., rising point) of the CPW waveform.

The values L, $T_{PEP}$ occurring in the expression (2) are experimentally determined, in advance. The expression (2) is pre-stored in the ROM 264.

The control device 258 also functions as a propagation-velocity modifying means 286 which modifies the propagation velocity $V_{M1}$ determined by the propagation-velocity determining means 284, to a modified propagation velocity, $V_{M2}$, (m/sec) corresponding to a predetermined BP value, $BP_r$, and a predetermined pulse rate, $HR_r$, based on the diastolic BP value DBP measured by the BP measuring means 280 and the pulse rate HR measured by the pulse-rate measuring means 281, according to a predetermined expression (3):

$$V_{M2} = V_{M1} + A(BP_r - DBP) + E(HR_r - HR) \qquad (3)$$

where $$A = B \cdot V_{M1} + C \cdot DBP + D \qquad (4);$$

and

B, C, D, and E are constants.

The coefficient, A, occurring in the expression (3) is determined by a coefficient determining means 287 according to the above expression (4). The coefficient A increases as the propagation velocity $V_{M1}$ increases, and decreases as the diastolic BP value DBP increases. The control device 258 functions as the coefficient determining means 288. The constant E occurring in the expression (3) and the constants B, C, D occurring in the expression (4) are experimentally pre-determined. The constant B is positive and the constant C is negative.

Hereinafter, there will be described the operation of the BP measuring apparatus 208 constructed as described above, by reference to the flow chart of FIG. 11.

First, at Step SA201, the CPU 262 judges whether a magnetic card 274 has been inserted in a card reader 272 through the insertion slot 228 by a living person. If a negative judgment is made at Step SA201, the current cycle of this routine is ended. On the other hand, if a positive judgment is made at Step SA201, the control of the CPU 262 goes to Step SA202 to read identification (ID) data which are magnetically recorded on the magnetic card 274 and which identify the person who carries the card 274.

Step SA202 is followed by Step SA203 to judge whether the ID data read from the magnetic card 274 are identical with ID data registered in an ID-data storing area of the memory device 268. The ID-data storing area has the memory capacity to store a number of sets of ID data corresponding to a number of magnetic cards 274, i.e., a number of living persons. If a negative judgment is made at Step SA203, the control of the CPU 262 goes to Step SA222 to eject the card 274 from the card reader 272 through the slot 228. On the other hand, if a positive judgment is made at Step SA203, i.e., the ID data read from the card 274 are identical with registered ID data, the control of the CPU 262 goes to Step SA204 to judge whether the START switch 222 has been operated to start a blood pressure (BP) measurement.

If the judgment made at Step SA204 is negative, Step SA204 is repeated until a positive judgment is made. Meanwhile, if a positive judgment is made at Step SA204, the control of the CPU 262 goes to Step SA205 to switch the selector valve 242 to the inflation position thereof and drive the air pump 244 so as to increase the pressure, P, of the cuff 215 up to a predetermined target value (e.g., 180 mmHg) and subsequently stop the air pump 244. Step SA205 is followed by Step SA206 to switch the valve 242 to the slow-deflation position so as to start the slow deflation of the cuff, i.e., slow decreasing of the cuff pressure P. Steps SA205 and SA206 correspond to the cuff-pressure regulating means 278.

Step SA206 is followed by Step SA207 to judge whether the CPU 262 has read in one heartbeat-synchronous pulse of the CPW signal $SM_1$. Step SA207 is repeated until a positive judgment is made. Meanwhile, if a positive judgment is made at Step SA207, the control of the CPU 262 goes to Step SA208 to effect a BP measuring subroutine in which a systolic, a diastolic, and a mean BP value $SBP_1$, $DBP_1$, $MBP_1$, and a pulse-rate value $HR_1$, of the person are measured. More specifically described, the BP values $SBP_1$, $DBP_1$, $MBP_1$ of the person are determined based on the signals $SM_1$, SK obtained during the slow decreasing of the cuff pressure P, in the known oscillometric method. The systolic and diastolic BP values $SBP_1$, $DBP_1$ are determined based on the variation of respective magnitudes of heartbeat-synchronous pulses of the CPW signal $SM_1$ obtained during the slow cuff-pressure decreasing. The mean BP value $MBP_1$ is determined as being equal to the cuff pressure at the time of occurrence or detection of a heartbeat-synchronous pulse having the greatest or maximum amplitude. The pulse-rate value $HR_1$ is determined from the time interval between the respective times of detection of two successive heartbeat-synchronous pulses of the CPW signal $SM_1$. Step SA208 corresponds to the BP measuring means 280.

Step SA208 is followed by Step SA209 to judge whether a systolic BP value $SBP_1$ has been determined at Step SA208. If a negative judgment is made at Step SA209, the control of the CPU 262 goes back to Step SA207. On the other hand, if a positive judgment is made at Step SA209, the control of the CPU 262 goes to Step SA210 to judge whether a diastolic BP value $DBP_1$ has been determined at Step SA208. If a negative judgment is made at Step SA210, the control of the CPU 262 goes back to Step SA207. Meanwhile, if a positive judgment is made at Step SA210, the control of the CPU 262 goes to Step SA211 to store a set of BP data which represents the BP and pulse-rate values $SBP_1$, $DBP_1$, $MBP_1$, $HR_1$ determined at Step SA208 and the date and time of measurement of those values, in association with the ID data for the person, in the BP-data storing area of the memory device 268. In addition, at Step SA211, the determined BP and pulse-rate values $SBP_1$, $DBP_1$, $HR_1$ are displayed on the SBP, DBP, and HR displays 232, 234, 236, respectively.

Subsequently, at Step SA212, the CPU 262 of the control device 258 reads in one heartbeat-synchronous pulse of the ECG waveform detected by the ECG-waveform detecting device 270 and, at Step SA213, the CPU 262 reads in a corresponding heartbeat-synchronous pulse of the CPW waveform detected by the pressure sensor 240. Next, at Step SA214, the CPU 262 judges whether the CPU 262 has read in an R wave (or R point) of the heartbeat-synchronous pulse of the ECG waveform. If a negative judgment is made at Step SA214, the control of the CPU 262 goes back to Step SA212. Meanwhile, if a positive judgment is made at Step SA214, the control of the CPU 262 goes to Step SA215 to judge whether the CPU 262 has read in a maximum point of the corresponding heartbeat-synchronous pulse of the CPW waveform.

If a negative judgment is made at Step SA215, the control of the CPU 262 goes back to Step SA212. Meanwhile, if a positive judgment is made at Step SA215, the control of the CPU 262 goes to Step SA216 to switch the selector valve 242 to the quick-deflation position so as to start the quick decreasing of the cuff pressure P. Step SA216 corresponds to the cuff-pressure regulating means 278. Step SA216 is followed by Step SA217 to determine a time difference $TD_{RP}$ between the R wave of one pulse of the ECG waveform and the maximum point of corresponding pulse of the CPW waveform, as shown in FIG. 12. Step SA217 corresponds to the time-difference determining means 282. Step SA217 is followed by Step SA218 to determine a propagation velocity $V_{M1}$ of CPW, based on the time difference $TD_{RP}$ determined at Step SA217, according to the expression (2). Step SA218 corresponds to the propagation-velocity determining means 284.

Subsequently, at Step SA219, the CPU 262 determines a coefficient A occurring in the expression (3), based on the propagation velocity $V_{M1}$ determined at Step SA218 and the diastolic BP value $DBP_1$ determined at Step SA208, according to the expression (4). Step SA219 corresponds to the coefficient determining means 288. Step SA219 is followed by Step SA220 to modify the propagation velocity $V_{M1}$ determined at Step SA218 to a modified, i.e., normalized propagation velocity $V_{M2}$ corresponding to the predetermined BP value $BP_t$ and the predetermined pulse rate $HR_t$ based on the diastolic BP value $DBP_1$ and the pulse rate $HR_1$ measured at Step SA208, according to the expression (3). Step SA220 corresponds to the propagation-velocity modifying means 286.

Figure 14:
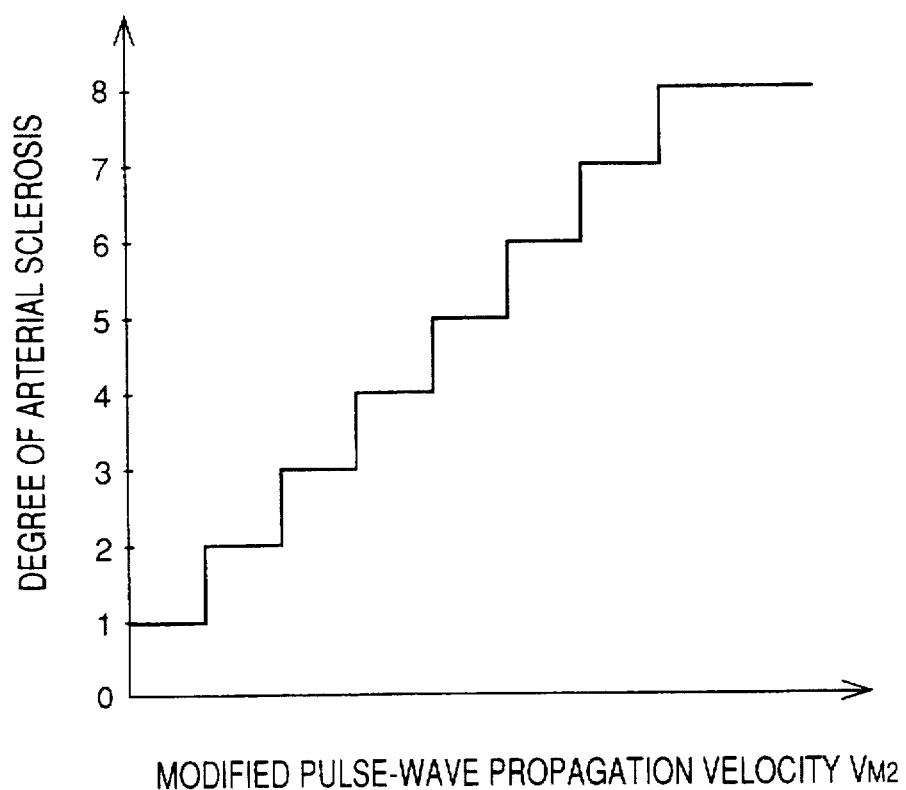
FIG. 14 is a map representing a relationship between degree of arterial sclerosis and modified pulse-wave propagation velocity $V_{M2}$ which is used for determining a degree of arterial sclerosis from a modified pulse-wave propagation velocity $V_{M2}$.
Figure 15:
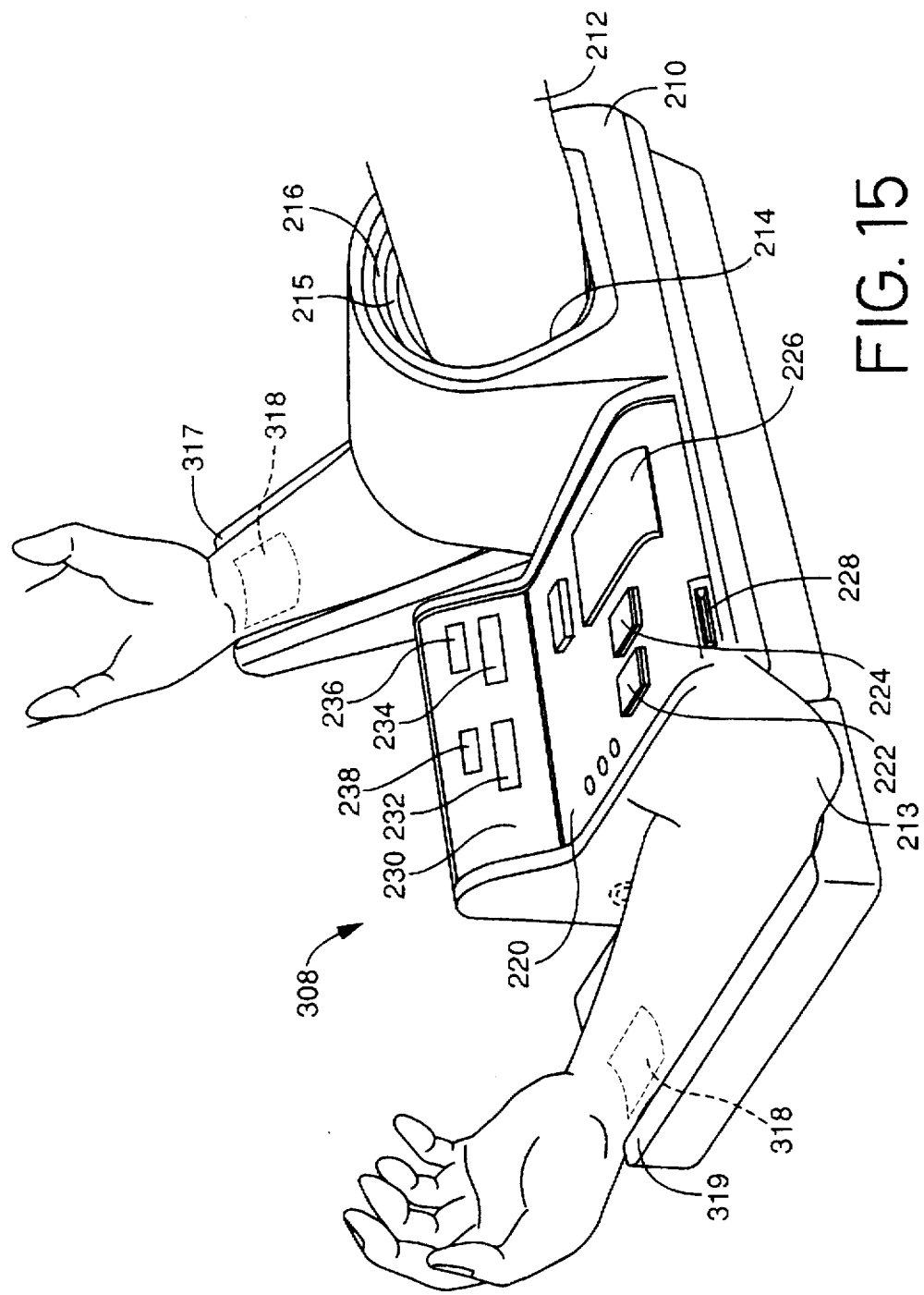
FIG. 15 is a perspective view corresponding to FIG. 8, showing another BP measuring apparatus providing another pulse-wave propagation velocity measuring apparatus as a fourth embodiment of the present invention.

In addition, at Step SA220, the CPU 262 of the control device 258 determines a degree of arterial sclerosis, DAS, of the person based on the modified propagation velocity $V_{M2}$ according to a predetermined relationship between degree of arterial sclerosis and modified propagation velocity $V_{M2}$, shown in FIG. 14, and store data indicative of the determined degree of arterial sclerosis DAS, together with the set of BP data stored at Step SA211, in the memory device 268. The relationship shown in FIG. 14 is experimentally pre-determined and is pre-stored in the ROM 264. As the degree of arterial sclerosis increases, the flexibility or softness of the arteries of the person decreases.

Step SA220 is followed by Step SA221 to command the printer 226 to output or record, on a recording sheet 290, the sets of BP data stored in the BP-data storing area of the memory device 268, as shown in FIG. 13. More specifically described, in an upper, left-hand portion of the sheet 290, the printer 226 records a name 292 of the person identified by the ID data or card 274. The name 292 of the person is represented by the registered ID data identifying the person. Bellow the name 292, the printer 226 records (a) a data list 294 showing the dates and times of measurements, the measured BP and pulse-rate values SBP, DBP, HR, and the determined degrees of arterial sclerosis DAS which have accumulatively been stored in the memory device 268; and (b) a graphic representation 296 of the sets of BP data and the sets of arterial-sclerosis data accumulatively stored in the memory device 268. The graphic representation 296 shows, along a common axis of abscissa 298 indicative of time, a series of vertical bars each of which has a top and a bottom horizontal segment which represent a systolic and a diastolic BP value SBP, DBP, respectively, a series of white triangles each of which represents a pulse-rate value HR, and a series of black circles each of which represents a degree of arterial sclerosis DAS, in the order of measurement or determination. Step SA221 is followed by Step SA222 to eject the magnetic card 274 from the card reader 272.

As is apparent from the foregoing description, in the third embodiment shown in FIGS. 8 to 14, the CPU 262 of the control device 258 determines, at Step SA217, the time difference $TD_{RP}$ between the predetermined periodic point (R wave) of each heartbeat-synchronous pulse of the ECG waveform and the predetermined periodic point (maximum point) of a corresponding heartbeat-synchronous pulse of the CPW waveform and determines, at Step SA218, the velocity $V_{M1}$ of propagation of the CPW through the artery of the subject, based on the time difference $TD_{RP}$ determined at Step SA217, according to the expression (2). In addition, at Step SA220, the CPU 262 modifies the propagation velocity $V_{M1}$ determined at Step SA218 to the modified propagation velocity $V_{M2}$ corresponding to the predetermined BP value $BP_t$ and the predetermined pulse rate $HR_t$, based on the diastolic BP value $DBP_1$ and the pulse rate $HR_1$ measured at Step SA208, according to the expression (3). Thus, even if the BP or pulse-rate values obtained from a living person in a plurality of measurements may differ from each other, the present apparatus 208 modifies each measured propagation velocity $V_{M1}$ to a modified propagation velocity $V_{M2}$ corresponding to the predetermined BP and pulse-rate values. Therefore, a series of modified propagation velocities $V_{M2}$ can directly be used as an index indicative of a time-wise change of the degree of arterial sclerosis of the person.

In addition, since the modified propagation velocity $V_{M2}$ corresponds to both the predetermined BP and pulse-rate values $BP_t$, $HR_t$, the value $V_{M2}$ is more accurate than a value, $V_{M2'}$, which corresponds to only the predetermined BP value $BP_t$ and is obtained according to the following expression (5):

$$V_{M2'}=V_{M1}+A(BP_t-DBP) \quad (5)$$

The value $V_{M2}$ is free from the influences or fluctuations due to the change of pulse rate HR of the person, whereas the value $V_{M2'}$ is subject to those fluctuations.

In the present apparatus 208, the modified propagation velocity $V_{M2}$ is calculated using the coefficient A which is calculated, at Step SA219, based on the propagation velocity $V_{M1}$ determined at Step SA218 and the diastolic BP value $DBP_1$ determined at Step SA208, according to the expression (4). Owing to the coefficient A, the value $V_{M2}$ is free from the influences or fluctuations due to the differences of individual persons with respect to the degree of arterial sclerosis. Therefore, the values $V_{M2}$ obtained from different persons can be compared with each other for comparing the respective degrees of arterial sclerosis of those persons.

In the present apparatus 208, the propagation velocity $V_{M1}$ or the modified propagation velocity $V_{M2}$ is obtained concurrently when the BP values $SBP_1$, $DBP_1$, $MBP_1$ are measured, and a series of values $V_{M2}$ can directly be used as an index indicative of a time-wise change of the degree of arterial sclerosis DAS. Thus, the person is provided with more physical information, with which he or she can think about his or her physical condition from more points of view. In addition, since the present apparatus 208 outputs the graphical representation 296 including the time-wise trend of DAS values, the person can easily and accurately see the time-wise change of the same.

In a conventional method, the pulse-wave propagation velocity is measured using a pulse-wave sensor which is applied, with the help of an exclusive assisting member, to a carotid artery or a femoral artery of a living subject. Thus, only the skilled person can fix the best condition under which the pulse-wave sensor is pressed against the artery via the skin, and it is considerably difficult for the subject himself or herself to measure his or her own propagation velocity. On the other hand, the present apparatus 208 can easily be operated by the subject without any skill to do so.

Figure 18:
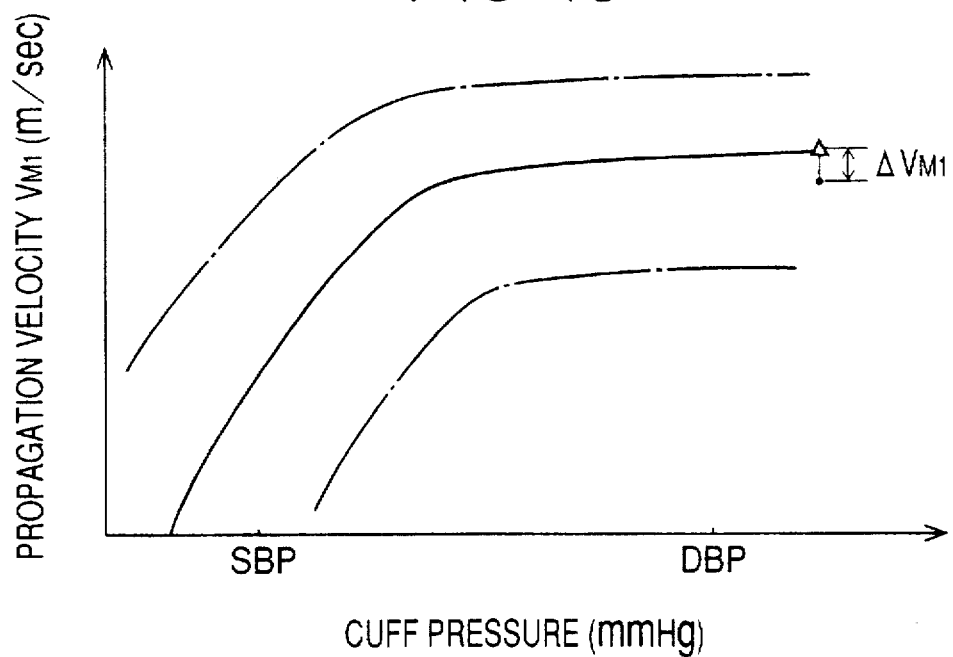
FIG. 18 is a graph showing the change of the propagation-velocity values $V_{M1}$ determined by the apparatus of FIG. 15, with respect to the pressure of an inflatable cuff of the same.

In the third embodiment, the time difference $TD_{RP}$ is determined, at Step SA216, based on the cuff pulse wave (i.e., CPW signal $SM_1$) detected through the pressure sensor 240 when the pressure of the cuff 215 is changed around the diastolic BP value $DBP_1$ of the person. Generally, in a time duration in which the cuff pressure is higher than the mean BP value $MBP_1$, the time difference $TD_{RP}$ increases as the cuff pressure decreases, as shown in FIG. 18. However, when the cuff pressure is around the diastolic BP value $DBP_1$, the time difference $TD_{RP}$ is not influenced by the change of the cuff pressure. Thus, the present apparatus 208 calculates a very accurate time difference $TD_{RP}$ and, accordingly, calculates a very accurate propagation velocity $V_{M1}$, $V_{M2}$.

In the third embodiment, the arm receiver 214 is adapted to receive the right arm 212 of the subject. However, it is possible to modify the arm receiver 214 to receive the left arm 213. In the latter case, the receiver 214 and the first arm rest 217 are provided on a left half portion of the housing 210, and the second arm rest 219 is provided on the right-hand side of the housing 210. Although the first arm rest 217 is provided at a tilt, the rest 217 may be provided to extend in a horizontal direction. The second arm rest 219 may be provided at a tilt. In any case, the arm rests 217, 219 are required to support the arms 212, 213 such that the muscles of the arms 212, 213 are kept relaxed.

Although, in the third embodiment, the first electrode 18 is provided on the free-end portion of the first arm rest 217 and the second electrode 18 is provided on the middle portion of the second arm rest 219, it is possible to dispose the electrodes 18 at different positions depending upon the shapes and positions of the rests 217, 219. In any case, the electrodes 18 are required to detect a stable or accurate ECG waveform from the arms 212, 213 of the person.

While in the third embodiment the degree of arterial sclerosis DAS is determined from the modified propagation velocity $V_{M2}$ corresponding to both the predetermined BP value $BP_t$ and the predetermined pulse rate $HR_t$, it is possible that the value DAS be determined from the modified propagation velocity $V_{M2'}$ which corresponds to only the predetermined BP value $BP_t$ and is calculated according to the expression (5). Since the pulse rate HR less influences the propagation velocity $V_{M1}$ than the blood pressure BP, the modified propagation velocity $V_{M2'}$ can be relied upon to determine the value DAS.

Although the BP measuring apparatus 208 employs the automatic winding device 216, 248, 250 which automatically winds the cuff 215 around the upper arm 212 of the person, the apparatus 208 may employ a different cuff which can be wound around the right arm 212 with the hand of the left arm 213 of the person.

The coefficient A calculated according to the expression (4) may be replaced by a coefficient, A', calculated according to the following expression (6):

$$A'=(B'\cdot V_{M1})/(C'\cdot DBP)+D' \quad (6)$$

The coefficient A' is variable in direct proportion to the propagation velocity $V_{M1}$ determined at Step SA218 and in reciprocal proportion to the diastolic BP value $DBP_1$ determined at Step SA208.

In the third apparatus 208, the printer 226 records, on the recording sheet 290, the data list 294 and the graphical representation 296 each of which contains the DAS (degree of arterial sclerosis) values. However, the printer 206 may be modified to record, in place of the DAS values, the modified propagation-velocity values $V_{M2}$ in one or each of the list 294 and the graph 296.

Although the third apparatus 208 determines BP values based on the variation of respective amplitudes of heartbeat-synchronous pulses of the CPW obtained during the slow decreasing of the cuff pressure, it is possible to modify the apparatus 208 to determine BP values based on the variation of respective amplitudes of heartbeat-synchronous pulses of a CPW obtained during a low-rate increasing of the cuff pressure.

While the third apparatus 208 measures BP values according to an oscillometric method, the principle of the present invention may be applied to a BP measuring apparatus which measures BP values according to a well-known Korotkoff-sound method.

Referring next to FIGS. 15 to 22, there will described a fourth embodiment of the present invention which relates to an automatic BP measuring apparatus 308 which automatically measures a BP value of a living subject and which also functions as an apparatus for measuring a propagation velocity of a pulse wave which is propagated through an artery of the subject.

The BP measuring apparatus 308 as the fourth embodiment has substantially the same hardware construction as the BP measuring apparatus 208 as the third embodiment shown in FIGS. 8 and 9. The same reference numerals as used in FIGS. 8 and 9 are used to designate the corresponding elements or parts of the fourth apparatus 308, and the description thereof is omitted from the following description.

However, the fourth apparatus 308 has a first and a second electrode 318, 318 and a first and a second arm rest 317, 318 which are different from those 218, 218, 217, 219 of the third apparatus 208.

Figure 16:
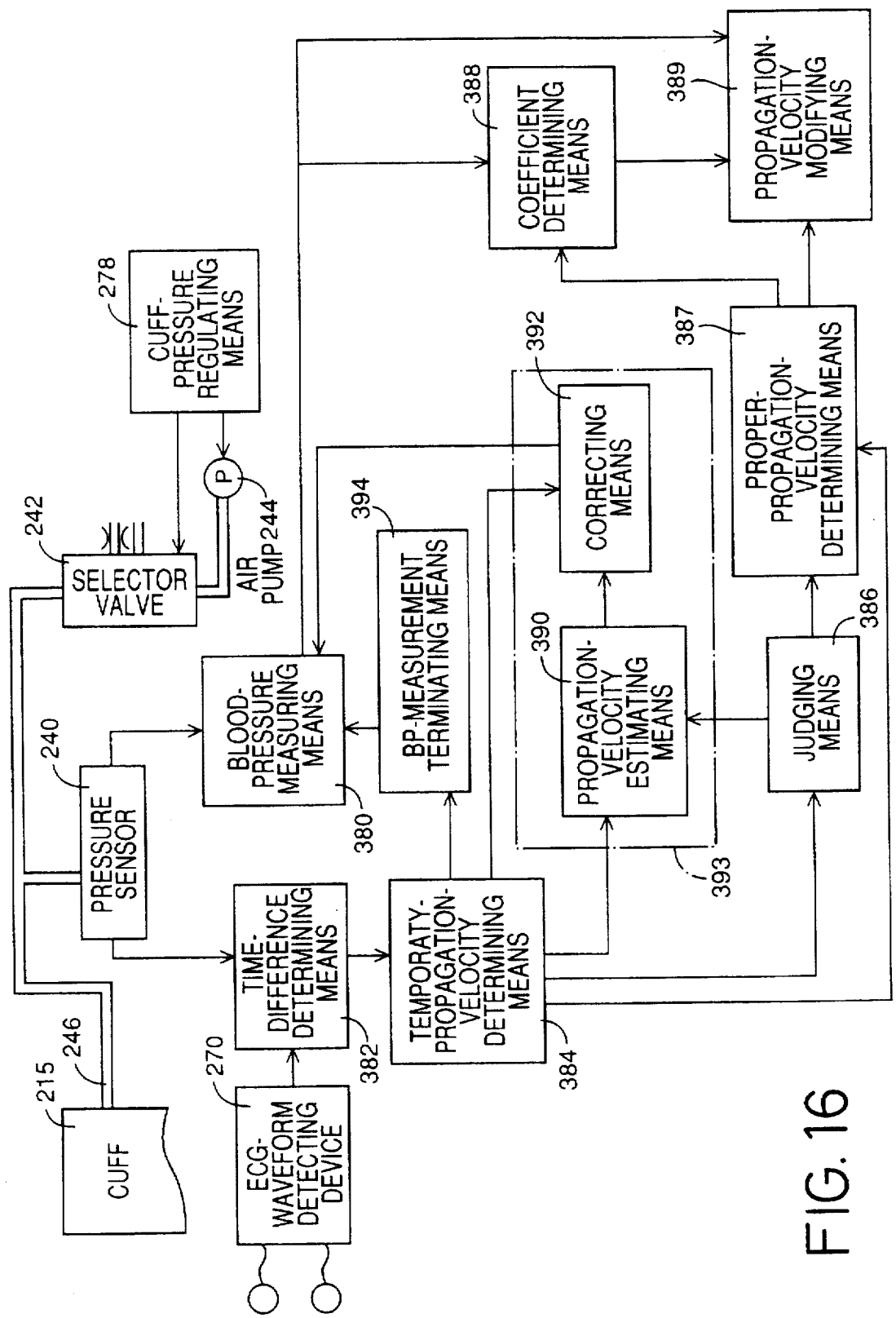
FIG. 16 is a block diagram corresponding to FIG. 10, for illustrating essential functions of an electronic control device of the apparatus of FIG. 15.

In addition, as shown in FIG. 16, an electronic control device 258 of the fourth apparatus 308 has different control functions 380, 382, 384, 386, 387, 388, 389, 393 (390, 392), 394 in addition to the same control function 278 as that 278 of the control device 258 of the third apparatus 208 shown in FIG. 10. The fourth apparatus 308 is controlled according to the control program represented by the flow charts of FIGS. 20 and 21, in place of the control program represented by the flow chart of FIG. 11. However, the main routine represented by the flow chart of FIG. 20 has the same steps, Steps SA201 through SA207, SA216, SA221, and SA222, as those SA201-SA207, SA216, SA221, SA222 of the control program represented by the flow chart of FIG. 11. The description of those steps is omitted from the following description.

The following description relates to only the differences of the fourth apparatus 308 from the third apparatus 208.

In the fourth apparatus 308, a first electrode 318 of an ECG-waveform detecting device 270 is provided on an end portion of a first arm rest 317 such that the first electrode 318 contacts the back of the wrist of a right arm 212 of a living subject. The upper surface of the arm rest 317 has a shape suitable for supporting the entire portion of the right arm 212 between the elbow and the wrist such that the muscles between the elbow and the wrist are kept relaxed for detecting an accurate ECG waveform from the subject. A second arm rest 319 is provided on the left-hand side of a housing 210, for supporting a left arm 213 of the subject, and a second electrode 318 is provided on an end portion of the arm rest 319 such that the second electrode 318 contacts the wrist of the left arm 213. The two electrodes 318 cooperate with each other to detect the electrocardiographic waveform from the subject. Like the first arm rest 317, the upper surface of the second arm rest 319 has a shape suitable for supporting the entire portion of the left arm 213 between the elbow and the wrist such that the muscles between the elbow and the wrist are kept relaxed for detecting an accurate ECG waveform.

The ECG-wave detecting device 270 detects the ECG waveform of the subject through the two electrodes 318 held in contact with the respective wrists of the right and left arms 212, 213 of the subject. An example of the ECG waveform detected through the electrodes 318 is shown in an upper portion of the graph of FIG. 17. An example of a cuff pulse wave (CPW) waveform detected through a cuff 215 and a pressure sensor 240 is shown in a lower portion of the graph of FIG. 17.

FIG. 16 illustrates essential control functions of the control device 258 of the fourth apparatus 308. The control device 258 functions as a cuff-pressure regulating means 278 which is the same as the cuff-pressure regulating means 278 of the third apparatus 208 shown in FIG. 10.

Figure 19:
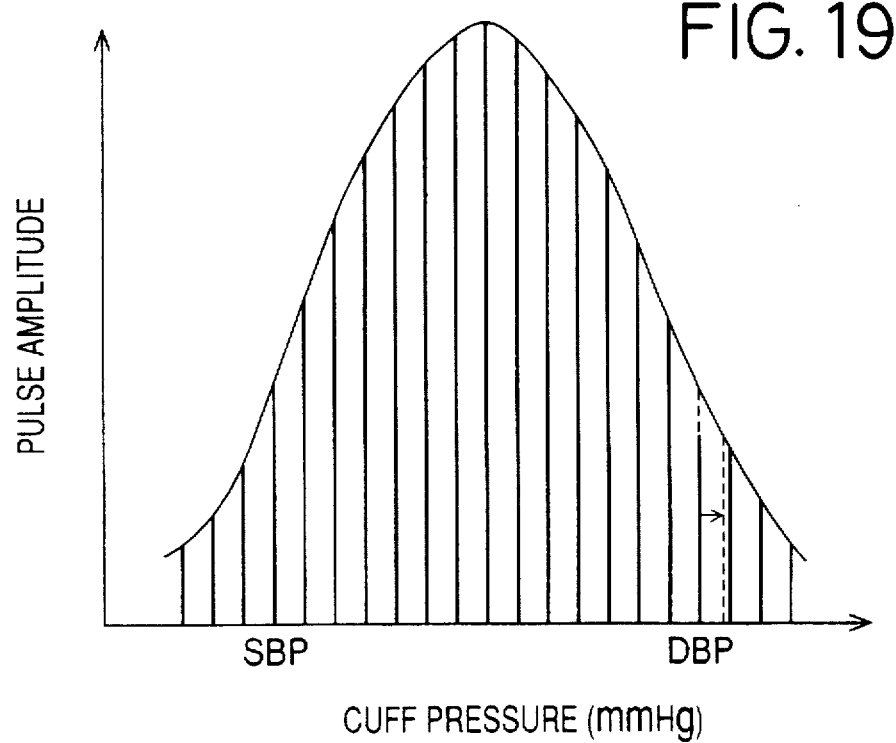
FIG. 19 is a graph showing the change of respective amplitudes of heartbeat-synchronous pulses of a pulse wave transmitted to the cuff, with respect to the cuff pressure.

The control device 258 of the fourth apparatus 308 functions as a BP measuring means 380 which is basically the same as the BP measuring means 280 of the third apparatus 208 shown in FIG. 10. However, one or more heartbeat-synchronous pulses of the CPW based on which the BP measuring means 380 measures BP values SBP, DBP, MBP of the subject, is or are corrected by a pulse correcting means 393 described later, as illustrated in FIG. 19.

The control device 258 of the third apparatus 308 additionally functions as a time-difference determining means 382 which successively determines a time difference between a predetermined periodic point relating to the ECG waveform of each of heartbeat-synchronous pulses of an electric signal supplied from the ECG-waveform detecting device 270, and a predetermined periodic point relating to the CPW waveform of a corresponding one of heartbeat-synchronous pulses of a CPW signal $SM_1$ which is supplied from the pressure sensor 240 when the pressure of the cuff 215 is changed around a diastolic BP value DBP of the subject. In the present embodiment, the determining means 382 determines a time difference, $TD_{RP}$, between the time of occurrence or detection of an R wave of each pulse of the ECG waveform and the time of occurrence or detection of a minimum point (lower-peak point) of a corresponding pulse of the CPW waveform, as shown in FIG. 17. In the present embodiment, the predetermined periodic point relating to the CPW waveform is defined as a rising point of each heartbeat-synchronous pulse, and the rising point may be defined as the minimum point, i.e., lower-peak point of each pulse. However, the rising point may otherwise be defined as a point greater than a minimum point by a predetermined magnitude, or a point where the slope or differential of the CPW waveform takes a maximum value. In short, the rising point may be defined as any periodic point other than a maximum (i.e. upper-peak) point of each pulse that is used by the time-difference determining means 282 of the third apparatus 208.

The control device 258 of the fourth apparatus 308 functions as a temporary-propagation-velocity determining means 384 which determines a temporary propagation velocity $V_{M1}$ (m/sec) of CPW, based on each of the successively determined time-difference values $TD_{RP}$, according to the same expression as the previously-indicated expression (2): $V_{M1}=L/(TD_{RP}-T_{PEP})$. However, in the present embodiment, a pre-ejection period $T_{PEP}$ is defined as the time interval between the R wave of each pulse of the ECG waveform and the minimum point of a corresponding pulse of an aortic pulse wave produced from the aorta of the subject. This value $T_{PEP}$ is experimentally pre-determined and pre-stored in the ROM 264.

In addition, the control device 258 of the fourth apparatus 308 functions as a stability judging means 386 which judges whether the propagation-velocity values $V_{M1}$ successively determined by the propagation-velocity determining means 384 have become stable, e.g., whether the amount or rate of change of the propagation-velocity values $V_{M1}$ has become not higher than a first or a second reference value, e.g., 0.1 m/sec or 3%, respectively; and as a proper-propagation-velocity determining means 387 which determines, as a proper propagation velocity, $V_{PM1}$, of the subject, an average of a predetermined number of the propagation-velocity values $V_{M1}$ (corresponding to the level portion of a curve indicated at solid line in FIG. 18) which are determined by the propagation-velocity determining means 284 and are not higher than the first or second reference value. This number is counted by the CPU 262 from the first value $V_{M1}$ that first becomes not higher than the first or second reference value. However, the first value $V_{M1}$ itself may be determined as the proper propagation-velocity value $V_{PM1}$.

The control device 258 of the fourth apparatus 308 also functions as a propagation-velocity modifying means 389 which modifies the proper propagation velocity $V_{PM1}$ determined by the proper-propagation-velocity determining means 387, to a modified (i.e., normalized) proper propagation velocity $V_{M3}$ (m/sec) corresponding to a predetermined (i.e., normalized) BP value $BP_r$ (e.g., 80 mmHg) and a predetermined pulse rate $HR_r$ (e.g., 70 BPM (beats per minute)), based on the diastolic BP value DBP measured by the BP measuring means 380 and a measured pulse rate HR, according to the following expression (7) similar to the expression (3):

$$V_{M3}=V_{PM1}+A(BP_r-DBP)+E(HR_r-HR) \quad (7)$$

where $$A=B \cdot V_{PM1}+C \cdot DBP+D \quad (8);$$

and

B, C, D, and E are constants.

The coefficient A occurring in the expression (7) is determined by a coefficient determining means 388 according to the above expression (8). The coefficient A increases as the propagation velocity $V_{PM1}$ increases, and decreases as the diastolic BP value DBP increases. The control device 258 of the fourth apparatus 308 functions as the coefficient determining means 388. The constant E occurring in the expression (7) and the constants, B, C, D, occurring in the expression (8) are experimentally determined in advance. The constant B is positive and the constant C is negative.

In addition, the control device 258 of the fourth apparatus 308 functions as a propagation-velocity estimating means 390 which estimates, as the next propagation-velocity value, $V_{M1'}$, (corresponding to a white triangle shown in FIG. 18) which will next be determined by the propagation-velocity determining means 384, an average of a predetermined number of the propagation-velocity values $V_{M1}$ (corresponding to the level portion of the curve indicated at solid line in FIG. 18) which are determined by the propagation-velocity determining means 384 and are not higher than the first or second reference value, according to a predetermined expression (9):

$$V_{M1'}=[(V_{M1})_{i-n}+ \ldots +(V_{M1})_{i-1}+(V_{M1})_i]/(n+1)$$

This number is counted by the CPU 262 from the first value $V_{M1}$ that first becomes not higher than the first or second reference value. However, the last value $V_{M1}$ itself may be estimated as the next propagation-velocity value $V_{M1'}$.

Moreover, the control device 258 of the fourth apparatus 308 functions as a correcting means 392 which calculates a difference, $\Delta V_{M1}$, of the next propagation-velocity value $V_{M1'}$ estimated by the estimating means 390 and the next, actual propagation-velocity value $V_{M1}$ (corresponding to a black circle shown in FIG. 18) which is actually determined by the determining means 384, according to a predetermined expression (10):

$$\Delta V_{M1}=V_{M1'}-V_{M1} \quad (10)$$

The correcting means 392 additionally calculates a first correction value, $X_1$, according to a predetermined expression (11):

$$X_1=F \cdot (\Delta V_{M1}) \quad (11)$$

where F is a positive constant which is experimentally determined in advance.

The first correction value $X_1$, indicated at broken line in FIG. 19, is added to the amplitude, indicated at solid line, of one heartbeat-synchronous pulse of CPW from which the current propagation-velocity value $V_{M1}$ (i.e., above-indicated next value $V_{M1'}$) is determined.

Alternatively, the correcting means 392 calculates a second correction value, $X_2$, according to a predetermined expression (12):

$$X_2=-G \cdot (\Delta V_{M1}) \quad (12)$$

where G is a positive constant which is experimentally determined in advance.

The second correction value $X_2$ is added to the cuff-pressure value at the time of occurrence or detection of one heartbeat-synchronous pulse of CPW from which the current propagation-velocity value $V_{M1}$ (i.e., above-indicated next value $V_{M1'}$) is determined, so that the amplitude, indicated at solid line, of the pulse is moved to an amplitude indicated at broken line. The propagation-velocity estimating means 390 and the correcting means 392 cooperate with each another to provide a pulse correcting means 393 which correct the pulses of CPW, as needed. The corrected CPW pulses are utilized by the BP measuring means 380 for measuring the BP values of the subject.

Furthermore, the control device 258 of the fourth apparatus 308 functions as a BP-measurement terminating means 394 which terminates the current BP measuring operation of the BP measuring means 380, if the current propagation-velocity value $V_{M1}$ determined by the determining means 384 does not fall within a permission range indicated at one-dot chain line in FIG. 18. This permission range is experimentally pre-determined for all the values that can be taken by the cuff pressure, and pre-stored in the ROM 264. However, it is possible to determine the permission range based on the propagation-velocity values $V_{M1}$ determined by the determining means 384 prior to the current value $V_{M1'}$, for example, the estimated value $V_{M1'}$. In either case, the upper and lower limits of each permission range may be determined by a statistical technique such that it is almost impossible for a corresponding value $V_{M1}$ to fall outside the range.

Hereinafter, there will be described the operation of the BP measuring apparatus 308 constructed as described above, by reference to the flow charts of FIGS. 20 and 21.

Figure 11:
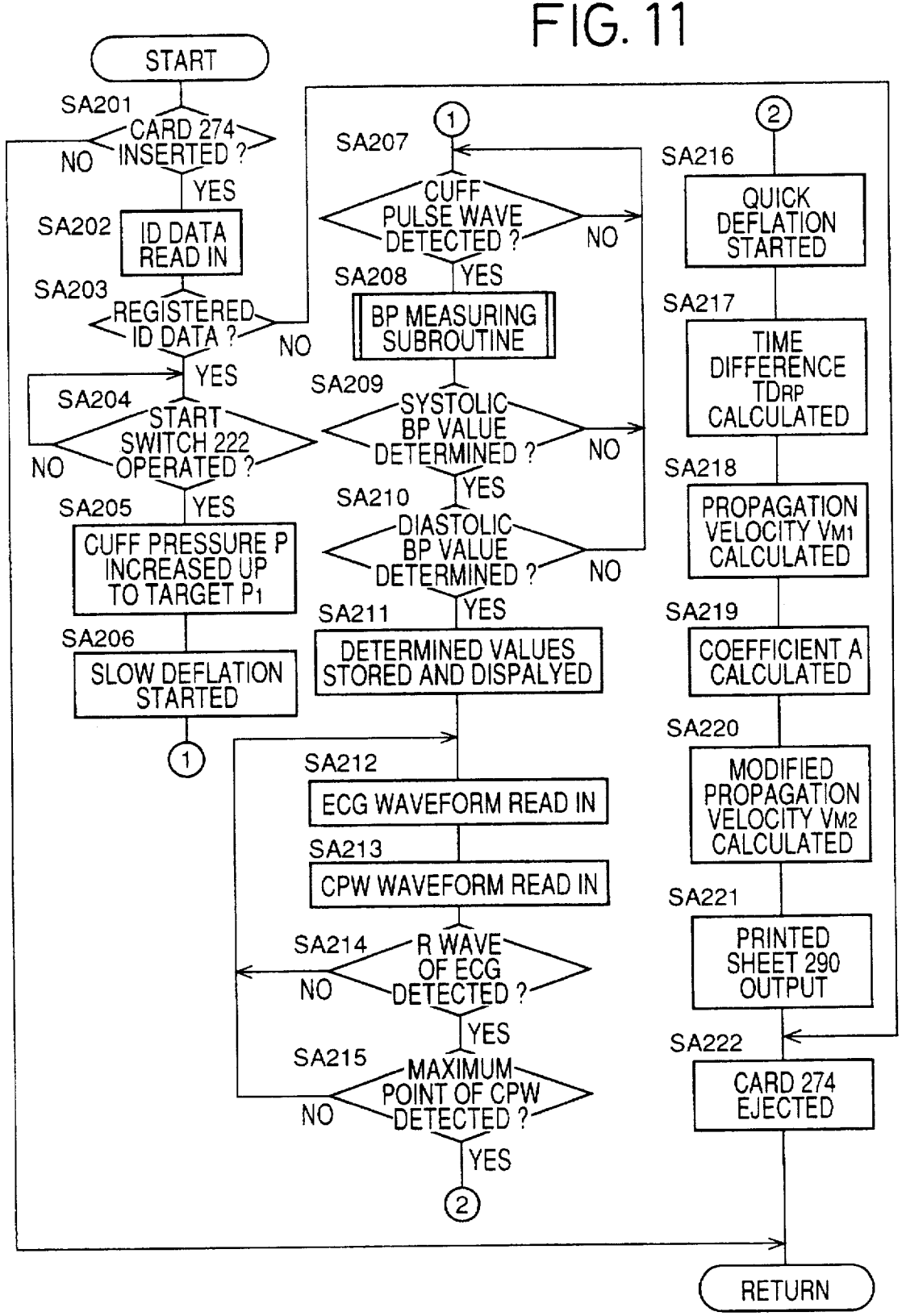
FIG. 11 is a flow chart representing a control program according to which the apparatus of FIG. 8 is controlled.
Figure 20:
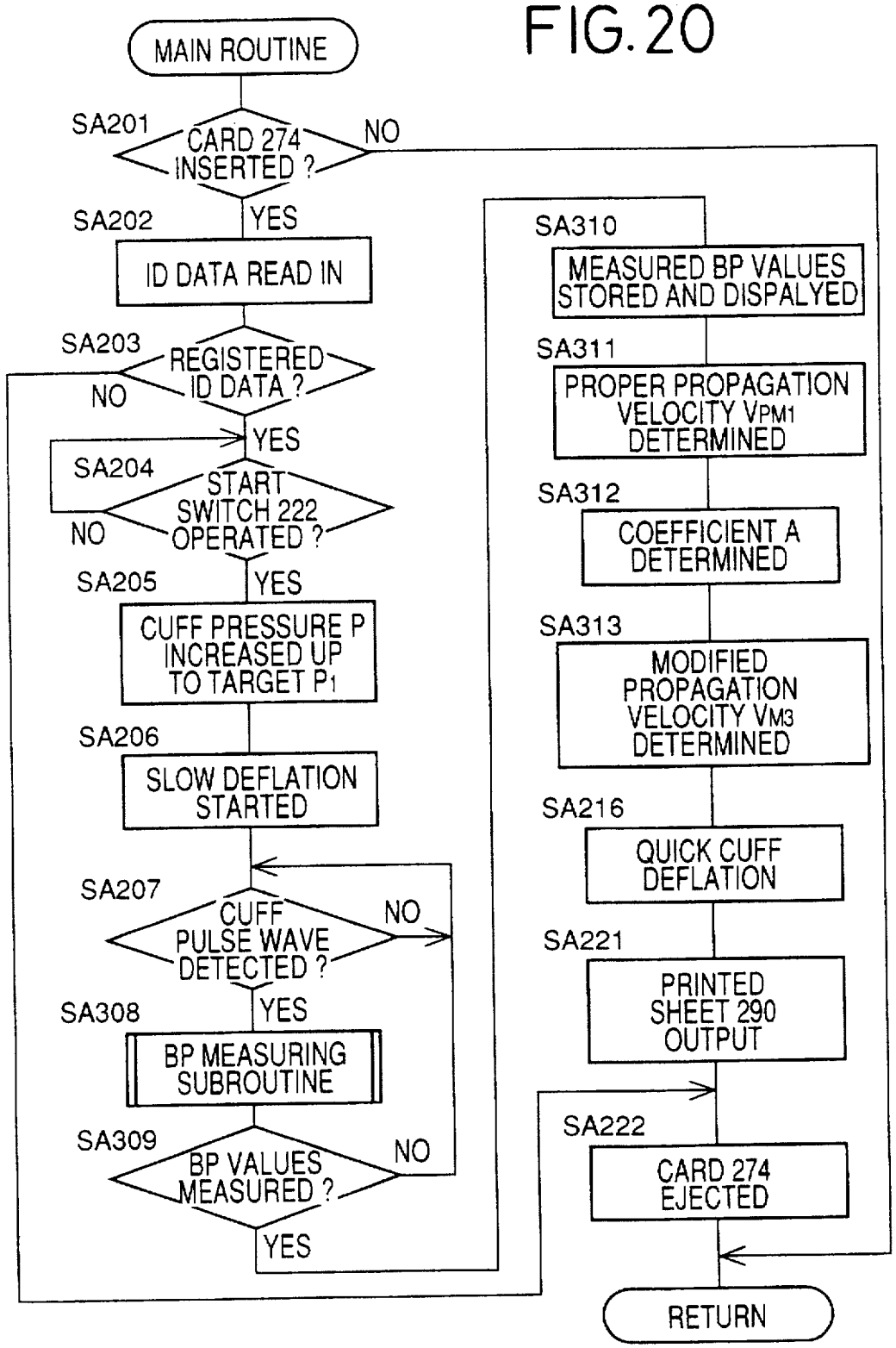
FIG. 20 is a flow chart representing a control program according to which the apparatus of FIG. 15 is controlled.

Steps SA201 to SA207 of FIG. 20 are the same as those SA201 to SA207 of FIG. 11.

At Step SA308, a CPU 262 of the control device 258 determines a systolic, a diastolic, and a mean BP value $SBP_1$, $DBP_1$, $MBP_1$ and a pulse-rate value HR in the same manner as that employed at Step SA208 of FIG. 11. However, one or more heartbeat-synchronous pulses of the CPW that is utilized by by the BP measuring means 380 may be corrected at Step SB313 described later.

Step SA308 is followed by Step SA309 to judge whether a systolic BP value $SBP_1$ and a diastolic BP value $DBP_1$ have been determined at Step SA308. If a negative judgment is made at Step SA309, the control of the CPU 262 of the control device 258 of the fourth apparatus 308 goes back to Step SA207. On the other hand, if a positive judgment is made at Step SA309, the control of the CPU 262 goes to Step SA310 to store a set of BP data which represents the BP and pulse-rate values $SBP_1$, $DBP_1$, $MBP_1$, $HR_1$ determined at Step SA308 and the date and time of measurement of those values, in association with ID data identifying a magnetic card 274, i.e., a living person carrying the card 274, in a BP-data storing area of a memory device 268. In addition, at Step SA310, the determined BP and pulse-rate values $SBP_1$, $DBP_1$, $HR_1$ are displayed on a SBP, a DBP, and a HR display 232, 234, 236, respectively.

Step SA310 is followed by Step SA311 to determine, as a proper propagation velocity $V_{PM1}$ of the subject, an average of the first, second, and third temporary propagation-velocity values $V_{M1}$ which have first, second, and third become not higher than the first or second reference value and have been stored in a second memory area (described later) of a RAM 266 of the control device 258 of the fourth apparatus 308. Step SA311 corresponds to the proper-propagation-velocity determining means 387.

Step SA311 is followed by Step SA312 to determine a coefficient A occurring in the expression (7), based on the proper propagation-velocity value $V_{PM1}$ determined at Step SA311 and the diastolic BP value $DBP_1$ determined at Step SA308, according to the expression (8). Step SA312 corresponds to the coefficient determining means 388. Step SA312 is followed by Step SA313 to modify the proper propagation velocity $V_{PM1}$ determined at Step SA311 to a modified, i.e., normalized proper propagation velocity $V_{M3}$ corresponding to the predetermined BP value $BP_t$ and the predetermined pulse rate $HR_t$, based on the diastolic BP value $DBP_1$ and the pulse rate $HR_1$ measured at Step SA308, according to the expression (7). Step SA313 corresponds to the propagation-velocity modifying means 389.

Figure 22:
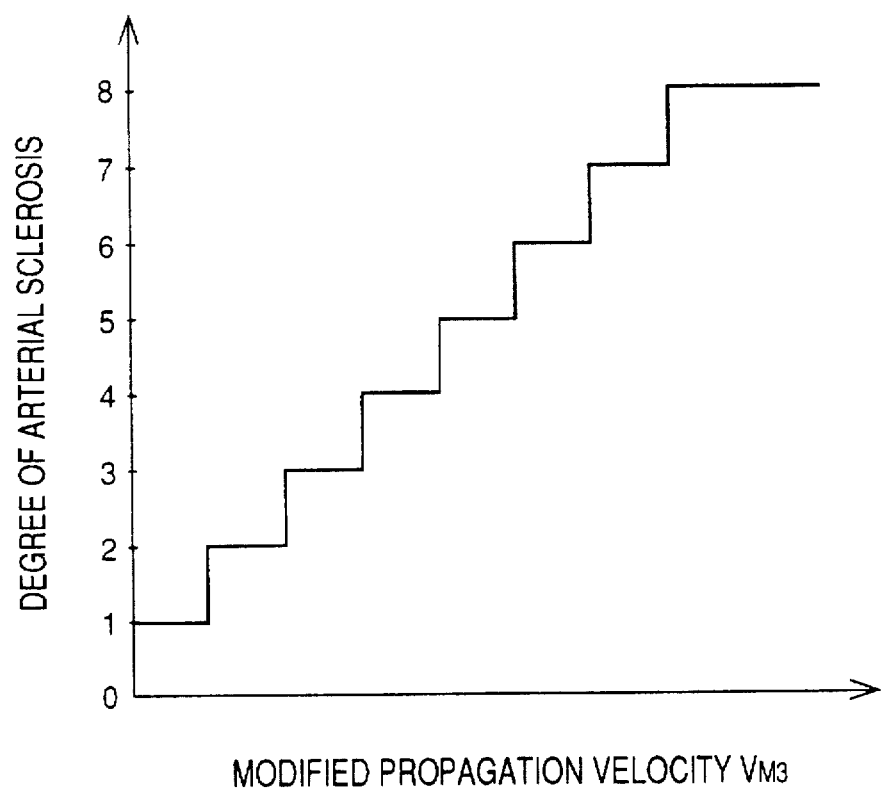
FIG. 22 is a map representing a relationship between degree of arterial sclerosis and modified propagation velocity $V_{M3}$ that is used for determining a degree of arterial sclerosis from a modified propagation velocity $V_{M3}$.

In addition, at Step SA313, the CPU 262 of the control device 258 of the fourth apparatus 308 determines a degree of arterial sclerosis DAS of the person based on the modified propagation velocity $V_{M3}$ according to a predetermined relationship between degree of arterial sclerosis and modified propagation velocity $V_{M3}$, shown in FIG. 22, and store data indicative of the determined degree of arterial sclerosis DAS, together with the set of BP data stored at Step SA310, in the memory device 268. The relationship shown in FIG. 22 is experimentally predetermined and is pre-stored in the ROM 264. As the degree of arterial sclerosis increases, the flexibility or softness of the arteries of the person decreases.

Subsequently, at Step SA216, a selector valve 242 is switched to a quick-deflation position thereof so as to start the quick decreasing of the cuff pressure P. Step SA216 corresponds to the cuff-pressure regulating means 278. Step SA216 is followed by Steps SA221 and SA222 which are the same as Steps SA221, SA222 of FIG. 11.

Figure 21:
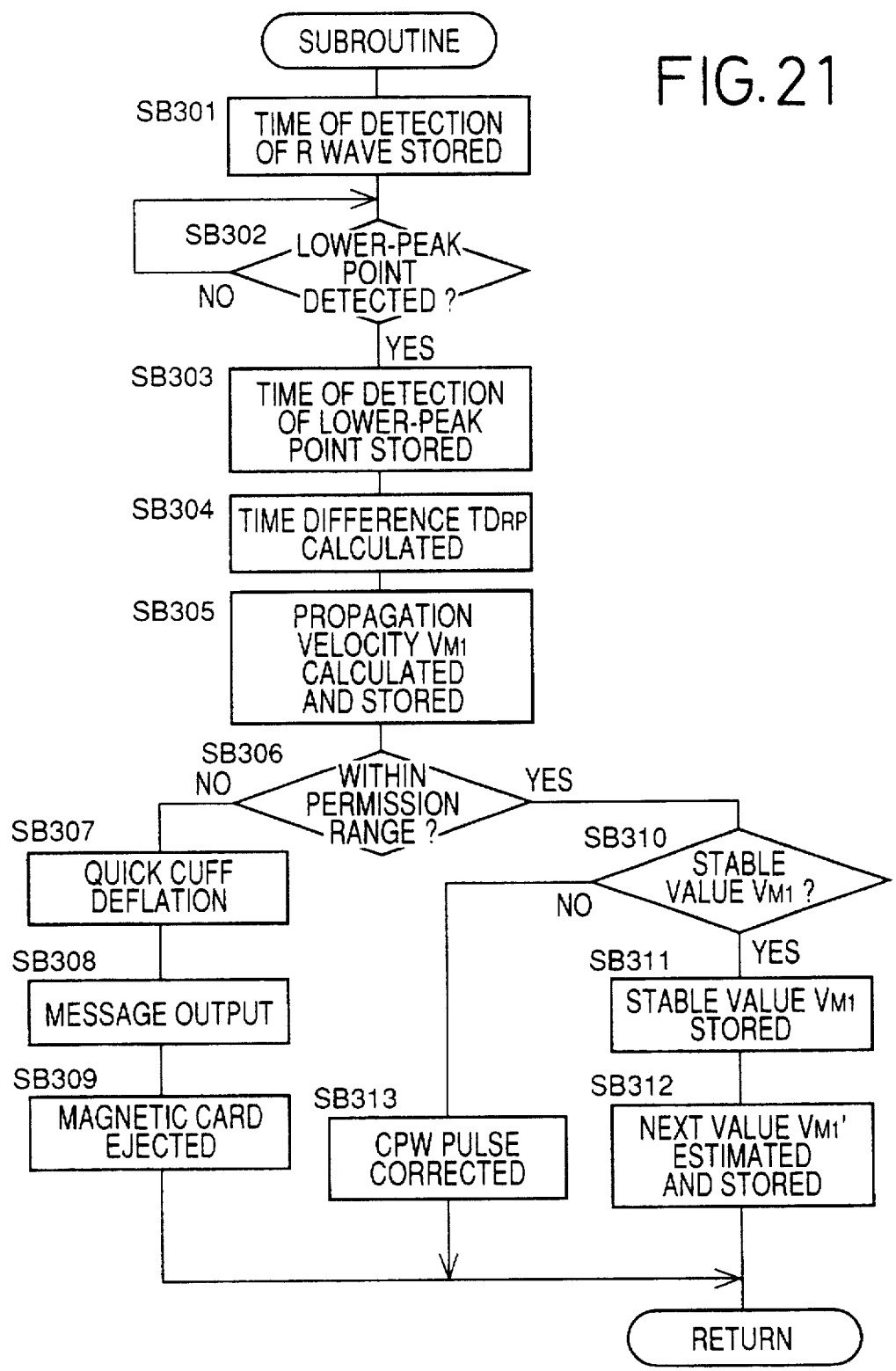
FIG. 21 is a flow chart representing an interrupt subroutine according to which the apparatus of FIG. 15 is controlled.

The flow chart of FIG. 21 represents an interrupt subroutine which is implemented when the CPU 262 reads in the R wave of each heartbeat-synchronous pulse of the ECG waveform (i.e., electric signal) detected by the ECG-waveform detecting device 270, while the main routine represented by the flow chart of FIG. 20 is implemented. At Step SB301, the CPU 262 of the control device 258 of the fourth apparatus 308 specifies the time when the R wave of one pulse is detected or read in, and stores the specified time in the RAM 266. Step SB301 is followed by Step SB302 to judge whether the CPU 262 has read in the lower-peak point of a corresponding pulse of the CPW waveform (i.e., CPW signal $SM_1$) detected through the pressure sensor 240. If a negative judgment is made at Step SB302, Step SB302 is repeated until a positive judgment is made. Meanwhile, if a positive judgment is made at Step SB302, the control of the CPU 262 goes to Step SB303 to specify the time when the lower-peak point of the corresponding pulse is detected or read in, and stores the specified time in the RAM 266. Step SB303 is followed by Step SB304.

At Step SB304, the CPU 262 determines a time difference $TD_{RP}$ between the time of detection of the R wave of the ECG waveform and the time of detection of the lower-peak point of the CPW waveform, as illustrated in FIG. 17. Step SB304 corresponds to the time-difference determining means 382. Step SB304 is followed by Step SB305 to determine a temporary propagation velocity $V_{M1}$ of CPW, based on the time difference $TD_{RP}$ determined at Step SB304, according to the expression (2). The determined value $V_{M1}$ is stored in a first memory area of the RAM 66. Step SB305 corresponds to the temporary-propagation-velocity determining means 384.

Subsequently, at Step SB306, the CPU 262 judges whether the current propagation-velocity value $V_{M1}$ determined at Step SB305 falls within a predetermined permission range. This permission range has the upper and lower limits indicated at one-dot chain line in FIG. 18. If a negative judgment is made at Step SB306, the control of the CPU 262 goes to Step SB307 to switch the selector valve 242 to the quick-deflation position so as to start the quick deflation of the cuff 215. Thus, the current BP measurement is terminated. Steps SB306 and SB307 correspond to the BP-measurement terminating means 394. Step SB307 is followed by Step SB308 to control a printer 226 to print, on a recording sheet 290, a message that another BP measurement should be tried and output the printed sheet. Then, at Step SB309, a magnetic card 274 is ejected through a card insertion slot 228.

On the other hand, if a positive judgment is made at Step SB306, the control of the CPU 262 goes to Step SB310 to judge whether the amount or rate of change of the current propagation-velocity value $V_{M1}$ determined in the current control cycle from the preceding value $V_{M1}$ determined in the preceding control cycle and stored in the first memory area of the RAM 266 is not greater than 0.1 m/sec or 3%. If a positive judgment is made at Step SB310, the control of the CPU 262 goes to Step SB311 to store temporarily the current propagation-velocity value $V_{M1}$ determined at Step SB305 in the current control cycle, in the second memory area of the RAM 266. Step SB310 corresponds to the stability judging means 386.

Step SB311 is followed by Step SB312 to estimate a next propagation-velocity value $V_{M1'}$ indicated at the white triangle in FIG. 18, based on the propagation-velocity values $V_{M1}$ stored in the second memory area of the RAM 266, according to the expression (9). The estimated next value $V_{M1'}$ is temporarily stored in a third memory area of the RAM 266. Step SB312 corresponds to the propagation-velocity estimating means 390.

On the other hand, if a negative judgment is made at Step SB310, the control of the CPU 262 goes to Step SB313 to determine a difference $\Delta V_{M1}$ between the last estimated next propagation-velocity value $V_{M1'}$ (indicated at the white triangle) that has last stored in the third memory area of the RAM 266, and the current propagation-velocity value $V_{M1}$ (indicated at the black circle) which has been determined at Step SB305 in the current control cycle, according to the expression (10), as illustrated in FIG. 18. In addition, the CPU 262 determines a first correction value $X_1$ based on the determined difference $\Delta V_{M1}$ according to the expression (11), or determines a second correction value $X_2$ based on the determined difference $\Delta V_{M1}$ according to the expression (12). The first correction value $X_1$ is added to the amplitude of the pulse of CPW waveform from which the current value $V_{M1}$ has been derived, or the second correction value $X_2$ is added to the pressure of the cuff 215 at the time of detection of the pulse of CPW waveform from which the current value $V_{M1}$ has been derived. Thus, the CPW pulse is corrected and the corrected pulse is used by the BP measuring means 380 for carrying out the current BP measurement at Step SB308.

As is apparent from the foregoing description, in the fourth embodiment shown in FIGS. 15 to 22, the ECG-waveform detecting device 270 detects the ECG waveform through the electrodes 318 held in contact with the subject, and the pressure sensor 240 (i.e., pulse-wave sensor) detects the CPW waveform from the subject. The CPU 262 determines, at Step SB304, the time difference $TD_{RP}$ between the predetermined periodic point (R wave) of each heartbeat-synchronous pulse of the ECG waveform and the predetermined periodic point (lower-peak or minimum point) of a corresponding heartbeat-synchronous pulse of the CPW waveform and determines, at Step SB305, the velocity $V_{M1}$ of propagation of the CPW through the artery of the subject, based on the time difference $TD_{RP}$ determined at Step SB304. In addition, at Step SB310, the CPU 262 judges whether the change of each of the propagation-velocity values $V_{M1}$ from a corresponding preceding value $V_{M1}$ is smaller than a reference value and, at Step SA311, the CPU 262 determines, as a proper propagation-velocity value $V_{PM1}$, an average of the first, second, and third values $V_{M1}$ for which the first, second, and third positive judgments are made, respectively, at Step SB310. Since the proper propagation-velocity value $V_{PM1}$ is determined based on the values $V_{M1}$ that are stable independent of the change of cuff pressure, the accuracy of measurement of pulse-wave propagation velocity is improved.

In addition, at Step SB312, the CPU 262 estimates, according to the expression (9), a next propagation-velocity value $V_{M1'}$ which will next be determined at Step SB305, based on the propagation-velocity values $V_{M1}$ which have been determined at Step SB305 and for each of which a positive judgment is made at Step SB310. Subsequently, at Step SB313, the CPU 262 determines the difference $\Delta V_{M1}$ between the estimated next value $V_{M1'}$ and the current value $V_{M1}$ determined at Step SB305 in the current control cycle, according to the expression (10), and additionally determines the first correction value $X_1$ based on the determined difference $\Delta V_{M1}$ according to the expression (11), or determines the second correction value $X_2$ based on the determined difference $\Delta V_{M1}$ according to the expression (12). The first correction value $X_1$ is added to the amplitude of the pulse of CPW waveform from which the current value $V_{M1}$ has been derived, or the second correction value $X_2$ is added to the pressure of the cuff 215 at the time of detection of the pulse of CPW waveform from which the current value $V_{M1}$ has been derived. Thus, the CPW pulse is corrected and the corrected pulse is used at Step SB308 for determining BP values in the current BP measurement. In this way, even in the case where the relationship of correspondence of pulse amplitude and cuff pressure (or blood pressure) breaks for a certain reason during each BP measurement, the pulse-amplitude value or the cuff-pressure value is advantageously corrected. Thus, the accuracy of measurement of BP values is improved.

Moreover, in the fourth apparatus 308, at Step SB306, the CPU 262 judges whether each temporary propagation-velocity value $V_{M1}$ determined at Step SB305 falls within the predetermined permission range having the upper and lower limits indicated at one-dot chain line in FIG. 18. This permission range is experimentally pre-determined for all the values that can be taken by the pressure of the cuff 215. If a negative judgment is made at Step SB306, the CPU 262 terminates the current BP measurement being carried out at Step SB308 of FIG. 20, by quickly deflating the cuff 215 at Step SB307 of the interrupt subroutine of FIG. 21. Thus, if an abnormal event occurs during each BP measurement and the propagation velocity $V_{M1}$ takes an excessively high or low value, the BP measurement is ended. Therefore, inaccurate BP measurements are effectively avoided.

In the fourth embodiment, at Step SA311, the CPU 262 determines, as the proper propagation velocity $V_{PM1}$, the average of the first three values $V_{M1}$ for each of which a positive judgment is made at Step SB310. However, the CPU 262 may be modified to determine, as the proper propagation velocity $V_{PM1}$, the first value $V_{M1}$ for which the first positive judgment is made at Step SB310, or a different single value $V_{M1}$ for which a positive judgment is made at Step SB310. Alternatively, the CPU 262 may be modified to determine, as the proper propagation velocity $V_{PM1}$, the average of two, four, or more values $V_{M1}$ for each of which a positive judgment is made at Step SB310.

In the fourth embodiment, at Step SB312, the CPU 262 estimates the next propagation-velocity value $V_{M1'}$, based on the prior propagation-velocity values $V_{M1}$ stored in the second memory areas of the RAM 266, according to the expression (9), i.e., determines, as the estimated value $V_{M1'}$, a moving average of the values $V_{M1}$ stored in the second memory area of the RAM 266. However, the CPU 262 may be modified to estimate the next value $V_{M1'}$ by utilizing a statistical method, i.e., a regression line.

In the fourth apparatus 308, the electrodes 318 provided on the arm rests 317, 319 may be replaced by conventional suction-type electrodes adapted to be placed at predetermined positions on a living subject.

Referring next to FIGS. 23 to 27, there will described a fifth embodiment of the present invention which relates to an automatic BP measuring apparatus 408 which automatically measures a BP value of a living subject and which also functions as an apparatus for measuring a propagation velocity of a pulse wave which is propagated through an artery of the subject.

The BP measuring apparatus 408 as the fifth embodiment has the same hardware construction as the BP measuring apparatus 208 as the third embodiment shown in FIGS. 8 and 9. The same reference numerals as used in FIGS. 8 and 9 are used to designate the corresponding elements or parts of the fifth apparatus 408, and the description thereof is omitted from the following description.

Figure 23:
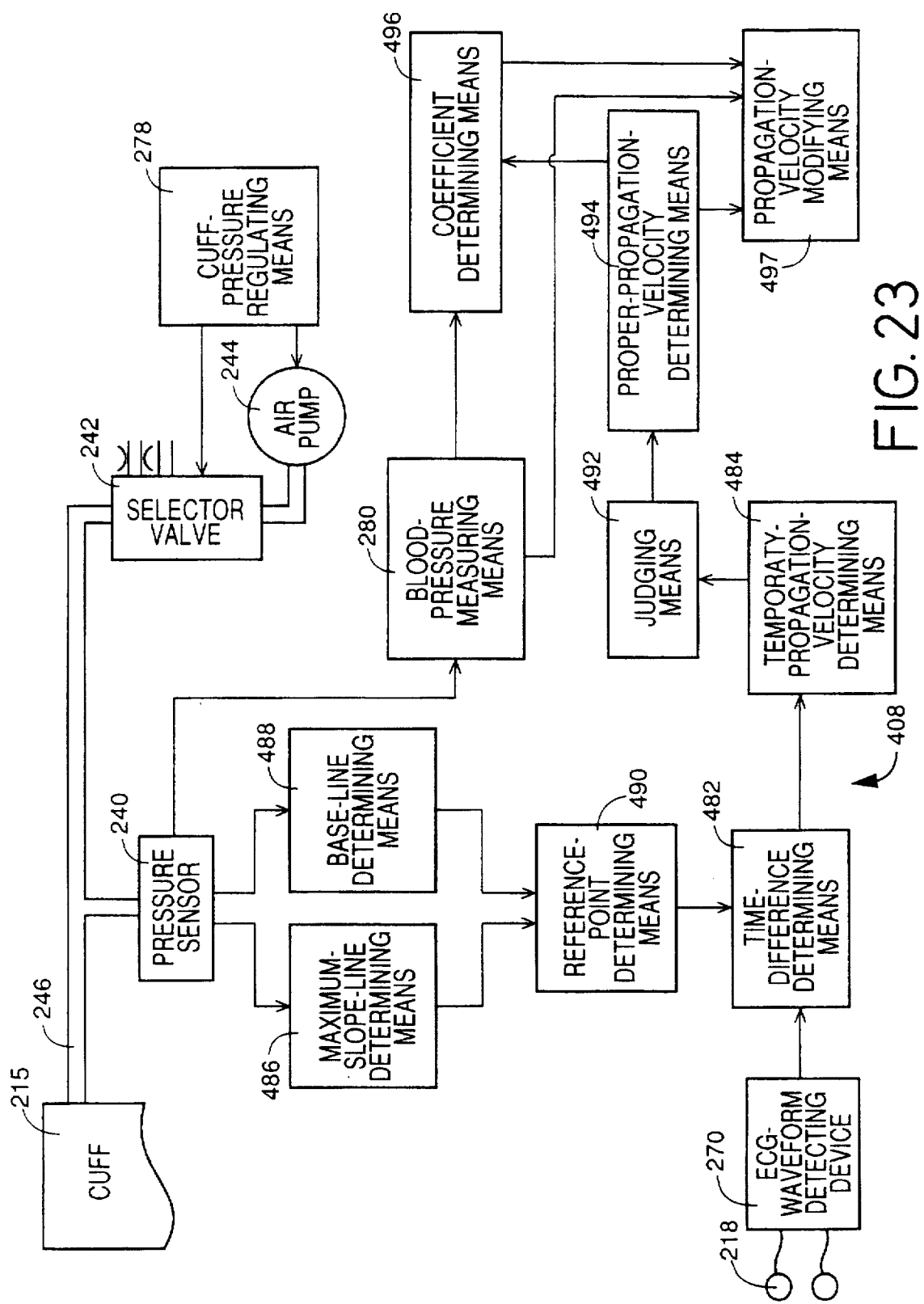
FIG. 23 is a block diagram corresponding to FIG. 10, for illustrating essential functions of an electronic control device of another BP measuring apparatus providing another propagation-velocity measuring apparatus as a fifth embodiment of the present invention.

However, as shown in FIG. 23, an electronic control device 258 of the fifth apparatus 408 has different control functions 482, 484, 486, 488, 490, 492, 494, 496, 497 in addition to the same control functions 278, 280 as those 278, 280 of the control device 258 of the third apparatus 208 shown in FIG. 10. The fifth apparatus 408 is controlled according to the control program represented by the flow charts of FIGS. 26 and 27, in place of the control program represented by the flow chart of FIG. 11. However, the main routine represented by the flow chart of FIG. 26 has the same steps SA201 through SA208, SA216, SA221, and SA222 as those SA201-SA208, SA216, SA221, SA222 of the control program represented by the flow chart of FIG. 11, and the same steps SA309, SA310 as those SA309, SA310 of the main routine of FIG. 20 employed in the fourth apparatus 308. The subroutine of FIG. 27 has the same step SB301 as that SB301 of the subroutine of FIG. 21 employed in the fourth apparatus 308. The description of those steps is omitted from the following description.

The following description relates to only the differences of the fifth apparatus 408 from the third apparatus 208 or the fourth apparatus 308.

In the present embodiment, an inflatable cuff 215, a pressure sensor 240, a pulse-wave filter circuit 254, etc. cooperate with one another to provide one of a pair of heartbeat-synchronous-wave (HSW) sensors, and a cuff pulse wave (CPW) or a CPW signal $SM_1$ detected or provided by this HSW sensor corresponds to a heartbeat-synchronous wave (HSW) which is produced from an artery of a living subject in synchronism with the heartbeat of the subject.

In addition, in the present embodiment, an electrocardiographic-waveform (ECG-waveform) detecting device 270 and two electrodes 218 cooperate with one another to provide the other of the pair of HSW sensors, and an ECG waveform detected by this HSW sensor corresponds to another HSW.

The ECG-wave detecting device 270 detects the ECG waveform of the subject through the two electrodes 218 respectively held in contact with a right and a left arm 212, 213 of the subject. An example of the ECG waveform represented by an electric signal supplied from the detecting device 270 is shown in an upper portion of the graph of FIG. 24. An example of the CPW waveform detected through the pressure sensor 240 is shown in a lower portion of the graph of FIG. 24.

FIG. 23 illustrates essential control functions of the control device 258 of the fifth apparatus 408. The control device 258 functions as a cuff-pressure regulating means 278 and a BP measuring means 280 which are the same as the cuff-pressure regulating means 278 and the BP measuring means 280, respectively, of the third apparatus 208 shown in FIG. 10.

Figure 24:
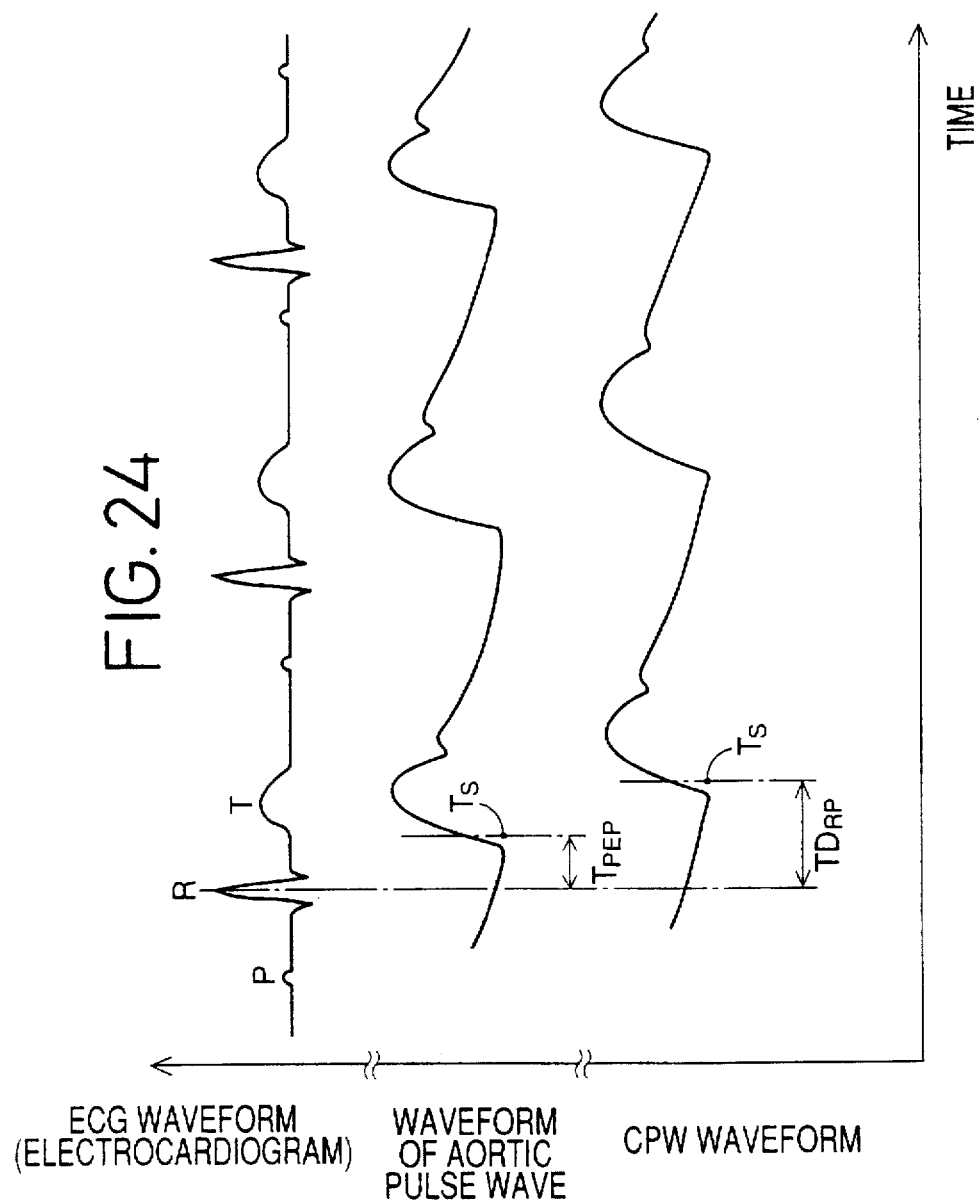
FIG. 24 is a time chart for illustrating a time difference $TD_{RP}$ which is determined by the control device of the apparatus of FIG. 23.

The control device 258 of the fifth apparatus 408 additionally functions as a time-difference determining means 482 which successively determines a time difference between a predetermined periodic point relating to the ECG waveform of each of heartbeat-synchronous pulses of the electric signal supplied from the ECG-waveform detecting device 270, and a predetermined periodic point relating to the CPW waveform of a corresponding one of heartbeat-synchronous pulses of the CPW signal $SM_1$ which is supplied from the pressure sensor 240 when the pressure of the cuff 215 is changed around a diastolic BP value DBP of the subject. In the present embodiment, the determining means 482 determines a time difference, $TD_{RP}$, between the time of occurrence or detection of an R wave of each pulse of the ECG waveform and the time of occurrence or detection of a reference point, $T_S$, which is determined, as described later, with respect to a corresponding pulse of the CPW waveform, as shown in FIG. 24.

The control device 258 of the fifth apparatus 408 functions as a temporary-propagation-velocity determining means 484 which successively determines a temporary propagation velocity $V_{M1}$ (m/sec) of CPW, based on each of the successively determined time-difference values $TD_{RP}$, according to the same expression as the previously-indicated expression (2): $V_{M1}=L/(TD_{RP}-T_{PEP})$. In the present embodiment, the pre-ejection period $T_{PEP}$ is defined as a time interval (sec) between the R wave of ECG waveform and a reference point $T_S$ of an aortic pulse wave, as illustrated in FIG. 24. The respective values of length L (m) and pre-ejection period $T_{PEP}$ are experimentally determined in advance.

In addition, the control device 258 of the fifth apparatus 408 functions as a maximum-slope-line determining means 486 which determines, with respect to each pulse of the CPW waveform, a maximum-slope line, $L_{Kmax}$, (indicated at broken line in FIG. 25) which passes through a maximum-slope point, $K_{max}$, where the CPW waveform takes a maximum slope, such that the maximum-slope line $L_{Kmax}$ has the maximum slope. More specifically described, the determining means 486 differentiates the CPW waveform and determines, as the maximum-slope point $K_{max}$, a point where the differentiated waveform or curve takes a maximum value.

The control device 258 of the fifth apparatus 408 also functions as a base-line determining means 488 which determines, with respect to each pulse of the CPW waveform, a base line, BL, (indicated at one-dot chain line in FIG. 25) which passes through respective minimum points on both sides of a maximum point of each pulse of CPW. In the present embodiment, one of the two minimum points (i.e., left one in FIG. 25) detected before the maximum point is defined as the minimum point of the current pulse, and the other minimum point (i.e., right one) detected after the maximum point is defined as the minimum point of the next pulse of CPW. One pulse of CPW corresponds to one beat of the heart of the subject.

Further, the control device 258 of the fifth apparatus 408 also functions as a reference-point determining means 490 which determines, as the reference point $T_S$, a point of intersection of the maximum-slope line $L_{Kmax}$ and the base line BL.

Moreover, the control device 258 of the fifth apparatus 408 functions as a stability judging means 492, a proper-propagation-velocity determining means 494, a propagation-velocity modifying means 497, and a coefficient determining means 496 which are the same as those 386, 387, 389, 388 of the fourth apparatus 308 shown in FIG. 16, and the description thereof is omitted.

Hereinafter, there will be described the operation of the BP measuring apparatus 408 constructed as described above, by reference to the flow charts of FIGS. 26 and 27.

Figure 26:
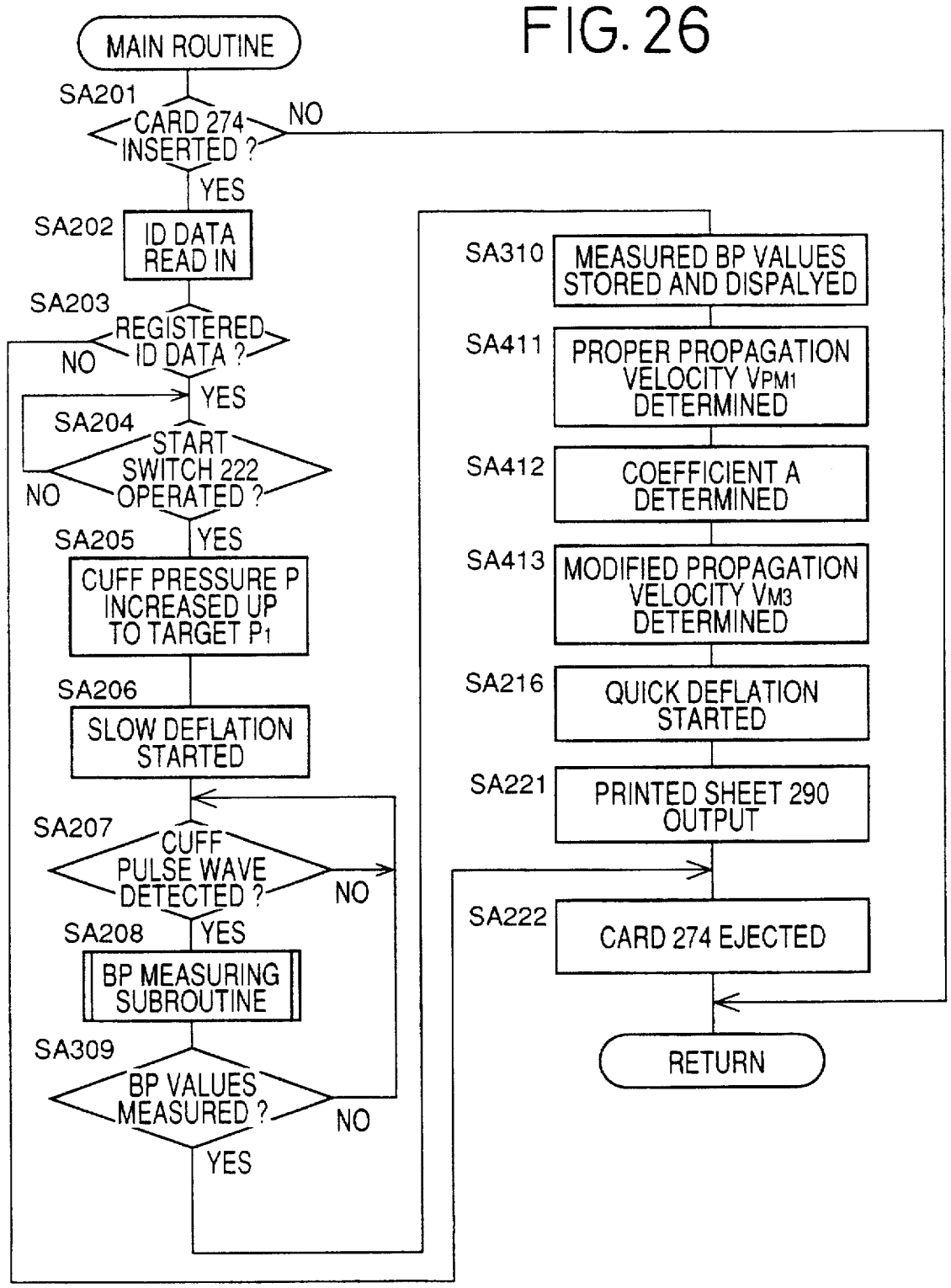
FIG. 26 is a flow chart representing a control program according to which the apparatus of FIG. 23 is controlled.

Steps SA201 to SA208 of FIG. 26 are the same as those SA201 to SA208 of FIG. 11.

Steps SA309 and SA310 of FIG. 26 are the same as those SA309, SA310 of FIG. 20.

Step SA310 is followed by Step SA411 to determine, as a proper propagation velocity $V_{PM1}$ of the subject, an average of the first, second, and third temporary propagation-velocity values $V_{M1}$ which have first, second, and third become not higher than a first or a second reference value and have been stored in a second memory area of a RAM 266 of the control device 258 of the fifth apparatus 408. Step SA411 corresponds to the proper-propagation-velocity determining means 494.

Step SA411 is followed by Step SA412 to determine a coefficient A occurring in the expression (7), based on the proper propagation velocity $V_{PM1}$ determined at Step SA411 and a diastolic BP value $DBP_1$ determined at Step SA208, according to the expression (8). Step SA412 corresponds to the coefficient determining means 496. Step SA412 is followed by Step SA413 to modify the proper propagation velocity $V_{PM1}$ determined at Step SA411 to a modified, i.e., normalized proper propagation velocity $V_{M3}$ corresponding to a predetermined BP value $BP_r$ and a predetermined pulse rate $HR_r$, based on the diastolic BP value $DBP_1$ and a pulse rate $HR_1$ measured at Step SA208, according to the expression (7). Step SA413 corresponds to the propagation-velocity modifying means 497.

Step SA413 is followed by Steps SA216, SA221, and SA222 which are the same as Steps SA216, SA221, SA222 of FIG. 11.

Figure 27:
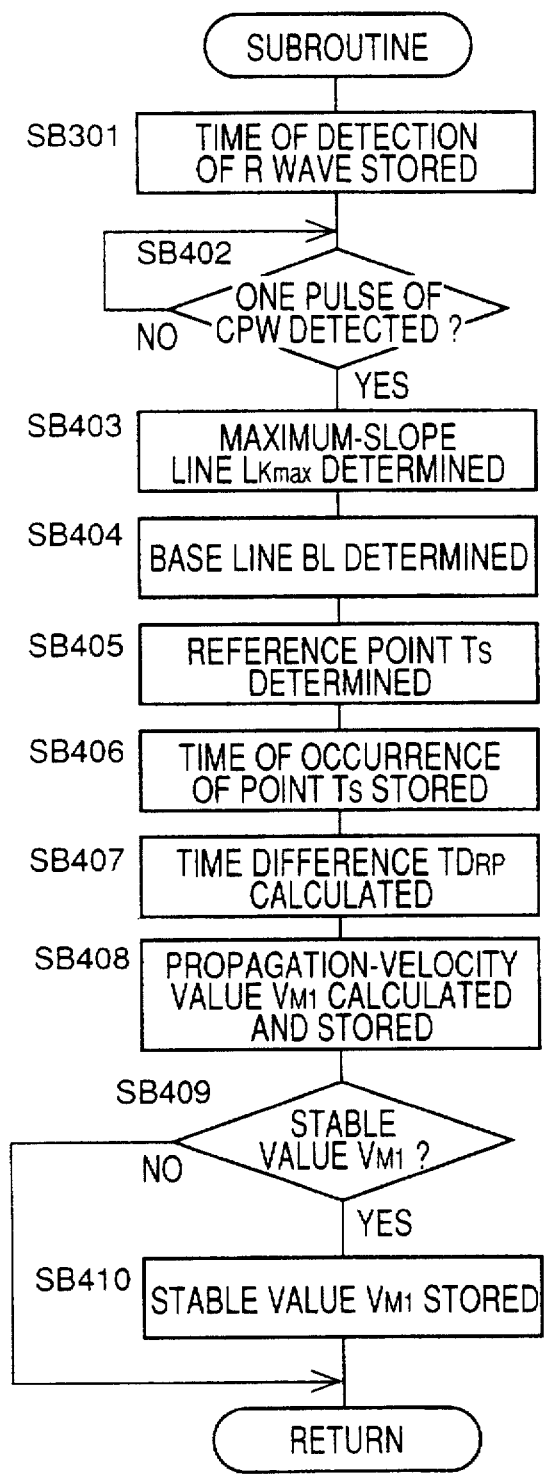
FIG. 27 is a flow chart representing an interrupt subroutine according to which the apparatus of FIG. 23 is controlled.

The flow chart of FIG. 27 represents an interrupt subroutine which is implemented when the CPU 262 reads in the R wave of each heartbeat-synchronous pulse of the ECG waveform (i.e., electric signal) detected by the ECG-waveform detecting device 270, while the main routine represented by the flow chart of FIG. 26 is implemented. Step SB301 of FIG. 27 is the same as Step SB301 of FIG. 21. That is, at Step SB402, the CPU 262 of the control device 258 of the fifth apparatus 408 specifies the time when the R wave of one pulse is detected or read in, and stores the specified time in the RAM 266. Step SB301 is followed by Step SB402 to judge whether the CPU 262 has read in one heartbeat-synchronous pulse of the CPW waveform (i.e., CPW signal $SM_1$) detected through the pressure sensor 240. If a negative judgment is made at Step SB402, Step SB402 is repeated until a positive judgment is made. Meanwhile, if a positive judgment is made at Step SB402, the control of the CPU 262 goes to Step SB403 to determine a maximum-slope point $K_{max}$ of the pulse of CPW where the differentiated waveform or curve derived from the original CPW waveform shown in FIG. 25 takes a maximum value, i.e., where the CPW waveform takes a maximum slope. In addition, at Step SB403, the CPU 262 determines a maximum-slope line $L_{Kmax}$ which passes through the maximum-slope point $K_{max}$ and has the maximum slope. Step SB403 corresponds to the maximum-line determining means 486.

Figure 25:
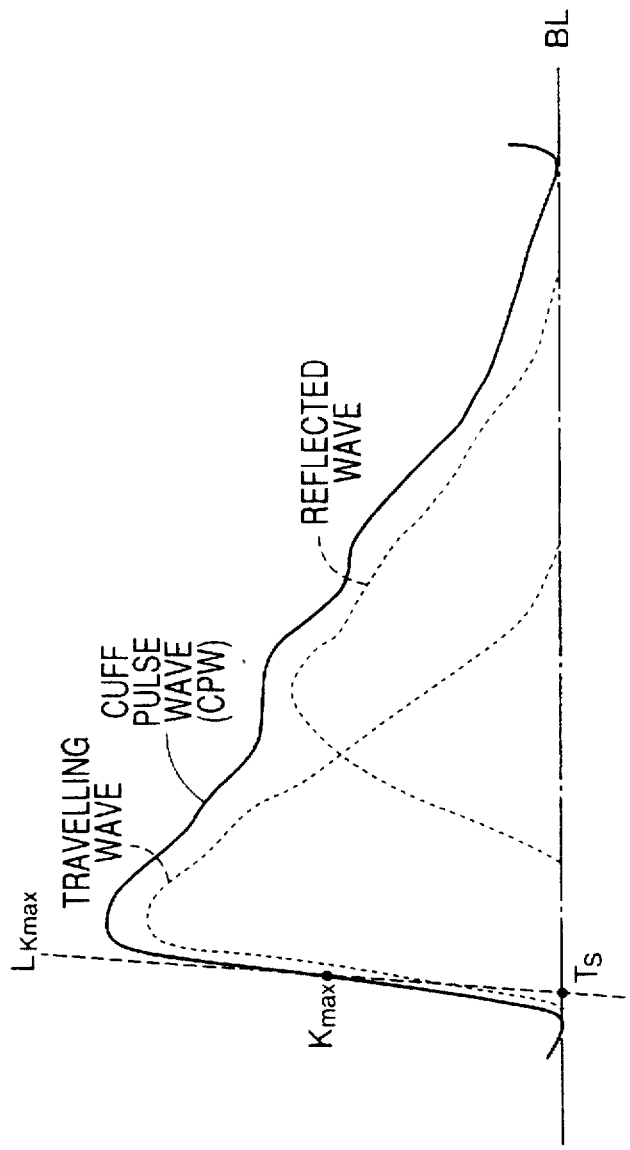
FIG. 25 is an enlarged view for illustrating a reference point, $T_S$, determined by the control device of the apparatus of FIG. 23.

Step S403 is followed by Step S404 to determine a base line BL which passes through the two minimum points before and after the maximum point of the CPW pulse. Step SB404 corresponds to the base-line determining means 488. Step SB404 is followed by Step SB405 to determine, as the reference point $T_S$ relating to the CPW pulse, a point of intersection of the maximum-slope line $L_{Kmax}$ and the base line BL, as shown in FIG. 25. Step SB405 corresponds to the reference-point determining means 490.

Step SB405 is followed by Step SB406 to specify the time when the reference point $T_S$ of the CPW pulse is detected or read in, and stores the specified time in the RAM 266. Step SB406 is followed by Step SB407.

At Step SB407, the CPU 262 determines a time difference $TD_{RP}$ between the time of detection of the R wave of the ECG pulse and the time of occurrence of the reference point $T_S$ of the corresponding CPW pulse, as illustrated in FIG. 24. Step SB407 corresponds to the time-difference determining means 482. Step SB407 is followed by Step SB408 to determine a temporary propagation velocity $V_{M1}$ of CPW, based on the time difference $TD_{RP}$ determined at Step SB407, according to the expression (2). The determined temporary value $V_{M1}$ is stored in a first memory area of the RAM 66. Step SB408 corresponds to the temporary-propagation-velocity determining means 484.

Subsequently, at Step SB409, the CPU 262 judges whether the amount or rate of change of the current temporary propagation-velocity value $V_{M1}$ determined at Step SB408 in the current control cycle, from the preceding value $V_{M1}$ determined at Step SB408 in the preceding control cycle and stored in the first memory area of the RAM 266, is not greater than 0.1 m/sec or 3%. If a negative judgment is made at Step SB409, the current control cycle in accordance with this subroutine is ended. On the other hand, if a positive judgment is made at Step SB409, the control of the CPU 262 goes to Step SB410 to store temporarily the current propagation-velocity value $V_{M1}$ determined at Step SB408 in the current control cycle, in the second memory area of the RAM 266. Step SB409 corresponds to the stability judging means 492.

As is apparent from the foregoing description, in the fifth embodiment shown in FIGS. 23 to 27, the CPU 256 determines, at Step SB403, the maximum-slope line $L_{Kmax}$ which passes through the maximum-slope point $K_{max}$ and has the maximum slope and, at Step S404, determines the base line BL which passes through the two minimum points before and after the maximum point of each CPW pulse. In addition, at Step SB405, the CPU 262 determines, as the reference point $T_S$ relating to each CPW pulse, a point of intersection of the maximum-slope line $L_{Kmax}$ and the base line BL. This reference point $T_S$ is free from the influences of a reflected wave as a secondary component of the CPW waveform, as shown in FIG. 25. Therefore, the reference point $T_S$ does not substantially change or move on even a CPW waveform obtained from a living subject who suffers a serious arterial sclerosis. Accordingly, the present apparatus 408 measures, with high accuracy, the propagation velocity of a pulse wave which is propagated through an artery of a living subject.

Figure 28:
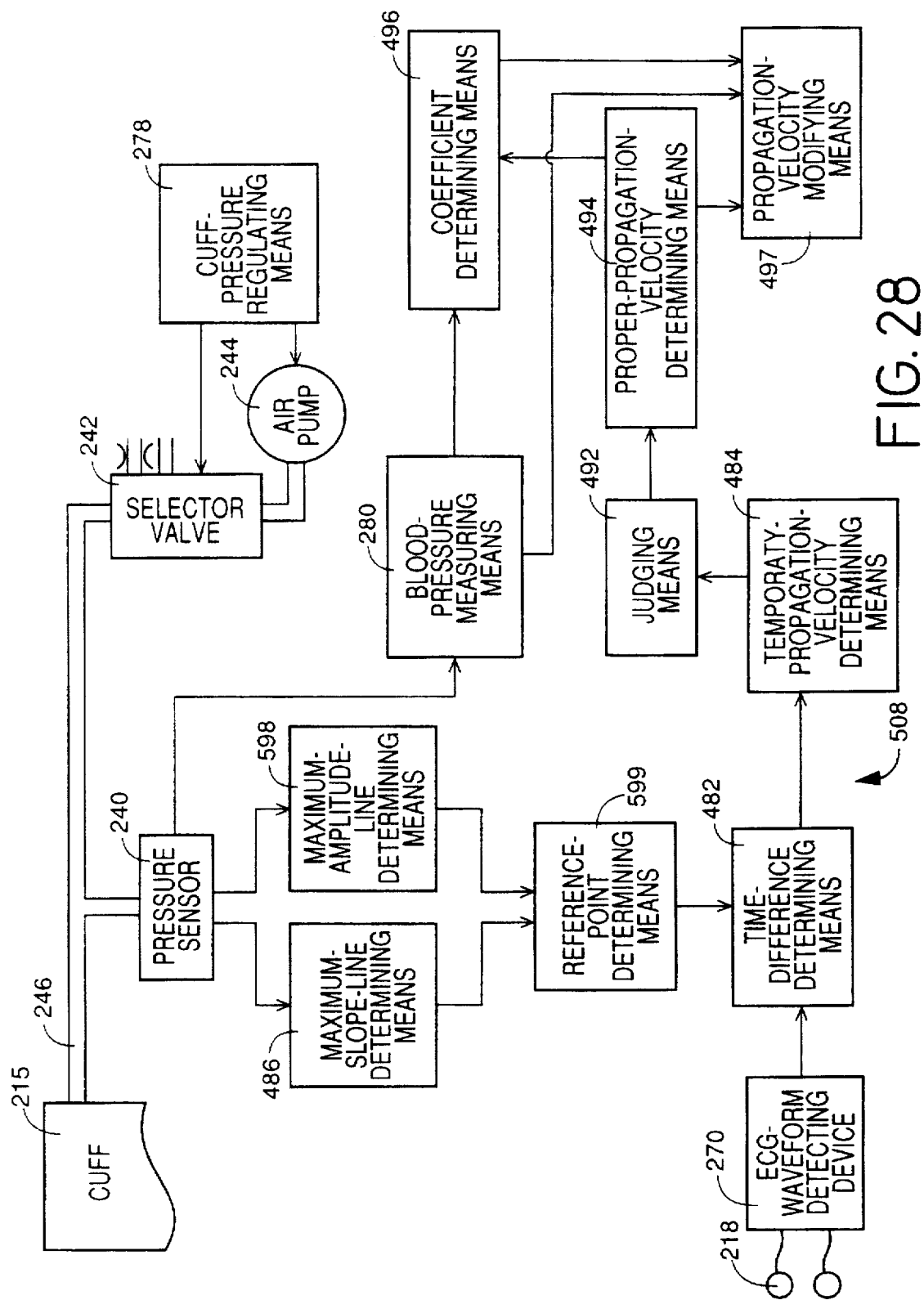
FIG. 28 is a block diagram corresponding to FIG. 23, for illustrating essential functions of an electronic control device of another BP measuring apparatus providing another propagation-velocity measuring apparatus as a sixth embodiment of the present invention.
Figure 29:
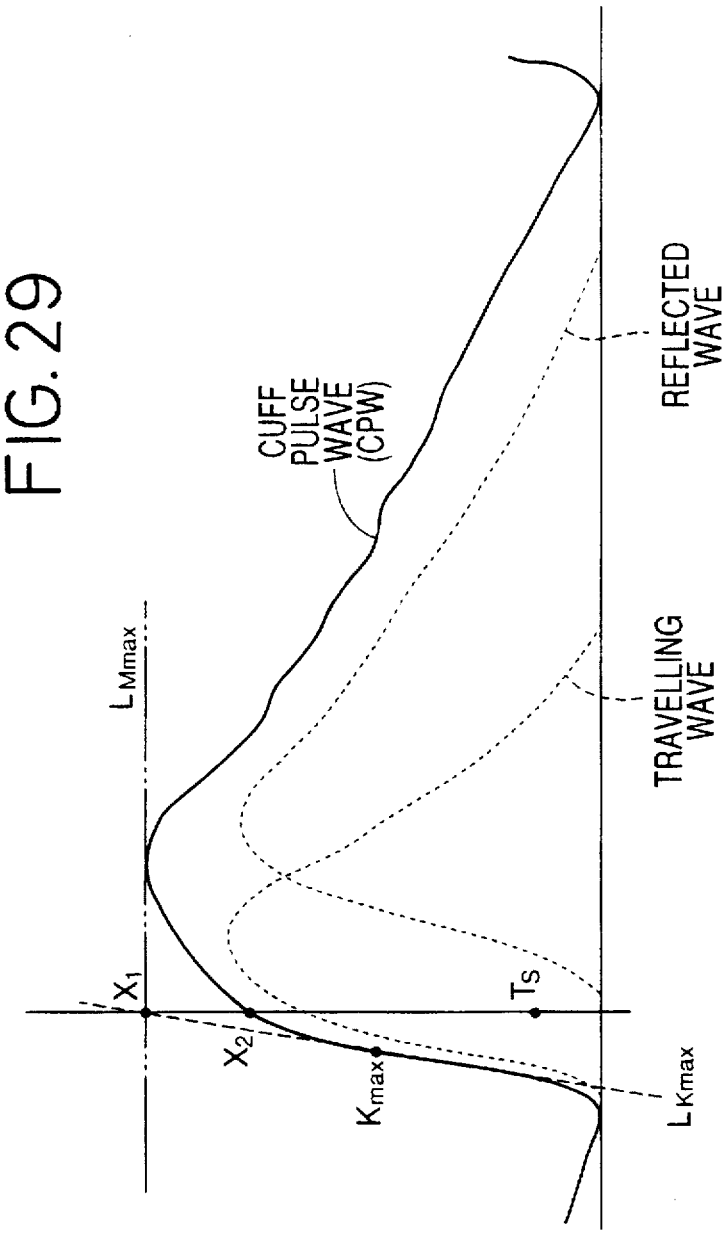
FIG. 29 is an enlarged view corresponding to FIG. 25, for illustrating a reference point $T_S$ determined by the control device of the apparatus of FIG. 28.
Figure 30:
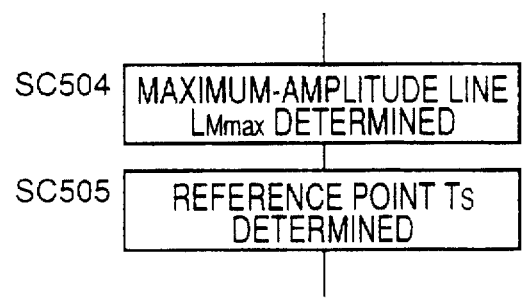
FIG. 30 is a flow chart representing an interrupt subroutine according to which the apparatus of FIG. 28 is controlled.

Referring next to FIGS. 28 to 30, there will described a sixth embodiment of the present invention which relates to an automatic BP measuring apparatus 508 which automatically measures a BP value of a living subject and which also functions as an apparatus for measuring a propagation velocity of a pulse wave which is propagated through an artery of the subject.

The BP measuring apparatus 508 as the sixth embodiment has the same hardware construction as the BP measuring apparatus 208 as the third embodiment shown in FIGS. 8 and 9. The same reference numerals as used in FIGS. 8 and 9 are used to designate the corresponding elements or parts of the sixth apparatus 508, and the description thereof is omitted from the following description.

However, as shown in FIG. 28, an electronic control device 258 of the sixth apparatus 508 has different control functions 598, 599 in addition to the same control functions 278, 280 as those 278, 280 of the control device 258 of the third apparatus 208 shown in FIG. 10 and the same control functions 482, 484, 486, 492, 494, 496, 497 as those 482, 484, 486, 492, 494, 496, 497 of the control device 258 of the fifth apparatus 408 shown in FIG. 23.

The sixth apparatus 508 is controlled according to the control program represented by the flow chart of FIG. 26 employed in the fifth apparatus 408 and the flow chart of FIG. 30. The subroutine of FIG. 30 is different from the subroutine of FIG. 27 employed in the fifth apparatus 408 only in that the former has Steps SC504 and SC505 in place of Steps SB404 and SB405 of the latter.

The following description relates to only the differences of the sixth apparatus 508 from the fifth apparatus 408.

FIG. 28 illustrates essential control functions of the control device 258 of the sixth apparatus 508. The control device 258 functions as a maximum-point-line determining means 598 which determines, with respect to each pulse of the CPW waveform, a maximum-point line, $L_{Mmax}$, (indicated at two-dot chain line in FIG. 29) which passes through a maximum point, $M_{max}$, where the waveform of the CPW pulse takes a maximum amplitude, such that the maximum-point line $L_{Mmax}$ is parallel to a base line BL which passes through respective minimum points on both sides of the maximum point $M_{max}$ of the CPW pulse. In the present embodiment, the amplitude of each point on the CPW waveform is defined as the distance of each point from the base line BL.

The control device 258 of the sixth apparatus 508 also functions as a reference-point determining means 599 which determines a reference point, $T_S$, based on a point of intersection, $X_2$, of the CPW waveform and a straight line which passes through a point of intersection, $X_1$, of the maximum-point line $L_{Mmax}$ and a maximum-slope line $L_{Kmax}$ (indicated at broken line in FIG. 29) determined by a maximum-slope-line determining means 486 and which is perpendicular to the maximum-point line $L_{Mmax}$. More specifically described, a point having an amplitude equal to one fifth of the amplitude of the point $X_2$ is determined as the reference point $T_S$, as shown in FIG. 29.

Next, there will be described the operation of the BP measuring apparatus 508 constructed as described above. The present apparatus 508 is operated according to the main routine represented by the flow chart of FIG. 26 and the subroutine represented by the flow chart of FIG. 30. Since, however, the subroutine FIG. 30 is different from that of FIG. 27 only in that the former has Steps SC504 and SC505 in place of Steps SB404 and SB405 of FIG. 27, the following description relates only to Steps SC504 and SC505.

At Step SC504, the CPU 262 of the control device 258 of the sixth apparatus 508 determines, with respect to each pulse of the CPW waveform, a maximum-point line $L_{Mmax}$ which passes through a maximum point $M_{max}$ where the waveform of the CPW pulse takes a maximum amplitude, such that the maximum-point line $L_{Mmax}$ is parallel to a base line BL which passes through respective minimum points on both sides of the maximum point $M_{max}$ of the CPW pulse. Step SC504 corresponds to the maximum-point-line determining means 598.

Step SC504 is followed by Step SC505 to determine a reference point $T_S$ based on a point of intersection $X_2$ of the CPW waveform and a straight line which passes through a point of intersection $X_1$ of the maximum-point line $L_{Mmax}$ and a maximum-slope line $L_{Kmax}$ determined at Step SB403 and which is perpendicular to the maximum-point line $L_{Mmax}$. For example, a point having an amplitude equal to one fifth of the amplitude of the point $X_2$ is determined as the reference point $T_S$. Step SC505 corresponds to the reference-point determining means 599.

As is apparent from the foregoing description, in the sixth embodiment shown in FIGS. 28 through 30, the CPU 262 determines, at Step SB403, the maximum-slope line $L_{Kmax}$ which passes through the maximum-slope point $K_{max}$ of the CPW waveform and has the maximum slope and, at Step SC504, determines the maximum-point line $L_{Mmax}$ which passes through the maximum point $M_{max}$ of the CPW waveform and extends parallel to the base line BL which passes through the two minimum points on both sides of the maximum point $M_{max}$. In addition, the CPU 262 determines, at Step SC505, the reference point $T_S$ based on the point of intersection $X_2$ of the CPW waveform and the straight line which passes through the point of intersection $X_1$ of the maximum-point line $L_{Mmax}$ and the maximum-slope line $L_{Kmax}$ determined at Step SB403 and which is perpendicular to the maximum-point line $L_{Mmax}$. for example, determines a point having an amplitude equal to one fifth of the amplitude of the point $X_2$, as the reference point $T_S$. This reference point $T_S$ is free from the influences of a reflected wave as a component of the CPW waveform, as shown in FIG. 29. Therefore, the reference point $T_S$ does not change or move on even a CPW waveform obtained from a living subject suffering a serious arterial sclerosis. Accordingly, the present apparatus 508 measures, with high accuracy, the propagation velocity of a pulse wave which is propagated through an artery of a living subject.

In the present embodiment, a point having an amplitude equal to one fifth of the amplitude of the point $X_2$, is determined as the reference point $T_S$. However, it is possible to determine, as the reference point $T_S$, a point having an amplitude equal to one third or one tenth of the amplitude of the point $X_2$, or otherwise to determine the point $X_2$ itself as the reference point $T_S$.

Figure 32:
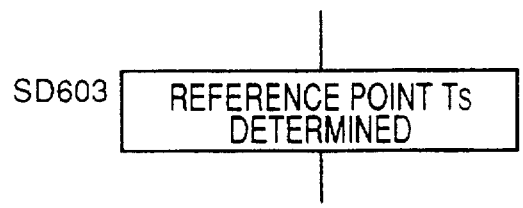
FIG. 32 is a flow chart representing an interrupt subroutine according to which the apparatus of FIG. 31 is controlled.
Figure 31:
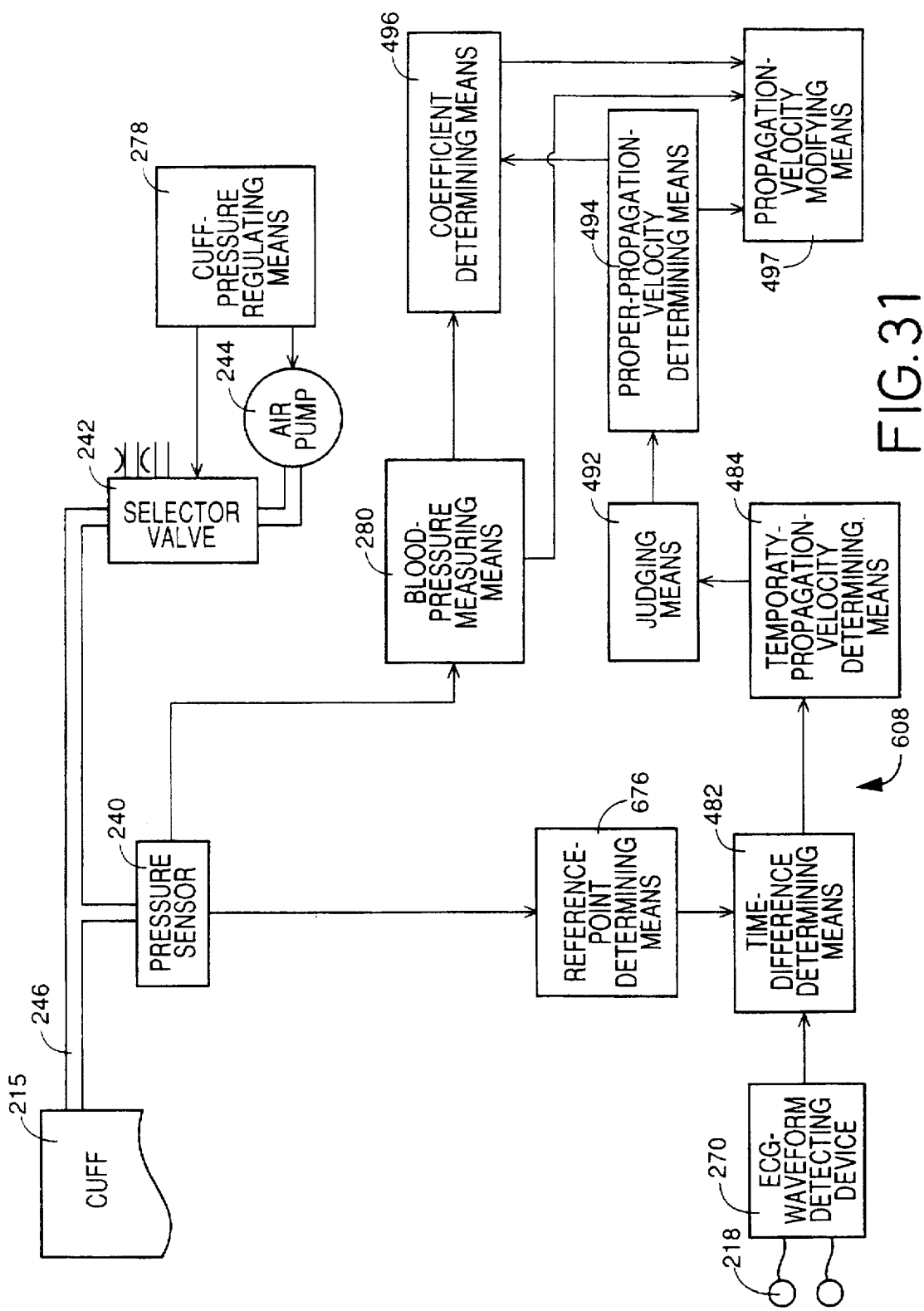
FIG. 31 is a block diagram corresponding to FIG. 23, for illustrating essential functions of an electronic control device of another BP measuring apparatus providing another propagation-velocity measuring apparatus as a seventh embodiment of the present invention.

Referring next to FIGS. 31 and 32, there will described a seventh embodiment of the present invention which relates to an automatic BP measuring apparatus 608 which automatically measures a BP value of a living subject and which also functions as an apparatus for measuring a propagation velocity of a pulse wave which is propagated through an artery of the subject.

The BP measuring apparatus 608 as the seventh embodiment has the same hardware construction as the BP measuring apparatus 208 as the third embodiment shown in FIGS. 8 and 9. The same reference numerals as used in FIGS. 8 and 9 are used to designate the corresponding elements or parts of the seventh apparatus 608, and the description thereof is omitted from the following description.

However, as shown in FIG. 31, an electronic control device 258 of the seventh apparatus 608 has a different control function 676 in addition to the same control functions 278, 280 as those 278, 280 of the control device 258 of the third apparatus 208 shown in FIG. 10 and the same control functions 482, 484, 492, 494, 496, 497 as those 482, 484, 492, 494, 496, 497 of the control device 258 of the fifth apparatus 408 as shown in FIG. 23.

The seventh apparatus 608 is controlled according to the control program represented by the flow chart of FIG. 26 employed in the fifth apparatus 408 and the flow chart of FIG. 32. The subroutine of FIG. 32 is different from the subroutine of FIG. 27 employed in the fifth apparatus 408 only in that the former has Step SD603 in place of Steps SB403, SB404, and SB405 of the latter.

The following description relates to only the differences of the seventh apparatus 608 from the fifth apparatus 408.

FIG. 31 illustrates essential control functions of the control device 258 of the seventh apparatus 608. The control device 258 functions a reference-point determining means 676 which determines, with respect to each pulse of the CPW waveform, a maximum-slope point $K_{max}$ (shown in FIG. 25) where the CPW waveform takes a maximum slope. For example, the determining means 676 differentiates the CPW waveform and determines, as the maximum-slope point $K_{max}$, a point where the differentiated waveform or curve takes a maximum value. In addition, the determining means 676 determines the maximum-slope point $K_{max}$ as a reference point, $T_S$.

Next, there will be described the operation of the BP measuring apparatus 608 constructed as described above.

The present apparatus 608 is operated according to the main routine represented by the flow chart of FIG. 26 and the subroutine represented by the flow chart of FIG. 32. Since, however, the subroutine FIG. 32 is different from that of FIG. 27 only in that the former has Step SD603 in place of Steps SB403, SB404, and SB405 of FIG. 27, the following description relates only to Step SD603.

At Step SD603, a CPU 262 of the control device 258 of the seventh apparatus 608 determines, with respect to each pulse of the CPW waveform, a maximum-slope point $K_{max}$ of the CPW pulse where the differentiated waveform or curve derived from the original CPW waveform shown in FIG. 25 takes a maximum value, i.e., where the CPW waveform takes a maximum slope. In addition, the CPU 262 determines the maximum-slope point $K_{max}$ as the reference point $T_S$. The time of occurrence of this reference point $T_S$ is specified at Step SB406, and this time is used to determine a time difference $TD_{RP}$ at, Step SB407. Step SD603 corresponds to the reference-point determining means 676.

As is apparent from the foregoing description, in the seventh embodiment shown in FIGS. 31 and 32, the CPU 262 determines, at Step SD603, the maximum-slope point $K_{max}$ of each pulse of the CPW waveform and determines this point $K_{max}$ as the reference point $T_S$. The reference point $T_S$ is free from the influences of a reflected wave as a component of the CPW waveform, as shown in FIG. 25. Therefore, the reference point $T_S$ does not change or move on even a CPW waveform obtained from a living subject having a serious arterial sclerosis. Accordingly, the present apparatus 608 measures, with high accuracy, the propagation velocity of a pulse wave which is propagated through an artery of a living subject.

While in each of the fifth to seventh embodiments the propagation velocity $V_{M1}$, $V_{PM1}$, $V_{M3}$ is determined based on the time difference $TD_{RP}$ between each pulse of the ECG waveform and a corresponding pulse of the PPW or CPW waveform, it is possible to determine a propagation velocity based on a time difference of a heartbeat-synchronous pulse of a first pulse wave detected by a first pulse-wave sensor and a corresponding heartbeat-synchronous pulse of a second pulse wave detected by a second pulse-wave sensor. In the latter case, the two pulse-wave sensors are worn on different portions of the subject, and a reference point $T_S$ is determined with respect to each of the first and second pulse waves. The two pulse-wave sensors correspond to the pair of heartbeat-synchronous-wave sensors, and the two pulse waves correspond to the two heartbeat-synchronous waves, respectively.

It is to be understood that the present invention may be embodied with various changes, improvements, and modifications that may occur to those skilled in the art without departing from the scope and spirit of the invention defined in the appended claims.

What is claimed is:

1. An apparatus for measuring a propagation velocity of a pulse wave which is propagated through an artery of a living subject, the apparatus comprising:

an electrocardiographic-waveform detecting device which detects an electrocardiographic waveform from the subject, the detected electrocardiographic waveform comprising a plurality of first heartbeat-synchronous pulses;

a pulse-wave sensor which is adapted to be worn on the subject and which detects the pulse wave from the subject, the detected pulse wave comprising a plurality of second heartbeat-synchronous pulses;

time-difference determining means for determining a time difference between a first periodic point relating to one of the first heartbeat-synchronous pulses of the detected electrocardiographic waveform and a second periodic point relating to a corresponding one of the second heartbeat-synchronous pulses of the detected pulse wave; and propagation-velocity determining means for determining the propagation velocity, $V_M$, of the pulse wave based on the determined time difference, $TD_{RP}$, according to a following expression:

$$V_M = L/(TD_{RP} - T_{PEP})$$

where

L is a length of the artery of the subject from a left ventricle of the subject via an aorta of the subject to a position where the pulse-wave sensor is worn on the subject, and $T_{PEP}$ is a pre-ejection period between a Q wave of said one first heartbeat-synchronous pulse of the electrocardiographic waveform and a minimum point of said corresponding one of the second heartbeat-synchronous pulses of the pulse wave.

2. An apparatus according to claim 1, wherein said pulse-wave sensor comprises a pressure sensor which is adapted to be pressed against a portion of the artery of the subject via a skin of the subject and which detects, as the pulse wave, a heartbeat-synchronous pressure oscillation which is transmitted thereto from the portion of the artery via the skin.

3. An apparatus according to claim 1, wherein said pulse-wave sensor comprises:

an inflatable cuff which is adapted to be wound around a body portion of the subject; and a pressure sensor which detects, as the pulse wave, a heartbeat-synchronous pressure oscillation which is produced in said cuff.

4. An apparatus according to claim 1, wherein said pulse-wave sensor comprises a photoelectric sensor including a light source which emits a light toward a body portion of the subject, and a light detecting element which detects the light transmitted through, or reflected from, the body portion.

5. An apparatus according to claim 1, further comprising:

a blood-pressure measuring device which measures a blood pressure value of the subject; and propagation-velocity modifying means for modifying the determined propagation-velocity value to a modified propagation-velocity value corresponding to a predetermined blood pressure value, based on the measured blood pressure value, according to a predetermined relationship between modified propagation velocity, and determined propagation velocity and measured blood pressure.

6. An apparatus according to claim 1, further comprising a blood-pressure measuring device which includes an inflatable cuff adapted to be wound around a body portion of the subject, said pulse-wave sensor which detects the pulse wave transmitted from the artery of the subject to said cuff when a pressure in the cuff is changed, and means for determining a blood pressure value of the subject based on the detected pulse wave, wherein said time-difference determining means comprises means for successively determining the time difference between the first periodic point on the detected electrocardiographic waveform and the second periodic point on the detected pulse wave, and said propagation-velocity determining means comprises temporary-propagation-velocity determining means for successively determining the temporary propagation velocity of the pulse wave based on each of the successively determined time-difference values; judging means for judging whether the change of each of the successively determined temporary propagation-velocity values, with respect to the change of the cuff pressure, is smaller than a reference value; and proper-propagation-velocity determining means for determining a proper propagation-velocity value from at least one temporary propagation-velocity value for which a positive judgment is made by said judging means.

7. An apparatus according to claim 1, further comprising:

a blood-pressure measuring device which includes an inflatable cuff adapted to be wound around a body portion of the subject, said pulse-wave sensor which detects a plurality of heartbeat-synchronous pulses of the pulse wave transmitted from the artery of the subject to said cuff when a pressure in the cuff is changed, and means for determining a blood pressure value of the subject based on variation of respective amplitudes of the detected heartbeat-synchronous pulses of the pulse wave, wherein said time-difference determining means successively determines the time difference between the first periodic point on each of heartbeat-synchronous pulses of the detected electrocardiographic waveform and the second periodic point on a corresponding one of the detected heartbeat-synchronous pulses of the pulse wave and said propagation-velocity determining means successively determines the propagation velocity of the pulse wave based on each of the successively determined time-difference values;

judging means for judging whether the change of each of the successively determined propagation-velocity values, with respect to the change of the cuff pressure, is smaller than a reference value; and correcting means for correcting at least one first pulse of the heartbeat-synchronous pulses of the pulse wave which is deviated from at least one second pulse for which a positive judgment is made by said judging means, based on the deviation of the first pulse from the second pulse, so that said blood-pressure measuring device measures the blood pressure value of the subject based on the variation of the respective amplitudes of the heartbeat-synchronous pulses including the corrected first pulse.

8. An apparatus according to claim 1, further comprising:

a blood-pressure measuring device which includes an inflatable cuff adapted to be wound around a body portion of the subject, said pulse-wave sensor which detects the pulse wave transmitted from the artery of the subject to said cuff when a pressure in the cuff is changed, and means for determining a blood pressure value of the subject based on the detected pulse wave; and terminating means for terminating a blood pressure measurement of said blood-pressure measuring device when the determined propagation-velocity value does not fall within a permission range.

9. An apparatus according to claim 1, further comprising second-periodic-point determining means for determining said second periodic point based on a curve obtained by differentiating said detected pulse wave.

10. An apparatus according to claim 9, wherein said second-periodic-point determining means comprises means for determining said second periodic point based on a maximum-slope point where said detected pulse wave takes a maximum slope.

11. An apparatus according to claim 9, wherein said second-periodic-point determining means comprises means for determining, as said second periodic point, a maximum-slope point where said detected pulse wave takes a maximum slope.

12. An apparatus according to claim 1, further comprising:

an inflatable cuff which is adapted to be wound around a body portion of the subject;

a pressure sensor which detects a heartbeat-synchronous pressure oscillation which is produced in the cuff while a pressure in the cuff is changed, the detected heartbeat-synchronous pressure oscillation comprising a plurality of third heartbeat-synchronous pulses;

first blood pressure determining means for determining an actual blood pressure of the subject based on a variation of respective amplitudes of the third heartbeat-synchronous pulses of the detected heartbeat-synchronous pressure oscillation;

relationship determining means for determining a relationship between blood pressure and pulse wave magnitude based on at least one actual blood pressure value determined by the first blood pressure determining means and at least one magnitude of one of the second heartbeat-synchronous pulses of the pulse wave detected by the pulse-wave sensor; and second blood pressure determining means for successively determining, according to the relationship determined by the relationship determining means, a blood pressure value of the subject based on a magnitude of each of the second heartbeat-synchronous pulses of the pulse wave which are detected after the relationship is determined.

13. An apparatus according to claim 12, wherein the pulse-wave sensor comprises a pressure pulse-wave sensor which is adapted to be pressed against a portion of the artery of the subject via a skin of the subject and which detects, as the pulse wave, a heartbeat-synchronous pressure pulse wave which is transmitted thereto from the portion of the artery via the skin, the detected heartbeat-synchronous pressure pulse wave comprising a plurality of second heartbeat-synchronous pulses, and wherein the relationship determining means comprises means for determining, as the relationship between blood pressure, MBP, and pressure-pulse-wave magnitude, $P_M$, a linear function: $MBP = A \cdot P_M + B$, where A and B are a first and a second constant, respectively, based on at least one actual blood pressure determined by the first blood pressure determining means and at least one magnitude of one of the second heartbeat-synchronous pulses of the pressure pulse wave detected by the pressure pulse-wave sensor.

14. An apparatus according to claim 13, wherein the second blood pressure determining means comprises means for successively determining, according to the linear function, a systolic and diastolic blood pressure value of the subject based on a maximum and a minimum magnitude of each of the second heartbeat-synchronous pulses of the pressure pulse wave which are detected by the pressure pulse-wave sensor after the linear function is determined.

* * * * *